United States Patent [19]

Stolowitz et al.

[11] Patent Number: 5,872,224
[45] Date of Patent: Feb. 16, 1999

[54] BORONIC COMPOUND COMPLEXING REAGENTS AND HIGHLY STABLE COMPLEXES

[75] Inventors: Mark L. Stolowitz, Woodinville; Robert J. Kaiser, Bothell; Kevin P. Lund, Lynnwood, all of Wash.

[73] Assignee: Prolinx, Inc., Bothell, Wash.

[21] Appl. No.: 956,194

[22] Filed: Oct. 22, 1997

Related U.S. Application Data

[60] Division of Ser. No. 689,283, Aug. 5, 1996, which is a continuation-in-part of Ser. No. 188,531, Jan. 28, 1994, Pat. No. 5,594,151.

[51] Int. Cl.$^6$ .................... C07F 5/02; C07C 259/10
[52] U.S. Cl. ............ 530/396.1; 424/450; 530/345; 530/350; 530/391.7; 530/402; 530/409; 546/291; 546/292; 548/338.1; 548/542; 548/547; 558/288; 558/289; 558/6; 560/42; 560/315
[58] Field of Search .................... 530/391.1, 391.7, 530/349, 350, 402, 409; 424/450; 546/291, 292; 548/338.1, 542, 547; 560/42, 315; 562/627; 558/288, 289, 6

[56] References Cited

U.S. PATENT DOCUMENTS

| | | | |
|---|---|---|---|
| 2,548,257 | 7/1948 | Goldberg et al. | 562/453 |
| 4,269,605 | 5/1981 | Dean et al. | 436/67 |
| 4,281,181 | 7/1981 | Nagasawa et al. | 562/453 |
| 4,496,722 | 1/1985 | Gallop et al. | 544/69 |
| 4,713,346 | 12/1987 | Gallop et al. | 436/86 |
| 4,783,487 | 11/1988 | Brune | 514/563 |
| 4,851,443 | 7/1989 | Brune | 514/563 |
| 4,894,229 | 1/1990 | Polson et al. | 424/92 |
| 4,910,300 | 3/1990 | Urdea et al. | 536/287 |
| 5,002,883 | 3/1991 | Bieniarz et al. | 435/176 |
| 5,045,451 | 9/1991 | Uhr et al. | 435/6 |
| 5,093,232 | 3/1992 | Urdea et al. | 435/7.23 |
| 5,183,653 | 2/1993 | Linder et al. | 424/1.1 |

FOREIGN PATENT DOCUMENTS

| | | |
|---|---|---|
| 9013818 | 11/1990 | WIPO. |
| 9208722 | 5/1992 | WIPO. |
| 9420858 | 9/1994 | WIPO. |

OTHER PUBLICATIONS

Wilchek, M. & Bayer, E.A.; "Introduction to Avidin—Biotin Technology"; *Methods in Enzymology*; vol. 184; 1990 (USA).

Kessler et al.; "Non–radioactive Labeling and Detection of Nucleic Acids"; *Biol. Chem. Hoppe—Seyler*, vol. 371, pp. 917–927; 1990 (USA).

Singhal, R.P. & DeSilva, S.S.M.; "Boronate Affinity Chromatography"; *Advances in Chromatography*; vol. 31, pp. 293–335; 1992 (USA).

Mazzeo, J.R. & Krull, I.S.; "Immobilized Boronates for the Isolation and Separation of Bioanalytes"; *Biochromatography*; vol. 4, pp. 124–130; 1989.

Bergold, A. & Scouten, W.H.; "Borate Chromatography"; *Solid Phase Biochemistry*; Ch. 4, pp. 149–187;1983 (USA).

Lorand, J.P. & Edwards, J.O.;"Polyol Complexes and Structure of the Benzeneboronate Ion"; *J. Org. Chem.*; vol. 24, p. 769; 1959 (USA).

Bowie, R.A. & Musgrave, O.C.; "Organoboron Compounds. Part V. The Hydrolysis of Cyclic Phenylboronates"; *J. Amer. Chem. Soc.*; pp. 3945–3949; 1963 (USA).

Sienkiewicz, P.A. & Roberts, D.C.; "pH Dependence of Boronic Acid—Diol Affinity in Aqueous Solution"; *J. Iorg. Nucl. Chem*; vol. 42, pp. 1559–1571; 1980 (USA).

Tanner, D.W. & Bruice, T.C.; "Boric Acid Esters" *J. amer. Chem. Soc.*; vol. 89, pp. 6954–6971; 1967 (USA).

Kliegel, W. & Nanninga, D.; "Borchelate von Salicylaldoxim und Derivaten"; *Monatshefte Fur Chemie*; vol. 114, pp. 465–484; 1983 (FRG).

Imagawa et al.; "Characteristics and Evaluation of aantibody—Horseradish Perioxidase Conjugates, etc."; *J. Aplied Biochemistry*; vol. 4, pp.41–57; 1982 (USA).

Kessler, C.; *Advances in Mutagenesis Research* (Obe, G. ed.); pp. 105–152; Springer—Verlag, Berlin/Heidelberg; 1990 (USA).

(List continued on next page.)

*Primary Examiner*—Richard L. Raymond
*Attorney, Agent, or Firm*—Blakely, Sokoloff, Taylor & Zafman

[57] ABSTRACT

Boron compound complexing reagents, boron compound complexes, and methods of synthesizing these reagents and complexes are disclosed. These reagents and complexes include those shown in General Formula CIV, and General Formula CVI. In one embodiment, the reagent of General Formula CIV may be used to form a complex with a boron compound, such as a complex shown in General Formula CVI.

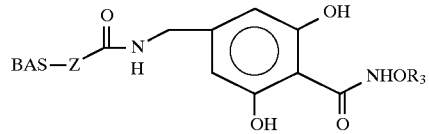

General Formula CIV

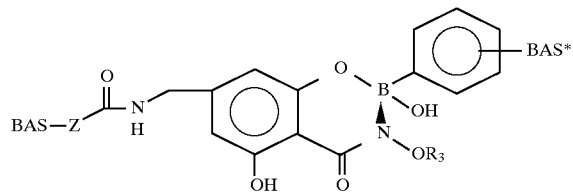

General Formula CVI

In one embodiment, group Z comprises a spacer selected from a saturated or unsaturated chain of up to about 6 carbon equivalents in length, an unbranched saturated or unsaturated chain of from about 6 to 18 carbon equivalents in length with at least one of intermediate amide and disulfide moieties, and a polyethylene glycol chain of from about 3 to 12 carbon equivalents in length; group $R_3$ is selected from one of an H, an alkyl, and a methylene or ethylene moiety with an electronegative substituent; and BAS and BAS* are biologically active species.

8 Claims, 7 Drawing Sheets

OTHER PUBLICATIONS

Brinkley, M.; "A Brief Survey of Methods for Preparing Protein Conjugates with Dyes, Haptens, and Cross Linking Reagents"; *Bioconjugate Chem.*; vol. 3, pp. 2–13; 1992 (USA).

Linder et al.; "Technetium Labeling of Monoclonal Antibodies with Functionalized BATOs 1.TcCI(DMG)$_3$PITC"; *Bioconjugate Chem.*; vol. 2, pp. 160–170; 1991 (USA).

Linder et al.;"Technetium Labeling of Monoclonal Antibodies with Functionalized BATOs 2. TcCI(DMG)$_3$CPITC Labeling of B72.3, etc." *Bioconjugate Chem.*; vol. 2, pp. 407–415; 1991 (USA).

Burnett et al.;"Synthesis of a Fluorescent Boronic Acid Which Reversibly Binds to Cell Walls, etc."; *Biochem, Biophys, Research Commun.*; vol. 96, pp. 157–162; 1980 (USA).

Steinberg, G.M. & Swidler, R.; "The Benzohydroxamate Anion"; *J. Org. Chem. Vol.*; vol. 30, pp 2362–2365; 1965 (USA).

Bauer, L. & Exner, O.; "The Chemistry of Hydroxamic Acids and N—Hydroxyimides"; *Angew. Chem. Internat. Edit.*l vol. 13, pp. 376–384; 1974 (USA).

Cai, S.X & Kean, J.;"o—Acetomidophenylboronate Esters Stabilized Toward Hydrolysis by an Intramolecular O—B Interation, etc."; *Bioconjugate Chem.*; vol. 2, pp 317–322; 1991 (USA).

Ramalingam, K. & Nowotnik, D.; "Syntheses of Some Isothiocyanatophenylboronic Acids"; *Org. Prep. Proc. Int.*; vol. 23, 729–34; 1991 (USA).

Kliegel, W. & Nanninga, D.; "Borchelate Von Salicyladehydnitronen"; *Journal of Organometallic Chem.*; vol. 243, pp 373–385; 1983 (USA).

Ripan et al.; "Etude Du Systeme Acide Borique—Salicylaldoxime en Solutions Aqueuses"; *Revue Roumaine de Chimie*; vol. 10, pp 965–171; 1965 (FRA).

Roberts et al.; "Pluripotential Amino Acids"; *Tetrahedron Letters*; vol. 21, pp. 3435–3438; 1980 (USA).

Kemp, D.S. & Roberts, D.;"New Protective Groups for Peptides Synthesis—II The DOBZ Group, etc."; *Tetrahedron Letters*; vol. 52, pp. 4629–4632; 1975 (USA).

Kliegel, W. & Nanninga, D.;"Borchelate von N—substituierten Hydroxamsauren"; *Chem. Ber.*; vol. 116,pp. 2616–2629; 1983 (FRG).

Mikesova, M. & Bartusek, M.;"Reaction of Boric Acid with Salicylic and Chromotropic Acids and with Their Derivatives"; *Chem. Zvesti*; vol. 32(4), pp. 472–477; 1978.

Feeney, R.E. "Chemical Modification of Proteins: Comments and Perspectives"; *Int. J. PeptideProtein Res.*; vol. 29, pp. 145–161 (USA), 1987.

Means, G.E. & Feeney, R.E; "Chemical Modifications of Proteins: History and Applications"; *Bioconjugate Chem.*; vol. 1, pp. 2–12 (USA), 1990.

O'Shannessy, D.J. & Quarles, R.H.; "Labeling of the Oligosaccharide Moieties of Immunoglobulins"; *J. Immunological Methods*; vol. 99, pp 153–161 (1987) (USA).

van't Reit, B., Wampler, G.L. & Elford, H.L.; "Synthesis of Hydroxy–and Amino—Substituted Benzohydroxamic Acids, etc."; *J. Medicinal Chem.*; vol. 22, No. 5, 589–92, 1979 (USA).

Soundararajan, et al.; "Boronic Acids for Affinity Chromatography: Spectral Methods for Determination, etc."; *Analytical Biochem.*; vol. 178, pp. 125–134, 1989 (USA).

Goodchild, J.; "Conjugates of Oligonucleotides and Modified Oligonucleotides: A Review of Their Synthesis and Properties"; *Bioconjugate Chem.*; vol. 1, No. 3, pp. 165–193, 1990 (USA).

Kessler, C.; *Nonradioactive Labeling and Detection of Biomolecules*; Ch. 1–3, 1992 (USA).

Meares, C.F., "Editorial: Introduction to Bioconjugate Chemistry"; *Bioconjugate Chem.*; vol. 1, No. 1, 1990 (USA).

Waggoner, A.S.; "Fluorescent Probes for Cytometry"; *Flow Cytometry and Sorting*; 2nd ed; pp. 209–225; 1990 (USA).

Borrebaeck, C.;"Strategy for the production of human monoclonal antibodies using in vitro activated B cells"; *J. Immun. Methods*; vol. 123; 157–65; 1989 (USA).

Chen, et al.; "Structure—Activity Relationships in a Series of 5 . [(2,5 . Dihydroxybenzyl)amino]salicylate, etc."; Chemical Abstracts; vol. 120; 322877v; 1994 (USA).

Hirano, et al.; "Silver halide color photographic material"; Chemical Abstracts; vol. 116; 140012u; 1992 (USA).

Kawasaki, et al.; "Silver halide photographic material with improved storage stability"; Chemical Abstracts; vol. 109; 160505r; 1988 (USA).

Priewe, H., et al.; "o–Hydroxybenzohydroxamic Acids"; Chemical Abstracts; vol. 52; 10184; 1958 (USA).

Regneir, G., et al., No. 473–"Acide—Phenols", Bulletin de la Societe Chimique de France 1966, No. 9, pp. 2821, 2827.

Meindl, W., et.; "Antimykobakterielle N—Alkalbenzylamine", Arch. Pharm., 315, 941–46 (1982).

Thompson, A.M., et al.; Tyrosine Kinase Inhibitors; Synthesis of 2,2' . Dithiobis (1H . indole . 3 . alkanamides) and Investigation of Their Inhibitory Activity against Epidermal Growth Factor Receptor and pp60$^{vs/c}$ Protein tyrosine Kinases, J. Med. Chem., 1994, 37, 598–609.

Quelet, r., et al., No. 303–"Chloromethylation de l'acide salicylique et des ethers phenoliques correspondants", Bulletinde la Societe Chimique de France, 1969, No. 5, pp. 1698–1705.

Malmberg, H. et al.; "Stereoselectivity in the transfer of the 2 . (1 . dimethylaminoethyl) phenyl group, R. from LiR$_2$Cu and Li(R) . (2 . thienyl)Cu to enones," Chem. Abstracts; vol.98;71593e;1982.

*Step 1*

*Step 2*

*Step 3*

*Step 4*

BORONIC COMPOUND COMPLEXING REAGENTS AND HIGHLY STABLE COMPLEXES

CROSS-REFERENCE TO RELATED APPLICATIONS

This is a divisional of application Ser. No. 08/689,283, filed Aug. 5, 1996, which is a continuation in part of U.S. application Ser. No. 08/188,531 which was filed on Jan. 28, 1994 and is now U.S. Pat. No. 5,594,151 and which is hereby incorporated herein by reference.

This application also follows applications U.S. Ser. Nos. 08/188,460 (now abandoned); 08/188,958 (now U.S. Pat. No. 5,594,111) and 08/189,176 (now U.S. Pat. No. 5,623,055), all filed Jan. 28, 1994 and each of which is incorporated herein by reference.

FIELD OF THE INVENTION

The present invention relates to the field of bioconjugate preparation, and more particularly, to a class of boronic compound complexing reagents useful for the conjugation of biological macromolecules, and the method of making and using such reagents.

BACKGROUND OF THE INVENTION

Bioconjugation is a descriptive term for the joining of two or more different molecular species by chemical or biological means, in which at least one of the molecular species is a biological macromolecule. This includes, but is not limited to, conjugation of proteins, peptides, polysaccharides, hormones, nucleic acids, liposomes and cells, with each other or with any other molecular species that add useful properties, including, but not limited to, drugs, radionuclides, toxins, haptens, inhibitors, chromophores, fluorophores, ligands, etc. Immobilization of biological macromolecules is also considered a special case of bioconjugation in which the macromolecule is conjugated, either reversibly or irreversibly, to an insoluble support. Bioconjugation is utilized extensively in biochemical, immunochemical and molecular biological research. Major applications of bioconjugation include; detection of gene probes, enzyme-linked immuno solid-phase assay, monoclonal antibody drug targeting and medical imaging.

Bioconjugates are generally classified as either direct or indirect conjugates. Direct conjugates encompass those in which two or more components are joined by direct covalent chemical linkages. Alternatively, indirect conjugates encompass those in which two or more components are joined via an intermediary complex involving a biological macromolecule. The system described herein is the first to enable the formation of indirect conjugates without dependence upon an intermediary biological macromolecule.

AVIDIN-BIOTIN SYSTEM

Although numerous methods of indirect bioconjugate preparation have been described, a significant number of those reported in the literature have been prepared by exploiting the Avidin-Biotin system, in which, the binding specificity of the protein Avidin (purified from egg white), or Streptavidin (purified from the bacterium *Streptomyces avidinii*), toward the cofactor Biotin (vitamin H) is utilized to bridge an Avidin conjugated macromolecule with a biotinylated macromolecule. Both Avidin and Streptavidin possess four Biotin binding sites of very high affinity ($K=10^{15}$ $mol^{-1}$).

The Avidin-Biotin system has been utilized extensively for enzyme-linked immuno solid-phase assay (ELISA), in which an enzyme-Avidin conjugate (useful for detection by reaction with the enzyme's substrate to afford a colored or chemiluminescent product) is employed to detect the presence of a biotinylated antibody, after first binding the antibody to an immobilized antigen or hapten. Applications of the Avidin-Biotin system number in the hundreds, and have recently been reviewed (Wilchek, M. and Bayer, E. A., (1990) *Methods in Enzymology*, 184). Although utilized extensively, several limitations are known to be associated with the Avidin-Biotin system, which include nonspecific binding generally attributed to the basicity of the Avidin molecule, nonspecific binding attributed to the presence of carbohydrate residues on the Avidin molecule, and background interference associated with the presence of endogenous Biotin, which is ubiquitous in both eukaryotic and prokaryotic cells.

DIGOXIGENIN α-DIGOXIGENIN SYSTEM

An alternative indirect bioconjugation system designed to overcome some of the limitations associated with the Avidin-Biotin system has recently been developed for the detection of gene probes by ELISA (Kessler, C., Hôltke, H.-J., Seibl, R., Burg, J. and Mühlegger, K., (1990) *Biol. Chem.* Hoppe-Seyler, 371, 917–965. This system involves the use of the steroid hapten Digoxigenin, an alkaloid occuring exclusively in Digitalis plants, and Fab fragments derived from polyclonal sheep antibodies against Digoxigenin (α-Digoxigenin). The high specificity of the various α-Digoxigenin antibodies affords low backgrounds and eliminates the non-specific binding observed in Avidin-Biotin systems. Digoxigenin-labeled DNA and RNA probes can detect single-copy sequences in human genomic Southern blots. The development of the Digoxigenin α-Digoxigenin system has recently been reviewed (Kessler, C. (1990) in Advances in Mutagenesis Research (Obe, G. ed.) pp. 105–152, Springer-Verlag, Berlin/Heidelberg). The Digoxigenin α-Digoxigenin system is the most recent representative of several hapten-antibody systems now utilized for bioconjugation.

IMMOBILIZED PHENYLBORONATES

Phenylboronic acids are known to interact with a wide range of polar molecules having certain requisite functionalities. Complexes of varying stability, involving 1,2-diols, 1,3-diols, 1,2-hydroxy acids, 1,3-hydroxy acids, 1,2-hydroxylamines, 1,3-hydroxylamines, 1,2-diketones and 1,3-diketones, are known to form with either neutral phenylboronic acid or phenylboronate anion. Consequently, immobilize phenylboronic acids have been exploited as chromatographic supports to selectively retain, from diverse biological samples, those molecular species having the requisite functionalities. Many important biological molecules including carbohydrates, catecholamines, prostaglandins, ribonucleosides, and steroids contain the requisite functionalities, and have been either analyzed or purified in this manner. The use of phenylboronic acid chromatographic media for the isolation and separation of biological molecules has been discussed in several reviews (Singhal, R. P. and DeSilva, S. S. M. (1992) *Adv. Chromatog.*, 31, 293–335; Mazzeo, J. R. and Krull, I. S. (1989) *BioChromatog.*, 4, 124–130; and Bergold, A. and Scouten, W. H. (1983) in Solid Phase Biochemistry (Scouten, W. H. ed.) pp. 149–187, John Wiley & Sons, New York ).

Phenylboronic acid, like boric acid, is a Lewis acid, and ionizes not by direct deprotonation, but by hydration to give the tetrahedral phenylboronate anion ($pK_a$=8.86). Phenylboronic acid is three times as strong an acid as boric acid. Ionization of phenylboronic acid is an important factor in complex formation, in that, upon ionization, boron changes from trigonal coordination (having average bond angles of 120° and average bond lengths of 1.37≈) to the tetrahedrally coordinated anion (having average bond angles of 109° and average bond lengths of 1.48≈).

Molecular species having cis or coaxial 1,2-diol and 1,3-diol functionalities, and particularly carbohydrates, are known to complex with immobilized phenylboronate anion, to form cyclic esters under alkaline aqueous conditions (Lorand, J. P. and Edwards, J. O. (1959) *J. Org. Chem.*, 24, 769).

Acidification of 1,2-diol and 1,3-diol complexes to neutral pH is know to release the diol containing species, presumably due to hydrolysis of the cyclic ester. Coplanar aromatic 1,3-diols, like 1,8-dihydroxynaphthalene, are known to complex even under acidic conditions due to the hydrolytic stability of six-membered cyclic boronic acid esters (Sienkiewicz, P. A. and Roberts, D. C. (1980) *J. Inorg. Nucl. Chem.*, 42, 1559–1571). Molecular species having pendant 1,2-hydroxylamine, 1,3-hydroxylamine, 1,2-hydroxyamide, 1,3-hydroxyamide, 1,2-hydroxy-oxime and 1,3-hydroxyoxime functionalities are also known to reversibly complex with phenylboronic acid under alkaline aqueous conditions similar to those associated with the retention of diol containing species (Tanner, D. W. and Bruice, T. C. (1967) *J. Amer. Chem. Soc.*, 89, 6954).

PHENYLBORONATE BIOCONJUGATES

Ortho-substituted acetamidophenylboronic acids have been proposed as potential linkers for selective bioconjugation via the vicinal diol moieties of the carbohydrate residues associated with glycoproteins (Cai, S. X. and Keana, J. F. W. (1991) *Bioconjugate Chem.*, 2, 317–322).

Phenylboronic acid bioconjugates derived from 3-isothiocyanatophenylboronic acid have been successfully utilized for appending radioactive technetium dioxime complexes to monoclonal antibodies for use in medical imaging (Linder, K. E., Wen, M. D., Nowotnik, D. P., Malley, M. F., Gougoutas, J. Z., Nunn, A. D. and Eckelman, W. C. (1991) *Bioconjugate Chem.*, 2, 160–170; Linder, K. E., Wen, M. D., Nowotnik, D. P., Ramalingam, K., Sharkey, R. M., Yost, F., Narra, R. K. and Eckelman, W. C. (1991) *Bioconjugate Chem.*, 2, 407–414).

3-Aminophenylboronic acid has been covalently appended to proteins by a variety of chemical methods and the resulting phenylboronic acid bioconjugates tested for their binding of D-sorbitol, D-mannose and glycated hemoglobin (GHb). The interactions proved to be reversible and of very low affinity rendering the bioconjugates of very limited practical use. Similarly, an alkaline phosphatase phenylboronic acid bioconjugate used in an attempted enzyme-linked assay for the detection of GHb failed to detect the presence of glycated protein (Frantzen, F., Grimsrud, K., Heggli, D. and Sundrehagen, E. (1995) *Journal of Chromatography B*, 670, 37–45).

Although immobilized phenylboronates have been utilized for chromatographic separation of biological molecules having the requisite functionalities, notwithstanding the substantial amount of research into bioconjugation, and the substantial amount of investment in this field, the selectivity of phenylboronic acid has not heretofore been successfully exploited to enable the conjugation of biological macromolecules with one another or with other molecular species that add useful properties.

SUMMARY OF THE INVENTION

The present invention relates to a novel class of boron compound complexing reagents useful for the preparation of bioconjugates, and the method of making and using such reagents. In one embodiment, the boron compound is phenylboronic acid, or derivatives thereof, which complex with the complexing reagents of the present invention. Unless otherwise noted, the phrase phenylboronic acid complexing reagent is used herein to include the broader class of boron compound complexing reagents, and the phrase phenylboronic acid is used herein to include the broader class of boron compounds which complex with the boron compound complexing reagents. In the present invention, in the place of prior art Avidin-Biotin and Digoxigenin α-Digoxigenin systems, boron compound complexing reagents are utilized in conjunction with the boron compound, such as phenylboronic acid reagents (many of which are known in the prior art) to facilitate chemical conjugation without the use of intermediary biological macromolecules. Bioconjugate preparation often involves the conjugation of several components including, but not limited to, proteins, peptides, polysaccharides, hormones, nucleic acids, liposomes and cells, with each other or with any other molecular species that add useful properties, including, but not limited to, drugs, radionuclides, toxins, haptens, inhibitors, fluorophores, ligands, solid-phase supports, and boron compound complexing reagents conjugates. These various components utilized in bioconjugate preparation will collectively and individually be termed biologically active species or bioactive species.

Reagents suitable for the modification of a bioactive species for the purpose of incorporating a phenylboronic acid complexing moiety for subsequent conjugation to a different (or the same) bioactive species having pendant phenylboronic acid moieties are of the general formula of General Formula CIII:

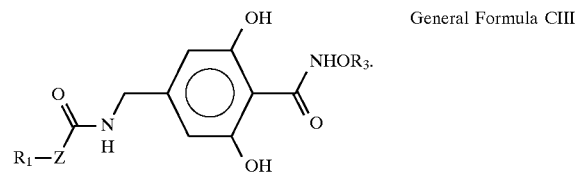

General Formula CIII

Group $R_1$ is a reactive electrophilic or nucleophilic moiety suitable for reaction of the phenylboronic acid complexing reagent with a bioactive species. Group Z is a spacer selected from a saturated or unsaturated chain of from about 0 to 6 carbon equivalents in length, an unbranched saturated or unsaturated chain of from about 6 to 18 carbon equivalents in length with at least one of intermediate amide or disulfide moieties, and a polyethylene glycol chain of from about 3 to 12 carbon equivalents in length. Group $R_3$ is selected from one of an H, an alkyl, and a methylene or ethylene moiety with an electronegative substituent.

Group $R_3$ is preferably selected from one of H, $CH_3$, $CH_2CN$, $CH_2COOH$, $CH_2CONH_2$, $CH_2CH_2OH$ and $CH_2OCH_3$. When group $R_3$ is H, group $R_1$ is preferably selected from one of acrylamide, amino, dithiopyridyl, hydrazide, imidate ester, maleimide, and thiol moieties. Group Z is preferably an unbranched alkyl chain of the general formula $(CH_2)_n$, wherein n=1 to 6.

Reaction of a reagent of General Formula CIII with a bioactive species affords a conjugate having pendant phenylboronic acid complexing moieties (one or more) of General Formula CIV, General Formula CIV

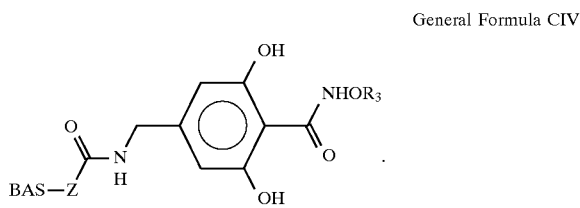

The symbol labeled BAS represents a biologically active species (or bioactive species) that may or may not contain a portion of a reactive moiety (which may itself have a spacer) used to attach the bioactive species to the reagent. It will be appreciated that, in many embodiments, several identical reagents of the general formula of General Formula CIII will react with a single BAS molecule. For example, if the BAS is a protein, many phenylboronic acid complexing reagents will react with the protein, each reacting at one of the several sites on the protein which are reactive with the $R_1$ group. Group Z in General Formula CIV is a spacer selected from a saturated or unsaturated chain of from about 0 to 6 carbon equivalents in length, an unbranched saturated or unsaturated chain of from about 6 to 18 carbon equivalents in length with at least one of intermediate amide or disulfide moieties, and a polyethylene glycol chain of from about 3 to 12 carbon equivalents in length. Group $R_3$ is selected from one of an H, an alkyl, and a methylene or ethylene moiety with an electronegative substituent.

The compositions of General Formulas CI and CII, and methods for their preparations are described herein and are the subject of my copending applications, titled Boronic Compound Complexing Reagents and Highly Stable Complexes, U.S. Ser. No. 08/691,930 and filed on Aug. 5, 1996 by Mark L. Stolowitz, Robert J. Kaiser, and Kevin P. Lund, and U.S. Ser. No. 08/956,196, which copending applications are hereby incorporated herein by reference.

Phenylboronic acid reagents, many of which are known in the prior art, as well as those described in greater detail in my copending application, titled Phenlyboronic Acid Complexes For Bioconjugate Preparation, and filed on Jan. 28, 1994 U.S. Pat. No. 5,594,111, which is incorporated herein by reference, may be appended to a biologically active species to afford a conjugate having pendant phenylboronic acid moieties (one or more) of General Formula CV:

General Formula CV

wherein the symbol labeled BAS* represents a second bioactive species, that may include a linker portion and that may differ from the bioactive species labeled BAS. The BAS* may also include a portion of a reactive moiety used to attach the bioactive species to the phenylboronic acid reagent.

A conjugate of General Formula CIV, with at least one biologically active species and having pendent phenylboronic acid complexing moieties (one or more), may be complexed with a conjugate of General Formula CV, prepared from a second bioactive species BAS* and having pendant phenylboronic acid moieties (one or more), to afford a bioconjugate of General Formula CVI, General Formula CVI

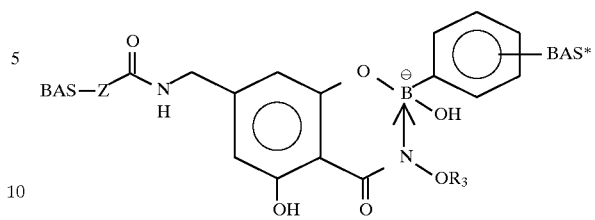

wherein the symbols labeled BAS and BAS*, and groups Z and $R_3$ are as were previously defined. In this manner, as summarized in FIG. 1', biological macromolecules may be conjugated to one another or with other functionalities which impart useful properties.

Bioconjugates of General Formula CVI may be prepared in buffered aqueous solution or organic solvents. The bioconjugate is formed within a few minutes over a range of temperatures of from about 4° C. to 7° C. The stability of the bioconjugate in aqueous solution at a given pH and temperature is significantly influenced by substituent group $R_3$. Bioconjugates of General Formula CVI, are stable in aqueous solutions of approximate pH greater than 2.5 and less than 12.5. The bioconjugation reaction (phenylboronic acid complexation) is insensitive to significant variations in ionic strength, the presence of organic solvents, the presence of detergents, and the presence of chaotropic agents (protein denaturants), which are incompatible with prior art indirect labeling systems wherein the structure of a biological macromolecule must be maintained to preserve requisite binding properties. In most instances, the constraints governing the formation of bioconjugates, by the system herein described, are limited to those imposed by the conditions required to maintain viability of the bioactive species.

In summary, boron compound complexing reagents, intermediate reagents of these reagents, boron compound complexes, and methods of synthesizing these reagents and complexes are described. These reagents and complexes include those shown in General Formula CIII, CIV and CVI. In one embodiment, the reagent of General Formula CIII may be used to produce, after condensation with a bioactive species (BAS), the reagent of General Formula CIV. The reagent of General Formula CIV may be used to form a complex with a boron compound, such as a complex shown in General Formula CVI.

BRIEF DESCRIPTION OF THE FIGURES

FIG. 1' illustrates the utilization of putative phenylboronic acid complexing reagents of General Formula CI and phenylboronic acid complexing reagents of General Formula CIII, to prepare conjugates of General Formula CIV which may, in turn, be utilized to prepare bioconjugates of General Formula CVI.

FIG. 2' summarizes the preparation of alkyl 4-aminomethyl-2,6-dihydroxybenzoates, synthetic intermediates leading to reagents of General Formula CI, wherein R₂ is an alkyl group, e.g., methyl, ethyl, propyl, etc. Alkyl 4-aminomethyl-2,6-dihydroxybenzoates are also useful synthetic intermediates leading to reagents of General Formula CIII.

FIG. 3' summarizes the preparation of alkyl 4-aminomethyl-2,6-dihydroxybenzoates, synthetic intermediates leading to reagents of General Formula CI, wherein R₂ is a methylene group bearing an electronegative moiety, e.g., carboxymethyl, cyanomethyl, methoxymethyl, etc.

FIG. 4' summarizes the preparation of 4-aminomethyl-2, 6-dihydroxybenzohydroxamic acids, synthetic intermediates leading to reagents of General Formula cm, wherein R₃ is one of either an alkyl group or a methylene or ethylene group bearing an electronegative moiety.

FIG. 5' summarizes the synthesis of reagents of General Formulas CI and CIII, wherein R₂ is one of either an alkyl group or a methylene group bearing an electronegative moiety, and wherein R₁ is selected from either imidazolide, hydrazide and N-hydroxysuccinimidyl ester moieties.

FIG. 6' summarizes the synthesis of reagents of General Formulas CI and CIII, wherein R₂ is one of either an alkyl group or a methylene group bearing an electronegative moiety, and wherein R₁ is selected from either bromo, chloro, iodo, maleimide, dithiopyridyl and imidate ester moieties.

FIG. 7' summarizes the synthesis of reagents of General Formulas CI and CIII, wherein R₁ is an N-hydroxysuccinimidy ester, and wherein Z an unbranched saturated or unsaturated chain of from about 6 to 18 carbon equivalents in length with at least one of either an intermediate amide or disulfide moiety.

DETAILED DESCRIPTION OF THE INVENTION

PHENYLBORONIC ACID COMPLEXING REAGENTS AND CONJUGATES DERIVED FROM 4- OR 5-AMINOMETHYLSALICYLIC ACID

This section relates to a class of phenylboronic acid complexing reagents and conjugates derived from 4- or 5-aminomethylsalicylic acid. Reagents and conjugates derived from 4- or 5-aminomethylsalicylic acid are the subject of my copending applications titled Boronic Compound Complexing Reagents and Complexes filed Aug. 5, 1996, Ser. No. 08/689,341 and application titled Boronic Compound Complexing Reagents and Complexes filed Aug. 5, 1996, Ser. No. 08/691,929. The discussion of the preparation of these compounds herein is to facilitate the overall understanding of the distinct and novel invention described herein. By presenting the preparation of various compounds from a similar family of complexing reagents and conjugates, it is intended that the full scope of the claimed invention is recognized.

Figure 1:
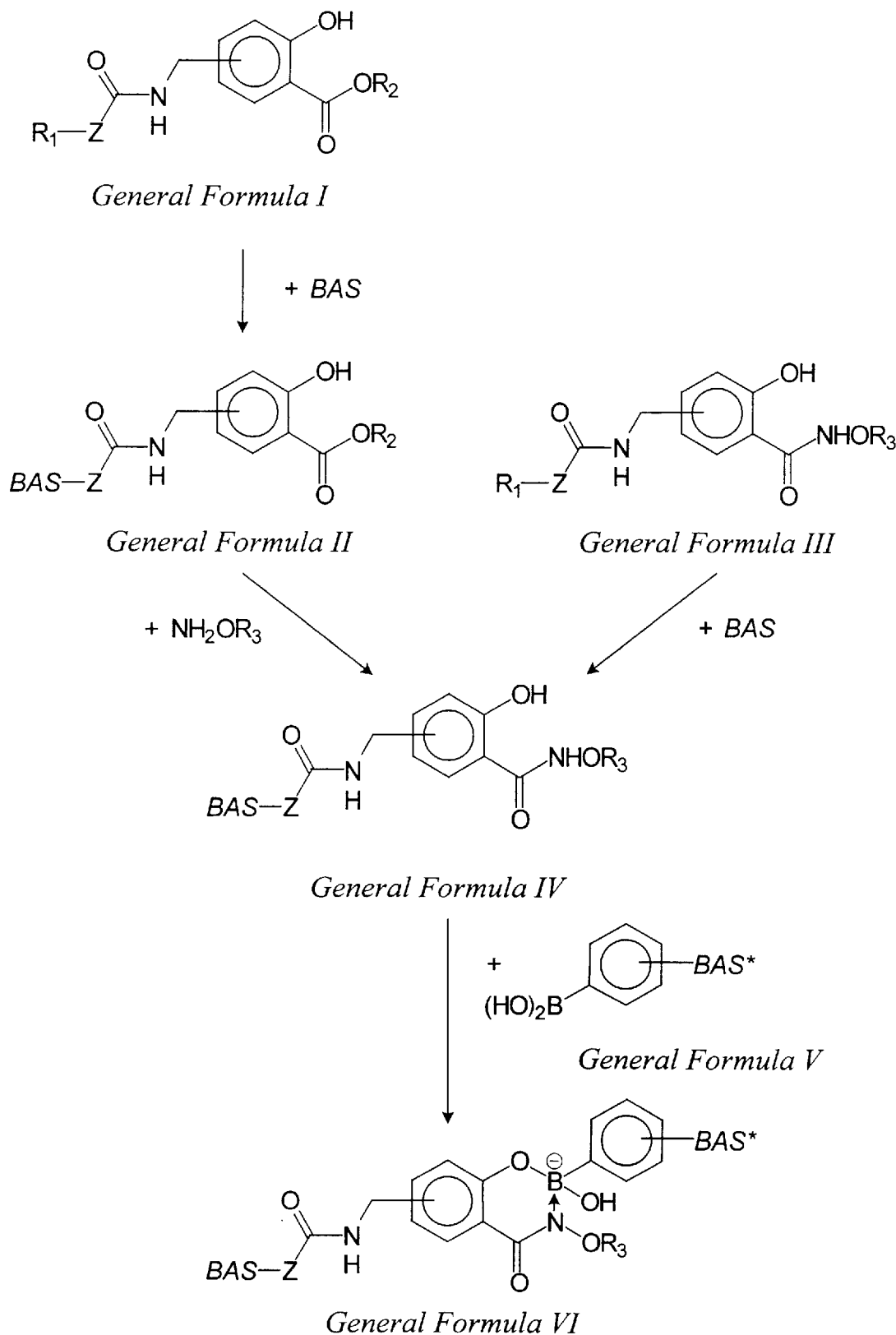
FIG. 1 illustrates the utilization of putative phenylboronic acid complexing reagents of General Formula I and phenylboronic acid complexing reagents of General Formula III, to prepare conjugates of General Formula IV which may, in turn, be utilized to prepare bioconjugates of General Formula VI.

A two-step process which utilizes reagents of General Formula III for the preparation of bioconjugates is summarized in FIG. 1. Initially, a reagent of General Formula III is selected that is comprised of an appropriate reactive electrophilic or nucleophic group R₁ suitable for reaction with the desired biologically active species.

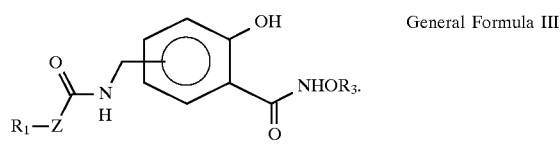

General Formula III

Group R₁ is a reactive electrophilic or nucleophilic moiety suitable for reaction of the phenylboronic acid complexing reagent with a bioactive species. Group R₁ is preferably selected from, but not limited to, acrylamide, bromo, dithiopyridyl, bromoacetamide, hydrazide, N-hydroxysuccinimidyl ester, N-hydroxysulfosuccinimidyl ester, imidate ester, imidazolide, iodo, iodoacetamide, maleimide, amino and thiol moieties.

Group Z is a spacer selected from a saturated or unsaturated, preferably unbranched, chain of from about 0 to 6 carbon equivalents in length, an unbranched saturated or unsaturated chain of from about 6 to 18 carbon equivalents in length with at least one of intermediate amide or disulfide moieties, and a polyethylene glycol chain of from about 3 to 12 carbon equivalents in length. Group Z is preferably selected from an unbranched alkyl chain of general formula $(CH_2)_n$, wherein n=1 to 6.

Group R₃ is selected from one of an H, an alkyl, and a methylene or ethylene moiety with an electronegative substituent.

Group R₃ is preferably selected from one of H, $CH_3$, $CH_2CN$, $CH_2COOH$, $CH_2CONH2$, $CH_2CH_2OH$ and $CH_2OCH_3$. When group R₃ is H, group R₁ is preferably selected from one of acrylamide, amino, dithiopyridyl, hydrazide, imidate ester, maleimide, and thiol moieties.

The reagent of General Formula III is condensed with the bioactive species to yield a conjugate of General Formula IV:

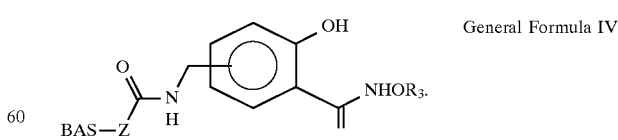

General Formula IV wherein groups Z and BAS are as defined above, and R₃ is selected from one of an H, an alkyl, and a methylene or ethylene moiety with an electronegative substituent.

The conjugate of General Formula IV is then complexed with a phenylboronic acid conjugate having the general formula of General Formula V:

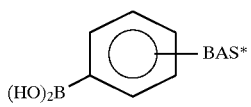

General Formula V wherein the symbol labeled BAS* represents a second biologically active species, that may include a linker portion and differ from the biologically active species labeled BAS of the complexing reagent. The BAS* may also include a portion of a reactive moiety used to attach the bioactive species to the phenylboronic acid reagent. The complexation yields the stereoisomeric complex (tetrahedral boron) of General Formula VI:

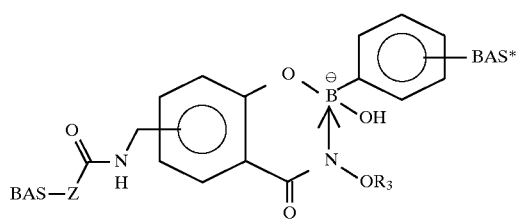

General Formula VI

An alternative three-step process which utilizes reagents of General Formula I for the preparation of bioconjugates is also summarized in FIG. 1. Initially, a reagent of General Formula I is selected that is comprised of an appropriate reactive electrophilic or nucleophic group $R_1$ suitable for reaction with the desired biologically active species.

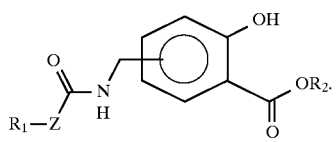

General Formula I

Group $R_1$ is a reactive electrophilic or nucleophilic moiety suitable for reaction of the putative phenylboronic acid complexing reagent with a bioactive species. Group $R_1$ is preferably selected from, but not limited to, acrylamide, bromo, dithiopyridyl, bromoacetamide, hydrazide, N-hydroxysuccinimidyl ester, N-hydroxysulfosuccinimidyl ester, imidate ester, imidazolide, iodo, iodoacetamide, maleimide, amino and thiol moieties.

Group Z is a spacer selected from a saturated or unsaturated, preferably unbranched, chain of from about 0 to 6 carbon equivalents in length, an unbranched saturated or unsaturated chain of from about 6 to 18 carbon equivalents in length with at least one of intermediate amide or disulfide moieties, and a polyethylene glycol chain of from about 3 to 12 carbon equivalents in length. Group Z is preferably selected from an unbranched alkyl chain of general formula $(CH_2)_n$, wherein n=1 to 6.

Group $R_2$ is selected from an alkyl (e.g., methyl, ethyl, etc.) and a methylene or ethylene bearing an electronegative substituent. An electronegative substituent is a substituent with a negative dipole moment, e.g., CN, COOH, etc. Group $R_2$ is preferably selected from one of $CH_3$, $CH_2CH_3$, $CH_2CN$, $CH_2COOH$, $CH_2CONH_2$ and $CH_2OCH_3$.

The next step in a three-step process in the preparation of bioconjugates is to condense the appropriate reagent with the bioactive species to yield a conjugate of General Formula II:

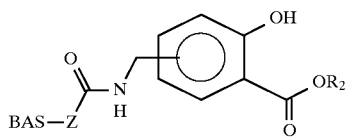

General Formula II

In General Formula II, Z, BAS and $R_2$ are as defined above.

Next, the conjugate is reacted with a hydroxylamine derivative of the general formula $NH_2OR_3$, wherein $R_3$ is selected from either an H, an alkyl (e.g., methyl, ethyl, etc.), or a methylene or ethylene with an electronegative substituent. Suitable hydroxylamine derivatives include, but not limited to, $NH_2OH$, $NH_2OCH_3$, $NH_2OCH_2CN$, $NH_2OCH_2COOH$, $NH_2OCH_2CONH_2$ and $NH_2OCH_2CH_2OH$. The resulting conjugate has the general formula of General Formula IV:

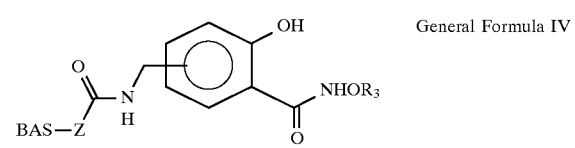

General Formula IV wherein groups Z and BAS are as defined above, and $R_3$ is selected from one of an H, an alkyl, and a methylene or ethylene moiety with an electronegative substituent.

The conjugate of General Formula IV is then complexed with a phenylboronic acid having the general formula of General Formula V:

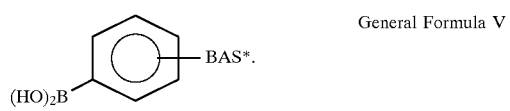

General Formula V wherein the symbol labeled BAS* represents a second biologically active species, that may include a linker portion and differ from the biologically active species labeled BAS of the complexing reagent. The BAS* may also include a portion of a reactive moiety used to attach the bioactive species to the phenylboronic acid reagent. The complexation yields the stereoisomeric complex (tetrahedral boron) of General Formula VI:

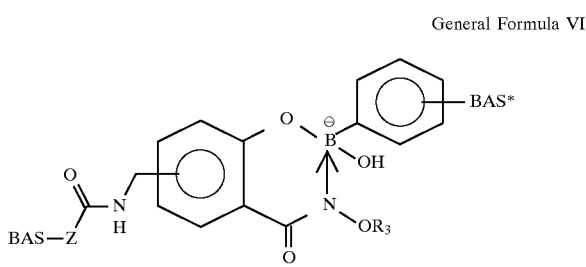

General Formula VI

SYNTHESIS OF PHENYLBORONIC ACID COMPLEXING REAGENTS OF GENERAL FORMULA III

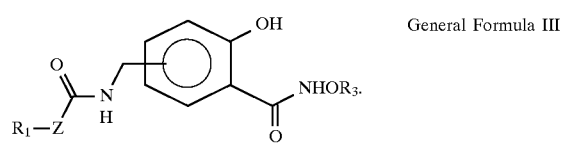

General Formula III

Reagents of General Formula m are derived from either 4- or 5-methylsalicylic acid. In each instance, the reagent is ultimately prepared from a synthetic intermediate which is either an alkyl 4- or 5-aminomethylbenzoate.

Figure 2:
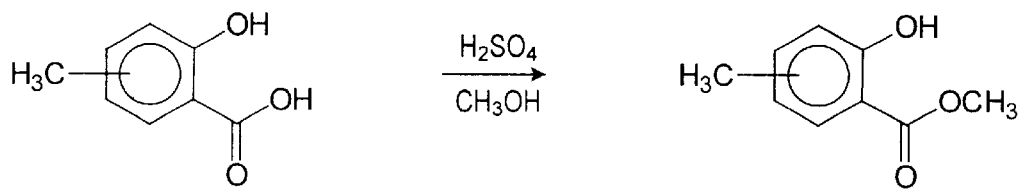
FIG. 2 summarizes the preparation of alkyl 4- and 5-aminomethylsalicylates, synthetic intermediates leading to reagents of General Formula I, wherein $R_2$ is an alkyl group, e.g., methyl, ethyl, propyl, etc. Alkyl 4- and 5-aminomethylsalicylates are also useful synthetic intermediates leading to reagents of General Formula III.
Figure 2:
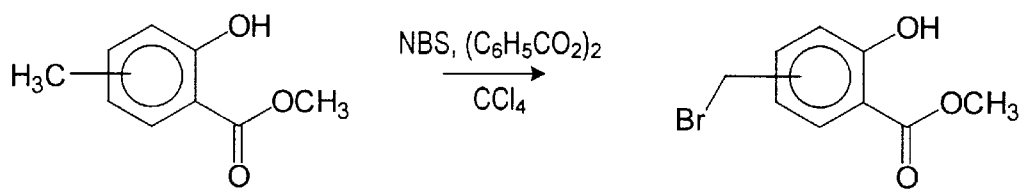
Figure 2:
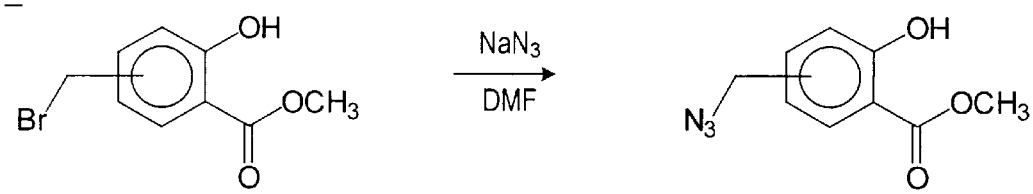
Figure 2:
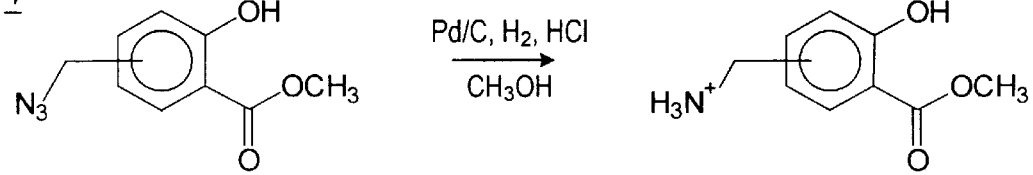

FIG. 2 summarizes the preparation of alkyl 4- and 5-aminomethylsalicylates, synthetic intermediates leading to reagents of General Formula III, wherein $R_2$ is an alkyl group, e.g., methyl, ethyl, etc. FIG. 2 shows an example where $R_2$ is a methyl group. Initially, in step 1, either 4- or 5-methylsalicylic acid is esterified to afford the corresponding alkyl 4- or 5-methylsalicylate. In step 2, the ester is brominated with N-bromo-succinimide and benzoyl peroxide catalyst to afford the corresponding benzyl bromide. In step 3, the benzyl bromide is alkylated with sodium azide to afford the corresponding benzyl azide. Finally, in step 4, the benzyl azide is subjected to palladium catalyzed hydrogenation in the presence of HCl to afford the corresponding benzyl amine hydrochloride.

Figure 4:
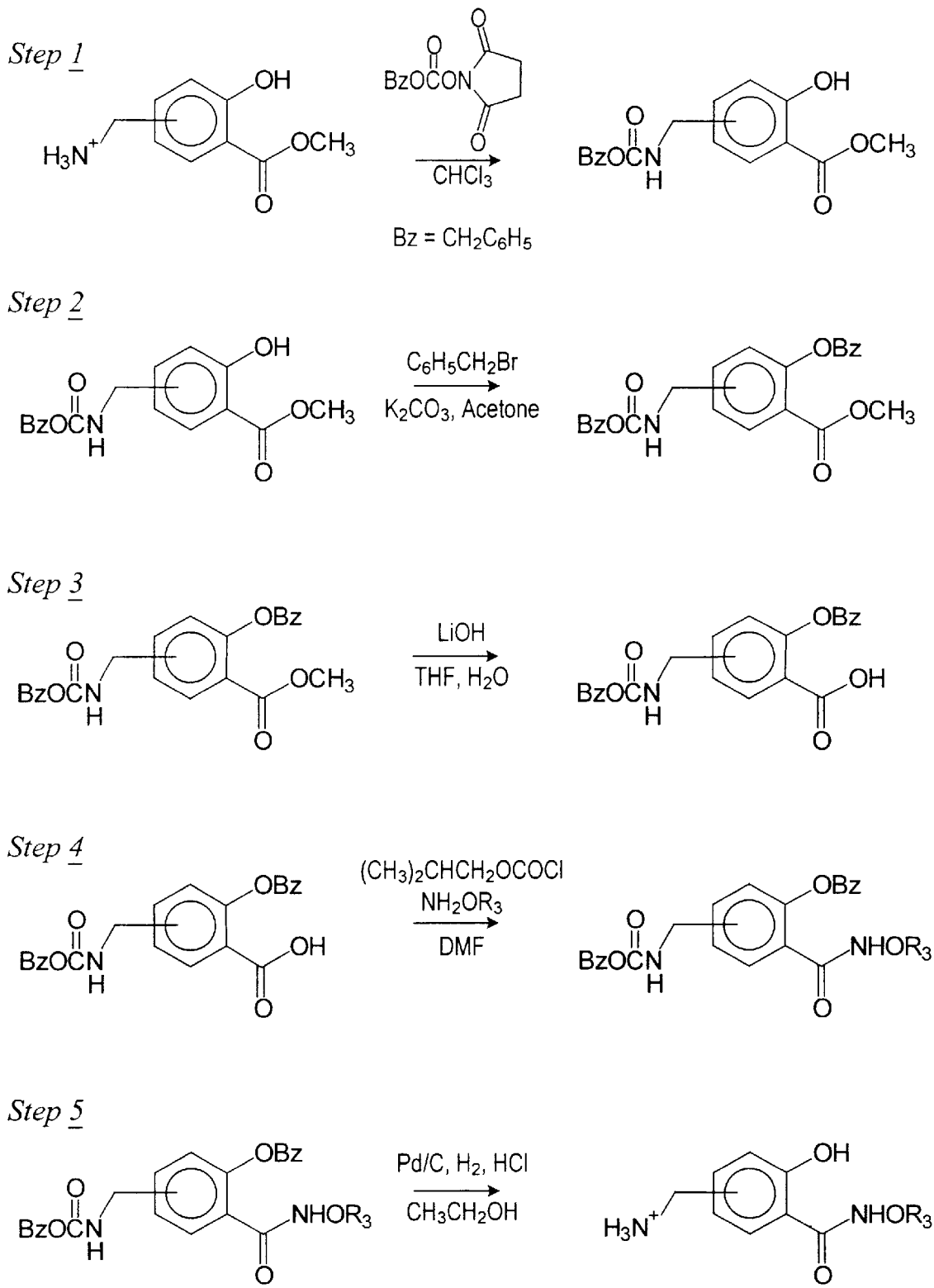
FIG. 4 summarizes the preparation of 4- and 5-aminomethylsalicylhydroxamic acids, synthetic intermediates leading to reagents of General Formula III, wherein R₃ is one of either an alkyl group or a methylene or ethylene group bearing an electronegative moiety.

FIG. 4 summarizes the preparation of 4- and 5-aminomethylsalicylhydroxamic acids, synthetic intermediates leading to reagents of General Formula III, wherein group $R_3$ is one of an alkyl or methylene or ethylene bearing an electronegative substituent. Initially, in step 1, an alkyl 4- or 5-aminomethylsalicylate, prepared as summarized in FIG. 2, is condensed with N-(benzyloxycarbonyl)oxy succinimide to afford the alkyl N-benzyloxycarbonyl protected 4- or 5-aminomethylsalicylate. In step 2, the phenolic hydroxyl moiety was condensed with benzyl bromide to afford the further protected benzyl ether intermediate. In step 3, the alkyl ester is selectively cleaved by reaction with LiOH to afford the corresponding benzoic acid. In step 4, the benzoic acid is activated by reaction with isobutylchloroformate to form a mixed anhydride which is subsequently reacted with a hydroxylamine derivative preferably selected from, but not limited to, either $NH_2OH$, $NH_2OCH_3$, $NH_2OCH_2CN$, $NH_2OCH_2COOH$, $NH_2OCH_2CONH_2$, $NH_2OCH_2CH_2OH$ and $NH_2OCH_2OCH_3$ to afford the corresponding protected hydroxamic acid. Finally, in step 5, both the amine and phenolic hydroxyl moieties are simultaneously deprotected by palladium catalyzed hydrogenation in the presence of HCl to afford the corresponding 4- or 5-aminomethylsalicylhydroxamic acid hydrochloride.

Another reagent of the present invention, which is the acrylic acid amide of aminomethylsalicylhydroxamic acid, can be prepared in a single step, using the end product of FIG. 4 by condensing acrylic acid anhydride or acryloyl chloride with aminomethyl-salicylhydroxamic acid, provided that $R_3$ is not H.

Figure 5:
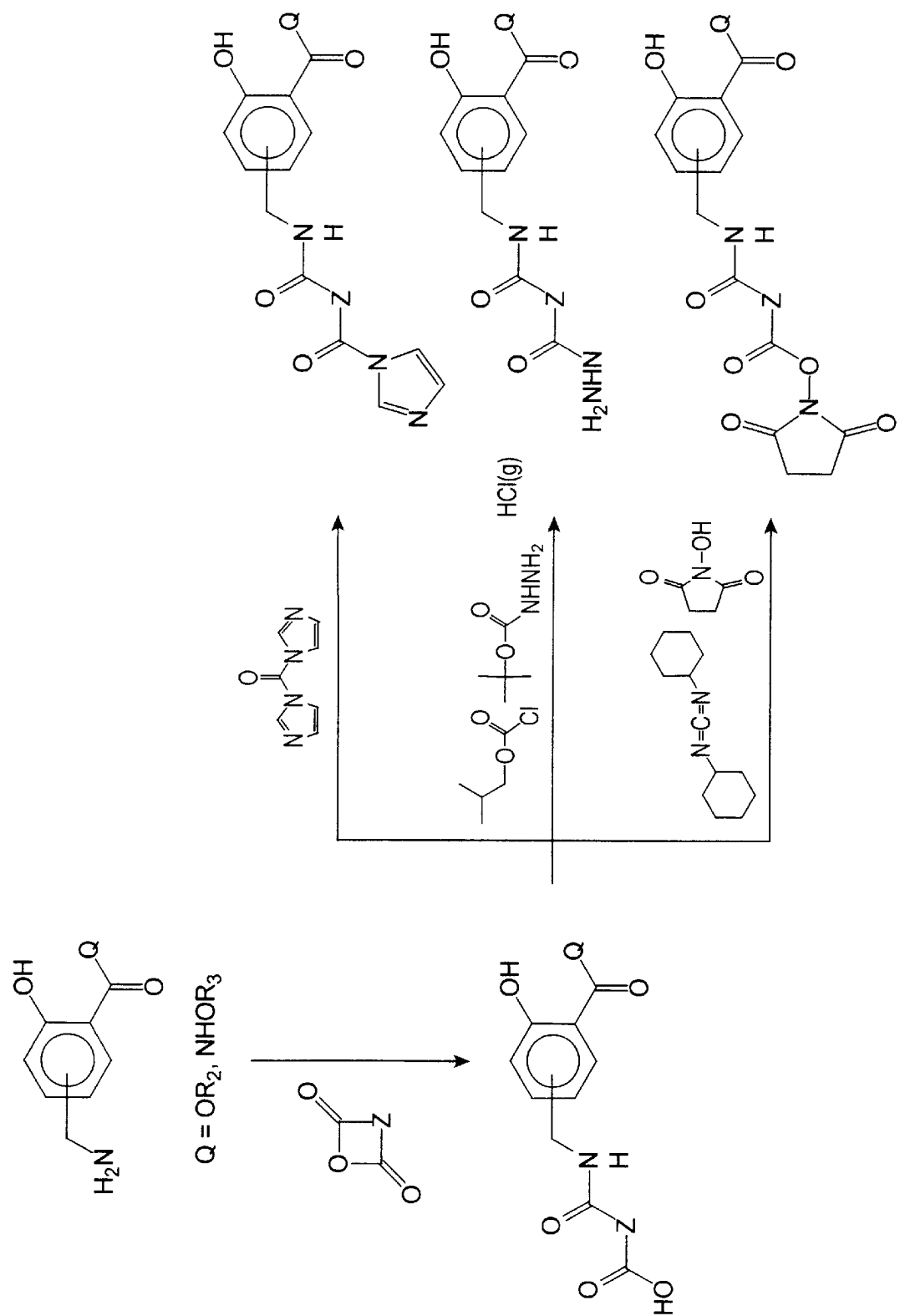
FIG. 5 summarizes the synthesis of reagents of General Formulas I and III, wherein R₂ is one of either an alkyl group or a methylene group bearing an electronegative moiety, and wherein R₁ is selected from either imidazolide, hydrazide and N-hydroxysuccinimidyl ester moieties.

FIG. 5 summarizes the synthesis of reagents of General Formula III, wherein group $R_3$ is preferably selected from one of H, $CH_3$, and a methylene or ethylene moiety with an electronegative substituent, and wherein group $R_1$ is selected from either imidazolide, hydrazide and N-hydroxysuccinimidyl ester moieties. These reagents are each prepared by a two-step process in which an aliphatic acid anhydride is utilized in the first step. Initially, a 4- or 5-aminomethylsalicylhydroxamic acid, prepared as summarized in FIG. 4, is condensed of an aliphatic acid anhydride preferably selected from, but not limited to, either succinic anhydride, glutaric anhydride, maleic anhydride and glycolic acid anhydride, in an aprotic organic solvent, which results in the introduction of a spacer (group Z) having a free terminal carboxylic acid moiety. In the case where the aliphatic acid anhydride is maleic anhydride in this condensation reaction, the resulting Z group is unsaturated as it contains an alkene group. Subsequently, the carboxylic acid moiety is further functionalized by reaction with either N,N-carbonyl-diimidazole, isobutylchloroformate and tert-butyl carbazate, or N,N-dicyclohexylcarbodiimide and N-hydroxysuccinimide to afford the corresponding imidazolide, protected hydrazide and N-hydroxysuccinimidyl ester, respectively. In the instance of the protected hydrazide, the N-(tert-butoxycarbonyl) protecting group is removed by contacting the reagent with anhydrous hydrochloric acid.

Figure 6:
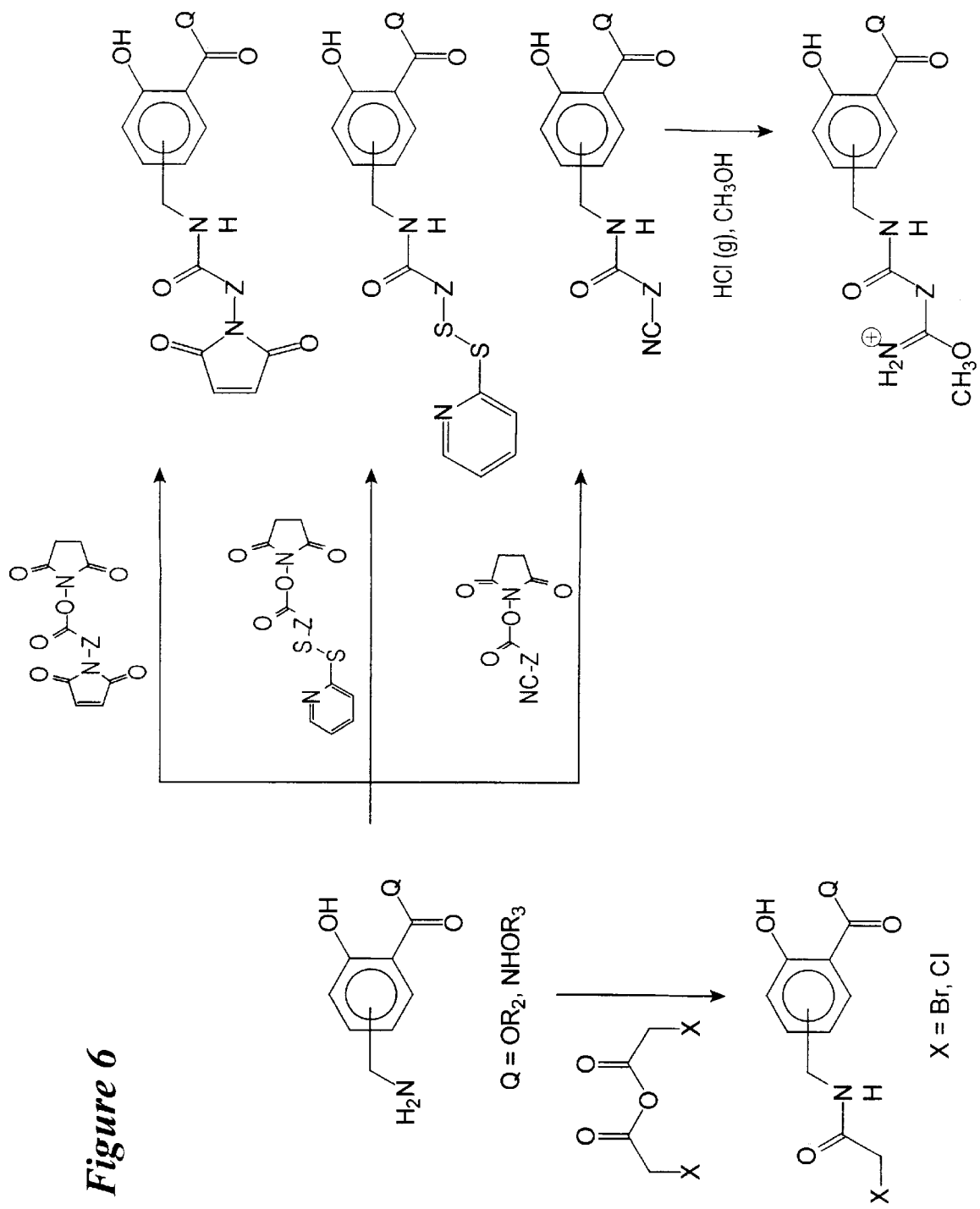
FIG. 6 summarizes the synthesis of reagents of General Formulas I and III, wherein R₂ is one of either an alkyl group or a methylene group bearing an electronegative moiety, and wherein R₁ is selected from either bromo, chloro, iodo, maleimide, dithiopyridyl and imidate ester moieties.

FIG. 6 summarizes the synthesis of reagents of General Formula III, wherein group $R_3$ is preferably selected from one of H, $CH_3$, and a methylene or ethylene moiety with an electronegative substituent, and wherein group $R_1$ is selected from either bromo, chloro, maleimide, dithiopyridyl and imidate ester moieties. Reagents of General Formula III, wherein group $R_1$ is selected from either bromo and chloro moieties, are prepared by condensing a 4- or 5-aminomethylsalicylhydroxamic acid, prepared as summarize in FIG. 4, with either bromoacetic acid anhydride or chloroacetic acid anhydride, respectively. The homologous iodo reagent is prepared by halogen exchange of the chloro reagent with sodium iodide. Reagents of General Formula III, wherein $R_1$ is selected from either bromo, chloro, iodo, bromoacetamide, chloroacetamide and iodoacetamide moieties, may not be conveniently prepared when $R_3$ is H, due to the potential for intermolecular alkylation of the unprotected hydroxamate. Reagents of General Formula III, wherein group $R_1$ is selected from either maleimide and dithiopyridyl moieties, are prepared by condensing a 4- or 5-aminomethylsalicylhydroxamic acid, prepared as summarized in FIG. 4, with an N-hydroxysuccinimidyl ester of an aliphatic carboxylic ester which bears either a terminal maleimide or dithiopyridyl moiety. Reagents of General Formula III, wherein $R_1$ is an imidate ester moiety, are prepared by a two-step process in which a 4- or 5-aminomethylsalicylhydroxamic acid, prepared as summarized in FIG. 4, is first condensed with an N-hydroxysuccinimidyl ester of an aliphatic carboxylic ester which bears a terminal nitrile moiety. Subsequently, the nitrile moiety is converted to the methyl imidate ester by reaction with anhydrous hydrochloric acid in methanol at 0° C.

Reagents of General Formula III, wherein group $R_1$ is selected from either N-hydroxysuccinimidyl ester and dithiopyridyl moieties may be utilized as synthetic intermediates to prepare reagents of General Formula III, wherein group Z is an unbranched saturated or unsaturated chain with at least one of intermediate amide or disulfide moieties.

Reagents of General Formula III, wherein group $R_1$ is an N-hydroxysuccinimidyl ester moiety, may be condensed with compounds having primary aliphatic amine moieties of the general formula $R_1$—$Z_2$—$NH_2$, wherein $Z_2$ is an unbranched saturated or unsaturated chain preferably of from about 1 to 5 carbon equivalents in length, to afford reagents of General Formula III, wherein group Z is an unbranched saturated or unsaturated chain with at least one of intermediate amide moieties.

Figure 7:
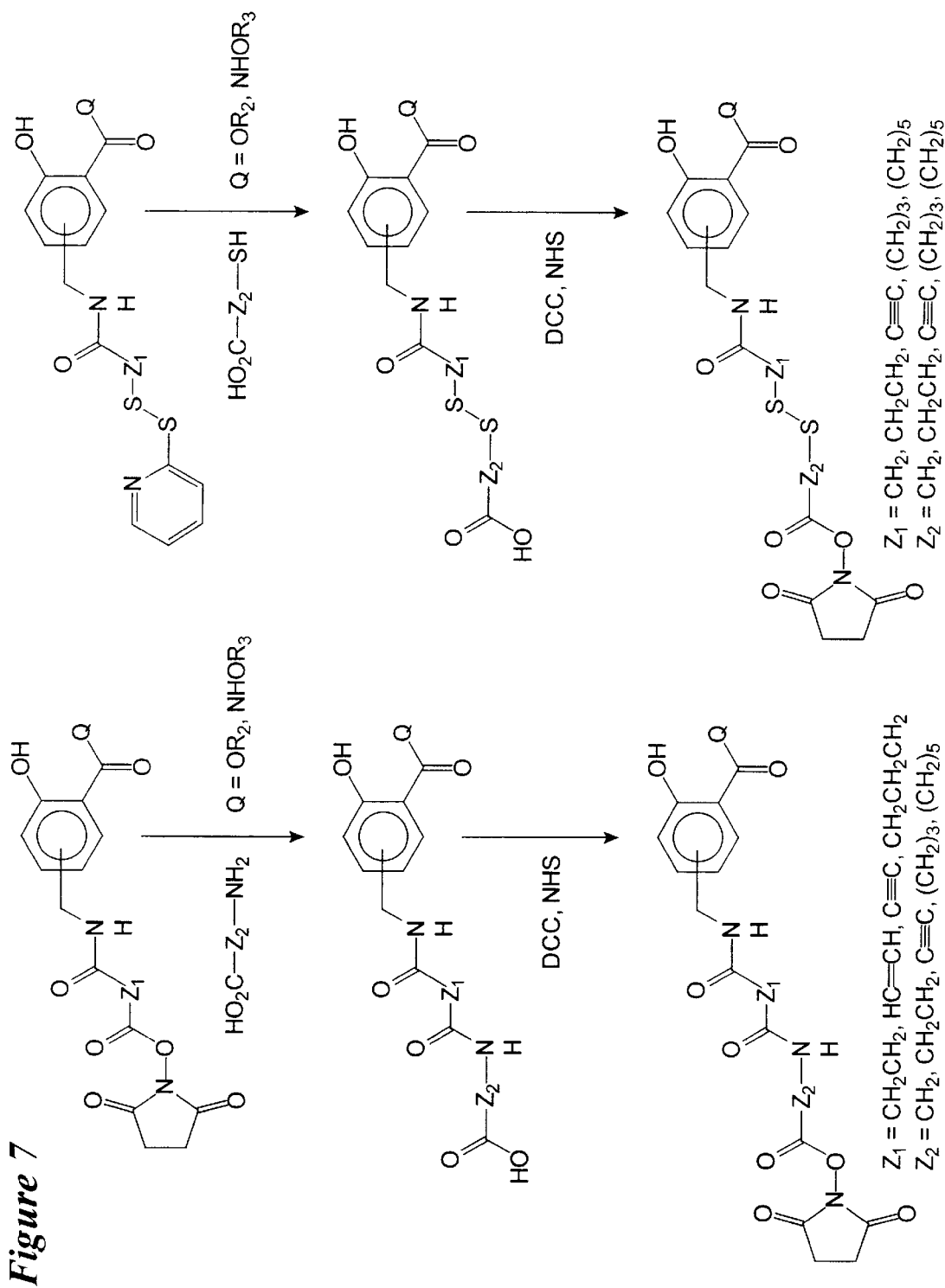
FIG. 7 summarizes the synthesis of reagents of General Formulas I and III, wherein R₁ is an N-hydroxysuccinimidy ester, and wherein Z an unbranched saturated or unsaturated chain of from about 6 to 18 carbon equivalents in length with at least one of either an intermediate amide or disulfide moiety.
Figure 1:
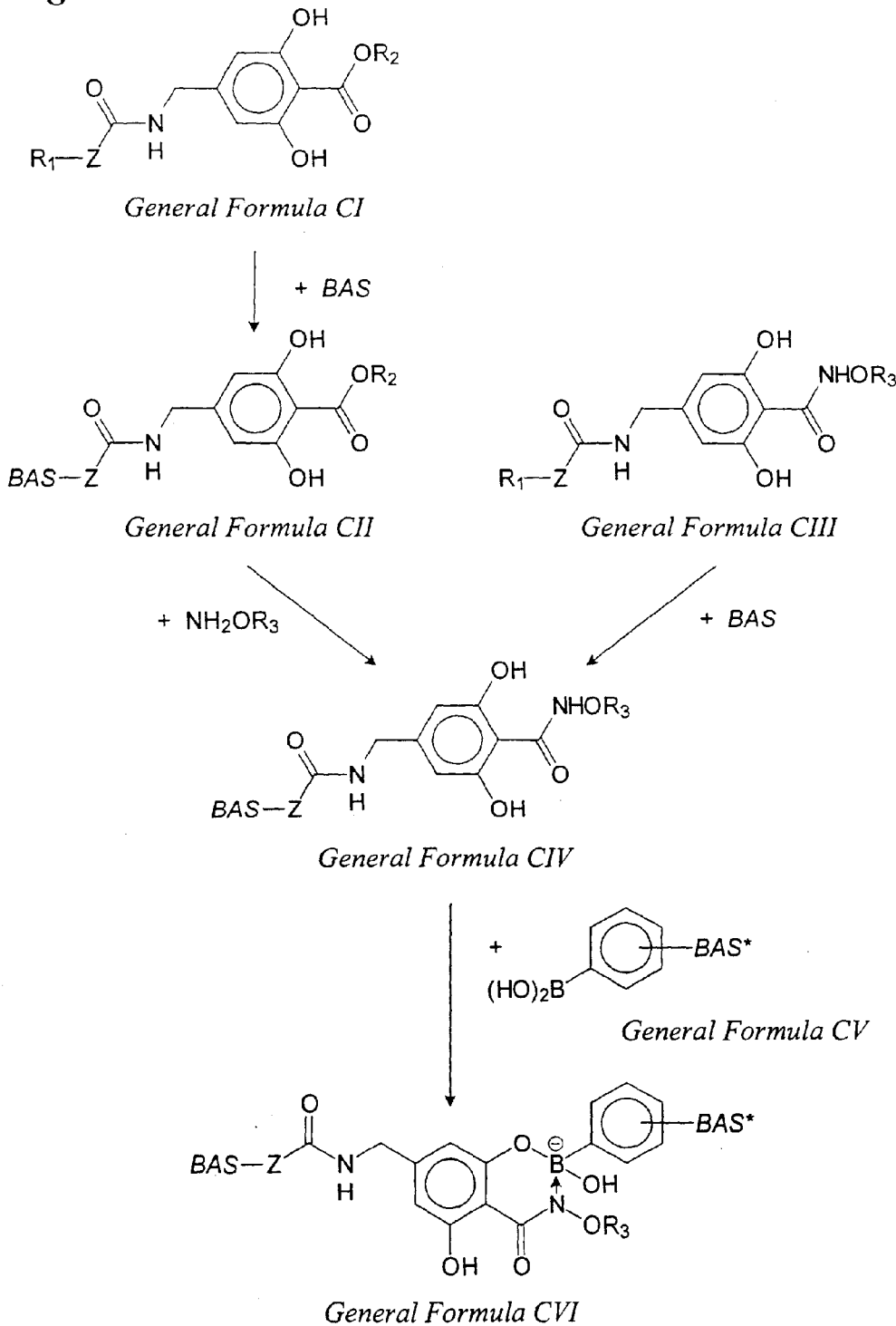
Figure 2:
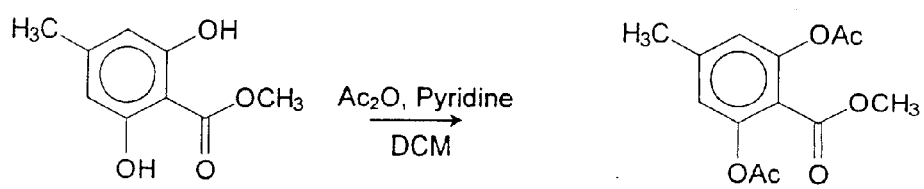
Figure 2:
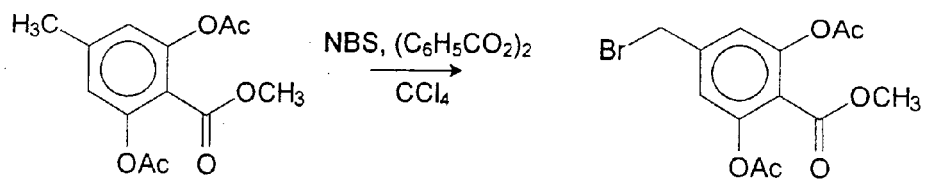
Figure 2:
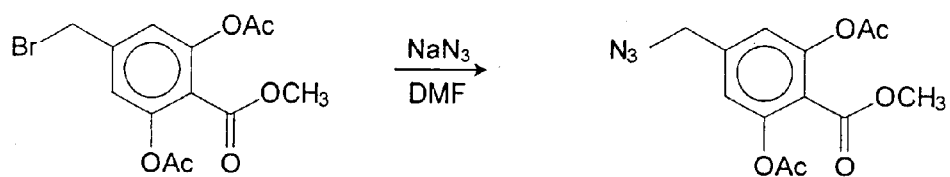
Figure 2:
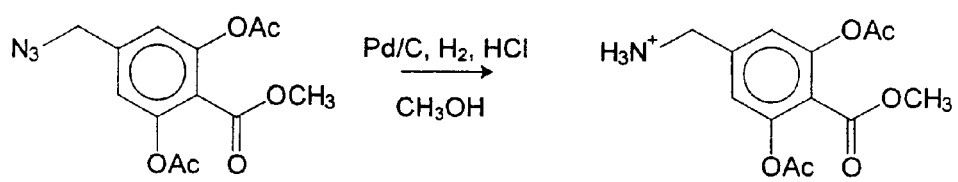
Figure 2:
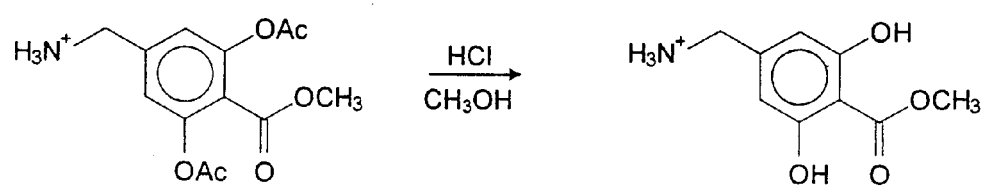
Figure 3:
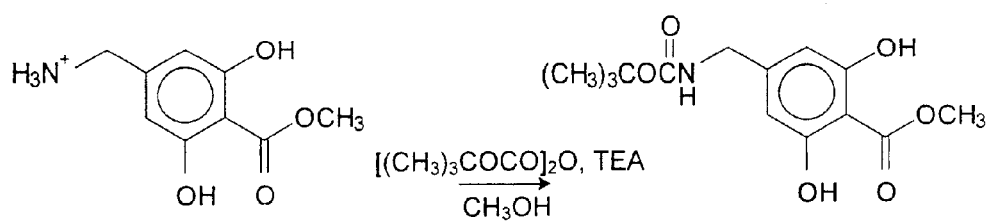
Figure 3:
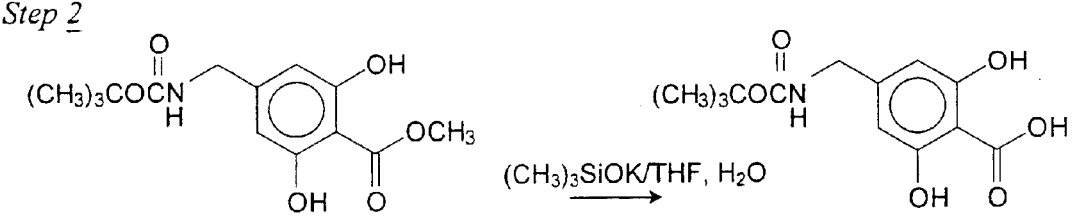
Figure 3:
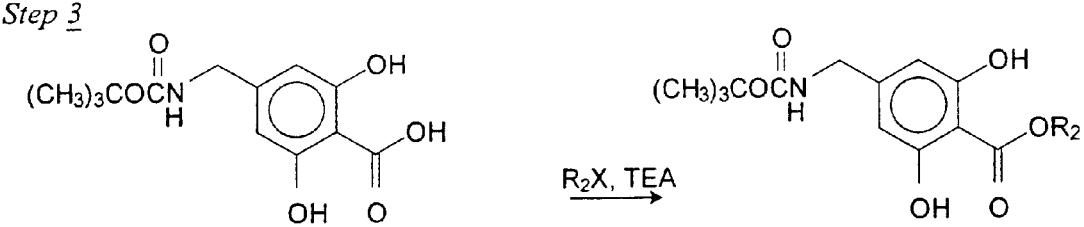
Figure 3:
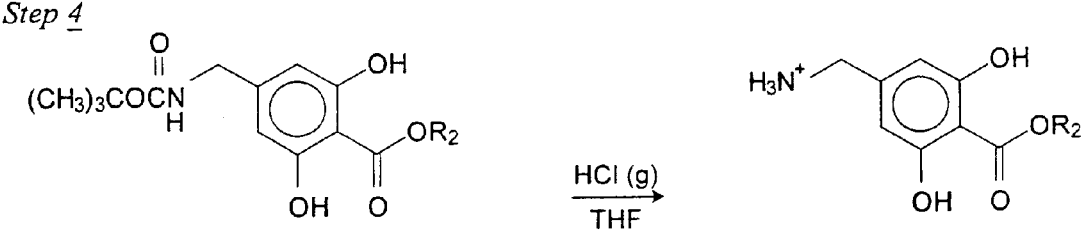
Figure 4:
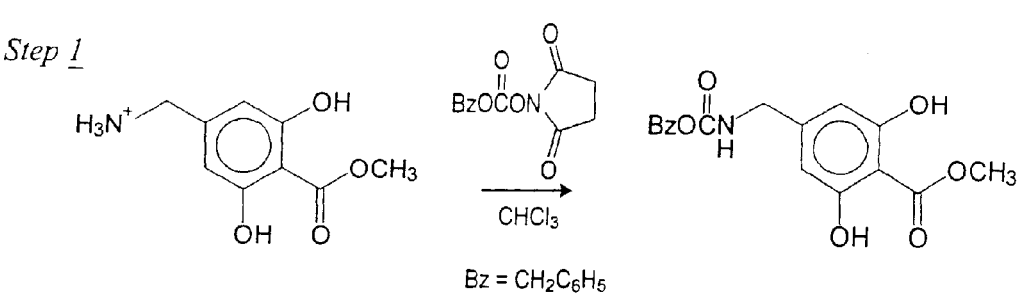
Figure 4:
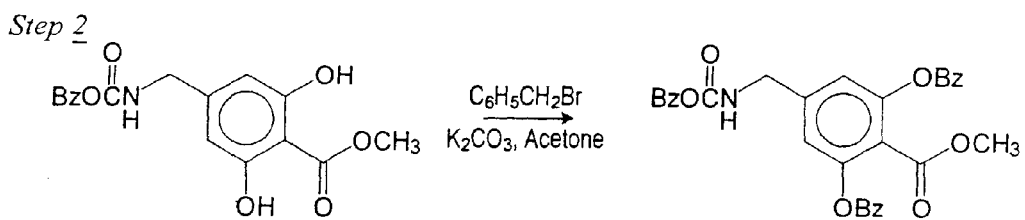
Figure 4:
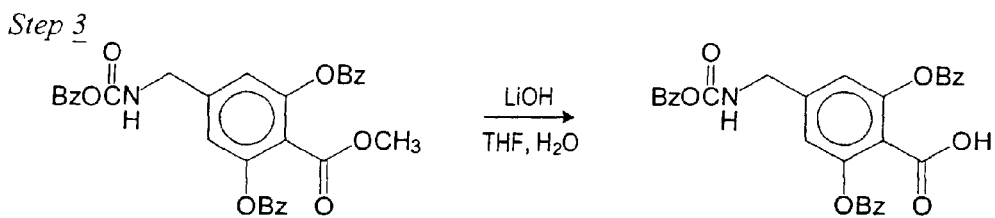
Figure 4:
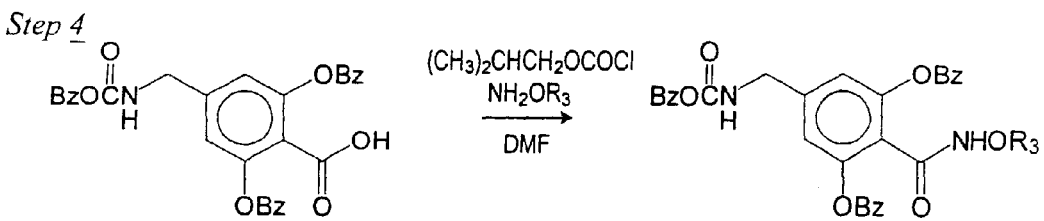
Figure 4:
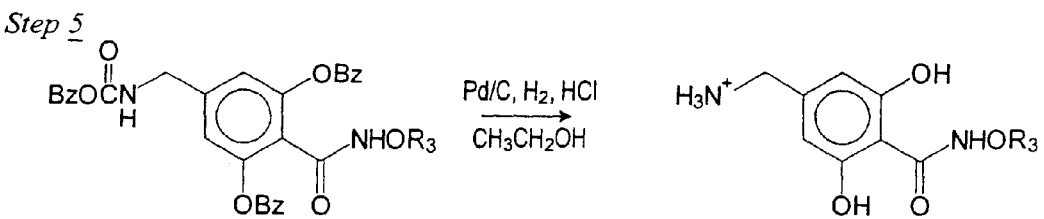
Figure 5:
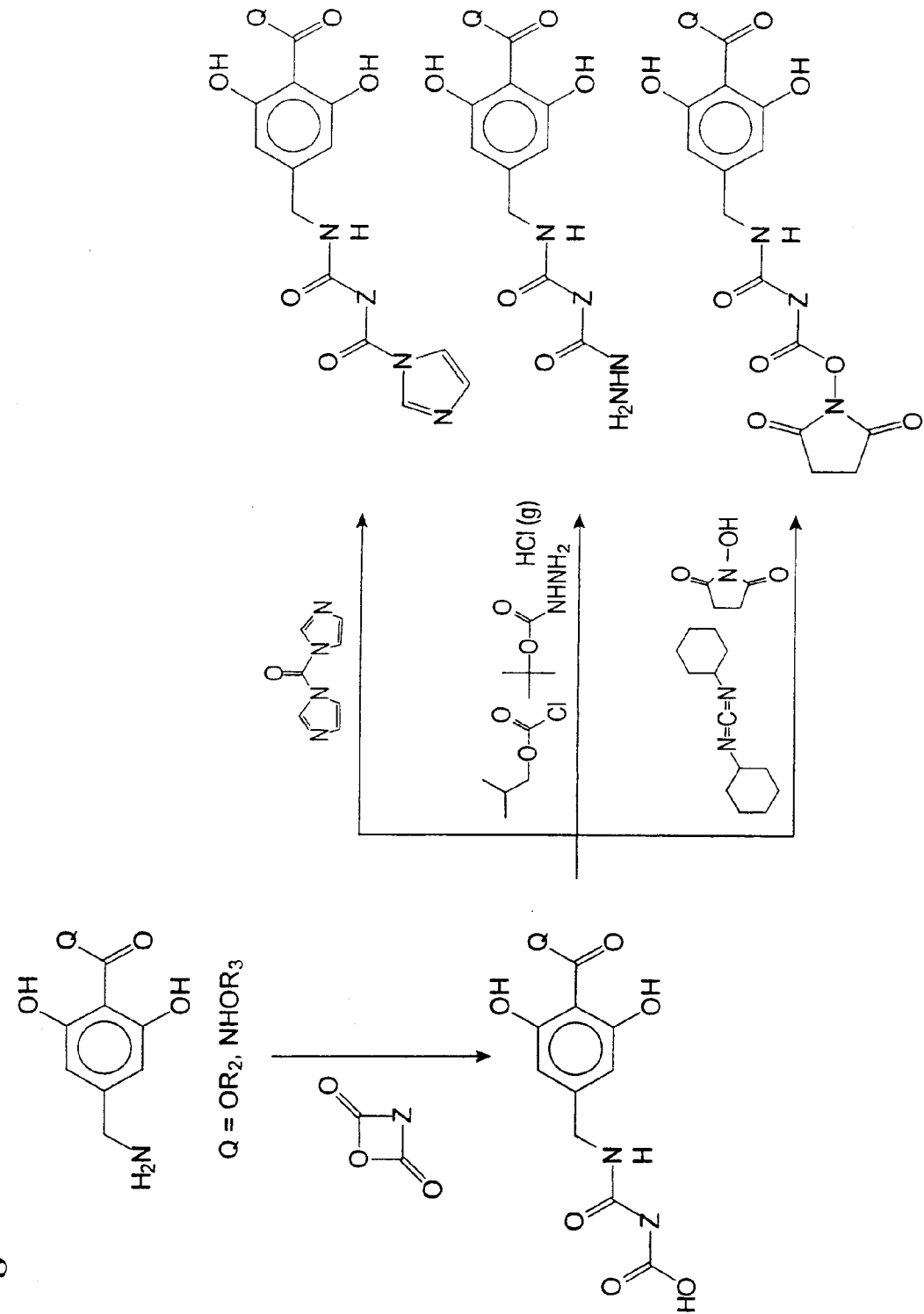
Figure 6:
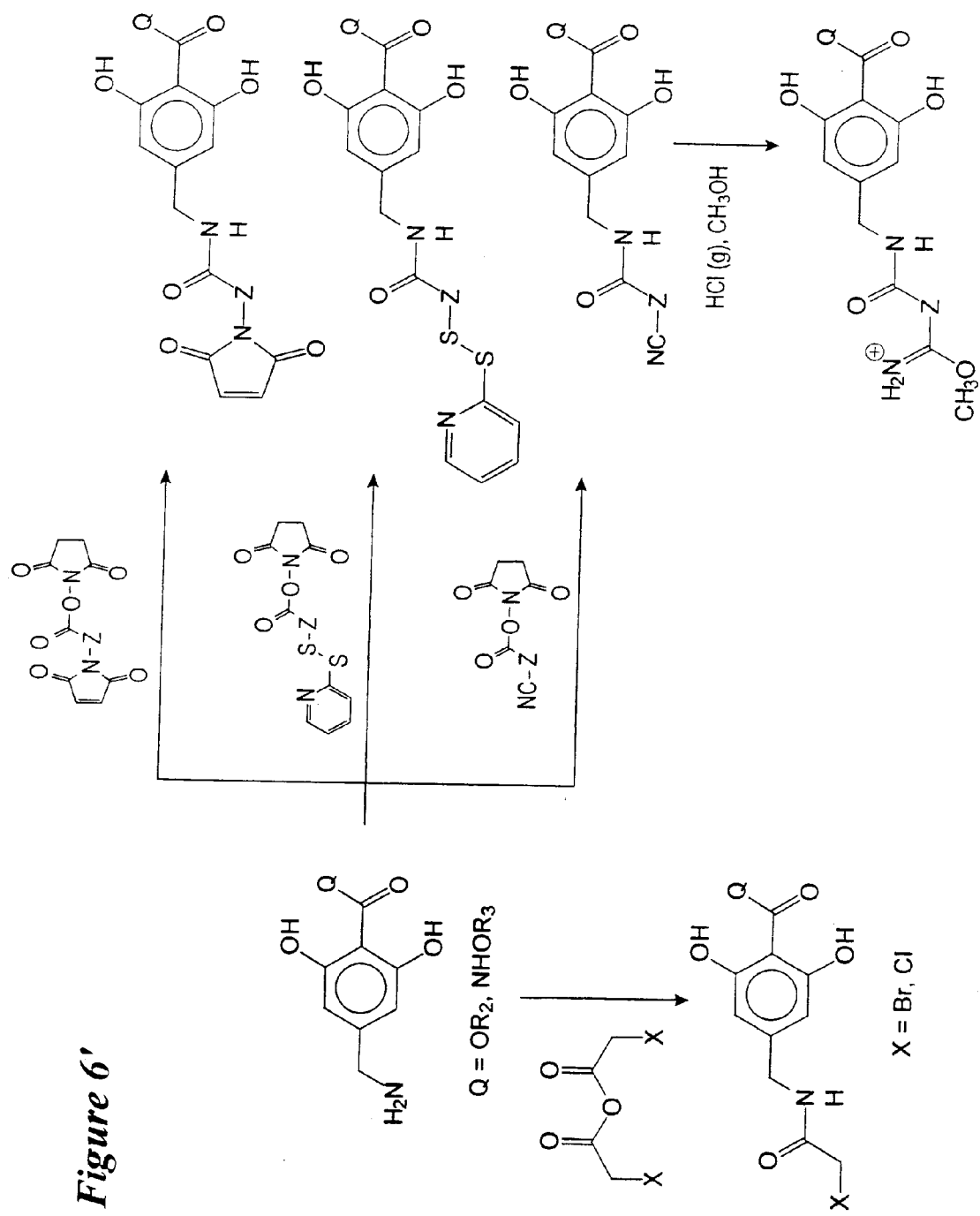
Figure 7:
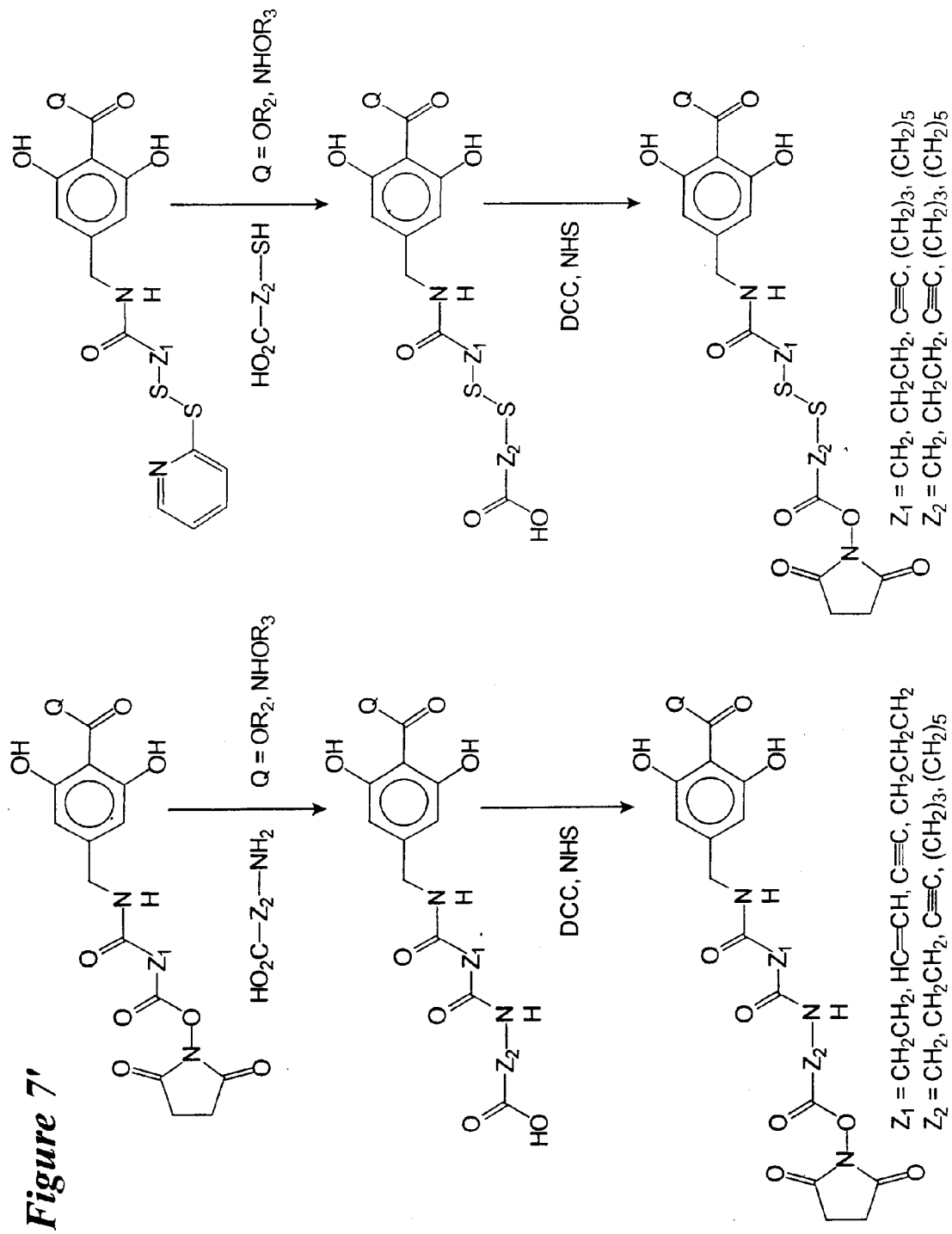

Alternatively, N-hydroxysuccinimidyl ester reagents of General Formula III, preferably derived from a dicarboxylic acid selected from either succinic acid, maleic acid, fumaric acid, acetylenedicarboxylic acid and glutaric acid, may be condensed with compounds having primary aliphatic amine moieties of the general formula $HO2C$—$Z_2$-$NH_2$, wherein $Z_2$ is an unbranched saturated or unsaturated chain preferably of from about 1 to 5 carbon equivalents in length, preferably selected from, either glycine, β-alanine, amniopropiolic acid, 4-amino-butyric acid and 6-aminocaproic acid, to afford compounds having free terminal carboxylic acid moieties which may be further functionalized in accordance with FIG. 5 to afford reagents of General Formula III, wherein Z is an unbranched saturated or unsaturated chain with at least one of intermediate amide moieties. This process is summarized for in FIG. 7 for the synthesis of a reagent of General Formula III, wherein $R_1$ is an N-hydroxysuccinimidyl ester, and wherein Z is an unbranched saturated or unsaturated chain with at least one of an intermediate amide moiety.

Reagents of General Formula III, wherein group $R_1$ is a dithiopyridyl moiety, may be condensed with compounds having terminal thiol moieties of the general formula $R_1$—$Z_2$-SH, wherein $Z_2$ is an unbranched saturated or unsaturated chain preferably of from about 1 to 5 carbon equivalents in length, to afford reagents of General Formula III, wherein group Z is an unbranched saturated or unsaturated chain with at least one of intermediate disulfide moieties.

Alternatively, dithiopyridyl reagents of General Formula III, preferably derived from a mercaptocarboxylic acid selected from either mercaptoacetic acid, β-mercaptopropionic acid, mercaptopropiolic acid, 4-mercaptobutyric acid and 6-mercaptocaproic acid, may be condensed with compounds having a terminal thiol moiety of the general formula $HO_2C$-$Z_2$-SH, wherein $Z_2$ is an unbranched saturated or unsaturated chain preferably of from about 1 to 5 carbon equivalents in length, preferably selected from either mercaptoacetic acid, β-mercaptopropionic acid, mercaptopropiolic acid, 4-mercaptobutyric acid and 6-mercaptocaproic acid, to afford compounds having free terminal carboxylic acid moieties which may be further functionalized in accordance with FIG. 5 to afford reagents of General Formula III, wherein group Z is an unbranched saturated or unsaturated chain with at least one of intermediate disulfide moieties. This process is summarized in FIG. 7 for the synthesis of a reagent of General Formula III, wherein $R_1$ is an N-hydroxysuccinimidyl ester, and wherein Z is an unbranched saturated or unsaturated chain with at least one of a intermediate disulfide moiety.

Reagents of General Formula III, wherein group Z is a polyethylene glycol chain of from about 3 to 12 carbon equivalents in length, are prepared by condensing a 4-aminomethylsalicylhydroxamic acid, prepared as summarized in FIG. 4, with a polyethylene glycol reagent having both an N-hydroxysuccinimidyl ester moiety and either a reactive electrophilic or nucleophilic moiety (or a precursor thereof), many of which are commercially available, to afford reagents of General Formula III, wherein group Z is a polyethylene glycol chain of from about 3 to 12 carbon equivalents in length.

SYNTHESIS OF PUTATIVE PHENYLBORONIC ACID COMPLEXING REAGENTS OF GENERAL FORMULA I

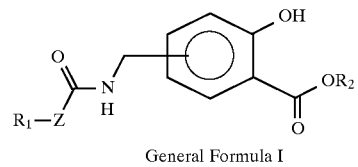

General Formula I

Reagents of General Formula I are derived from either 4- or 5-methylsalicylic acid. In each instance, the reagent is ultimately prepared from a synthetic intermediate which is either an alkyl 4- or 5-aminomethylsalicylate. FIG. 2 summarizes the preparation of alkyl 4- and 5-aminomethylsalicylates, synthetic intermediates leading to reagents of General Formula I, wherein $R_2$ is an alkyl group, e.g., methyl, ethyl, etc. FIG. 2 shows an example where $R_2$ is a methyl group. Initially, in step 1, either 4- or 5-methylsalicylic acid is esterified to afford the corresponding alkyl 4- or 5-methylsalicylate. In step 2, the ester is brominated with N-bromosuccinimide and benzoyl peroxide catalyst to afford the corresponding benzyl bromide. In step 3, the benzyl bromide is alkylated with sodium azide to afford the corresponding benzyl azide. Finally, in step 4, the benzyl azide is subjected to palladium catalyzed hydrogenation in the presence of HCl to afford the corresponding benzyl amine hydrochloride.

Figure 3:
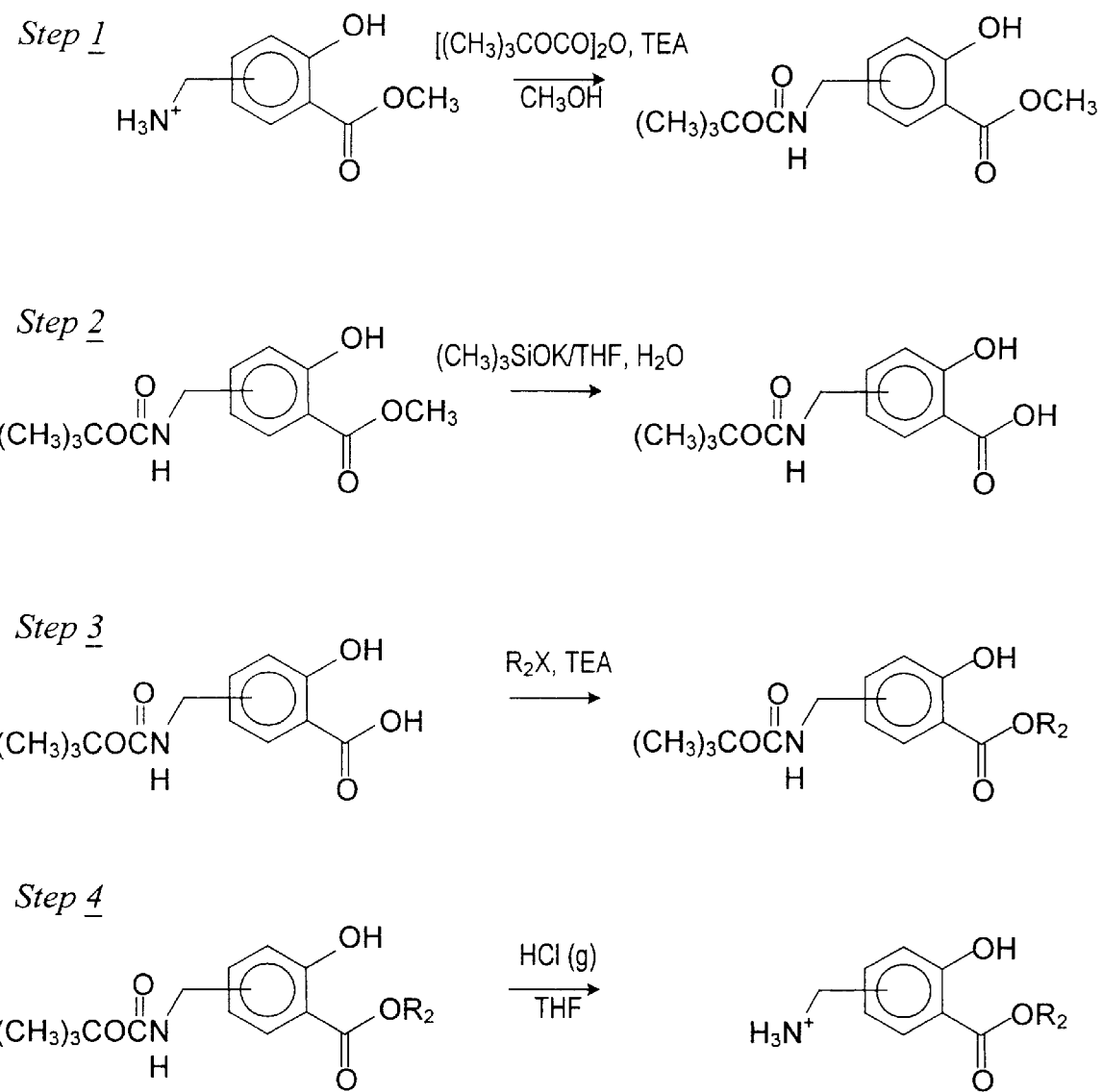
FIG. 3 summarizes the preparation of alkyl 4- and 5-aminomethylsalicylates, synthetic intermediates leading to reagents of General Formula I, wherein $R_2$ is a methylene group bearing an electronegative moiety, e.g., carboxymethyl, cyanomethyl, methoxymethyl, etc.

FIG. 3 summarizes the preparation of synthetic intermediates leading to reagents of General Formula I, wherein group $R_2$ is a methylene or ethylene bearing an electronegative moiety, for example, carboxymethyl, acetamidomethyl and cyanomethyl 4- or 5-aminomethyl-salicylate. It is to be appreciated that other contemplated substituents for group $R_2$ may be prepared by a similar synthesis. Initially, in step 1 of FIG. 3, the alkyl 4- or 5-amino-methylsalicylate, prepared as summarized in FIG. 2, is reacted with di-tert-butyl dicarbonate and triethylamine in methanol to afford the corresponding protected methyl N-(tert-butoxy-carbonyl) aminomethylbenzoate. In step 2, the methyl ester is cleaved by reaction with potassium trimethylsilanolate and worked up in aqueous acid to afford the corresponding benzoic acid. In step 3, the benzoic acid is alkylated by reaction with either an α-haloacid, α-haloacetamide or α-haloacetonitrile and triethylamine to afford the corresponding carboxymethyl, acetamidomethyl or cyanomethyl ester, respectively. Finally, in step 4, the N-(tert-butoxy-carbonyl) protecting group is removed by reaction with anhydrous HCl in tetrahydrofuran to afford the corresponding benzyl amine hydrochloride. In the instance of the protected hydrazide, the N-(tert-butoxycarbonyl) protecting group is removed by contacting the reagent with anhydrous hydrochloric acid.

FIG. 5 summarizes the synthesis of reagents of General Formula I, wherein group $R_2$ is one of either an alkyl or a methylene or ethylene bearing an electronegative substituent, and wherein group $R_1$ is selected from either imidazolide, hydrazide and N-hydroxysuccinimidyl ester moieties. These reagents are each prepared by a two-step process in which an aliphatic acid anhydride is utilized in the first step. Initially, an alkyl 4- or 5-aminomethylsalicylate, prepared as summarized in either FIG. 2 or FIG. 3, is condensed of an aliphatic acid anhydride preferably selected from, but not limited to, either succinic anhydride, glutaric anhydride, Maleic anhydride, and glycolic acid anhydride, in an aprotic organic solvent, which results in the introduction of a spacer (group Z) having a free terminal carboxylic acid moiety. Subsequently, the carboxylic acid moiety is further functionalized by reaction with either N,N-carbonyldiimidazole, isobutylchloroformate and tert-butyl carbazate, or N,N-dicyclohexylcarbodiimide and N-hydroxy-succinimide to afford the corresponding imidazolide, protected hydrazide and N-hydroxy-succinimidyl ester, respectively.

FIG. 6 summarizes the synthesis of reagents of General Formula I, wherein group $R_2$ is one of either an alkyl or a methylene or ethylene bearing an electronegative substituent, and wherein group $R_1$ is selected from either bromo, chloro, maleimide, dithiopyridyl and imidate ester moieties. Reagents of General Formula I, wherein group $R_1$ is selected from either bromo and chloro moieties, are prepared by condensing an alkyl 4- or 5-aminomethylsalicylate, prepared as summarized in either FIG. 2 or FIG. 3, with either bromoacetic acid anhydride or chloroacetic acid anhydride, respectively. The homologous iodo reagent is prepared by halogen exchange of the chloro reagent with sodium iodide. Reagents of General Formula III, wherein $R_1$ is selected from either bromo, chloro, iodo, bromoacetamide, chloroacetamide and iodoacetamide moieties, may not be conveniently prepared when $R_3$ is H, due to the potential for intermolecular alkylation of the unprotected hydroxamate. Reagents of General Formula I, wherein group $R_1$ is selected from either maleimide or dithiopyridyl moieties, are prepared by condensing an alkyl 4- or 5-aminomethylsalicylate, prepared as summarized in either FIG. 2 or FIG. 3, with an N-hydroxysuccinimidyl ester of an aliphatic carboxylic ester which bears either a terminal maleimide or dithiopyridyl moiety. A reagent of General Formula I, wherein $R_1$ is an imidate ester moiety, is prepared by a two-step process in which an alkyl 4- or 5-amino-methylsalicylate, prepared as summarized in either FIG. 2 or FIG. 3, is first condensed with an N-hydroxysuccinimidyl ester of an aliphatic carboxylic ester which bears a terminal nitrile moiety. Subsequently, the nitrile moiety is converted to the methyl imidate ester by reaction with anhydrous hydrochloric acid in methanol at 0° C.

Reagents of General Formula I, wherein group $R_1$ is selected from either dithiopyridyl, imidazolide and N-hydroxysuccinimidyl ester moieties may be utilized as synthetic intermediates to prepare reagents of General Formula I having extended spacers, wherein group Z is an unbranched saturated or unsaturated chain with at least one of intermediate amide or disulfide moieties.

Reagents of General Formula I, wherein group $R_1$ is selected from either imidazolide and N-hydroxysuccinimidyl ester moieties, may be condensed with compounds having primary aliphatic amine moieties of the general formula $R_1$—Z'—$NH_2$, wherein Z' is an unbranched saturated or unsaturated chain preferably of from about 1 to 5 carbon equivalents in length, to afford reagents of General Formula I, wherein group Z is an unbranched saturated or unsaturated chain with at least one of intermediate amide moieties. Note that Z' is shown as $Z_2$ in FIG. 7.

Alternatively, reagents of General Formula I, wherein group $R_1$ is selected from either imidazolide and N-hydroxysuccinimidyl ester moieties, may be condensed with compounds having primary aliphatic amine moieties of the general formula $H_2N$—Z'—COOH, wherein Z' is an unbranched saturated or unsaturated chain preferably of from about 1 to 5 carbon equivalents in length, preferably selected from, but not limited to, either glycine, β-alanine, 4-aminobutyric acid and 6-aminocaproic acid, to afford compounds having a free terminal carboxylic acid moiety which may be further functionalized in accordance with FIG. 5 to afford reagents of General Formula I, wherein Z is an unbranched saturated or unsaturated chain with at least one of intermediate amide moieties.

Reagents of General Formula I, wherein group $R_1$ is a dithiopyridyl moiety, may be condensed with compounds having terminal thiol moieties of the general formula $R_1$—Z'—SH, wherein Z' is an unbranched saturated or unsaturated chain preferably of from about 1 to 5 carbon equivalents in length, to afford reagents of General Formula I, wherein group Z is an unbranched saturated or unsaturated chain with at least one of intermediate disulfide moieties.

Alternatively, reagents of General Formula I, wherein group $R_1$ is a dithiopyridyl moiety, may be condensed with compounds having terminal thiol moieties of the general formula HS—Z'—COOH, wherein Z' is an unbranched saturated or unsaturated chain preferably of from about 1 to 5 carbon equivalents in length, to afford compounds having a free terminal carboxylic acid moiety which may be further functionalized in accordance with FIG. 5 to afford reagents of General Formula I, wherein group Z is an unbranched saturated or unsaturated chain with at least one of intermediate disulfide moieties.

Reagents of General Formula I, wherein group Z is a polyethylene glycol chain of from about 3 to 12 carbon equivalents in length, are prepared by condensing an alkyl 4- or 5-aminomethylsalicylate, prepared as summarized in either FIG. 2 or FIG. 3, with a polyethylene glycol reagent having both an N-hydroxysuccinimidyl ester moiety and either a reactive electrophilic or nucleophilic moiety (or a precursor thereof), many of which are commercially available, to afford reagents of General Formula I, wherein group Z is a polyethylene glycol chain of from about 3 to 12 carbon equivalents in length.

PREPARATION OF PHENYLBORONIC ACID COMPLEXING CONJUGATES OF GENERAL FORMULA IV

At this point, phenylboronic acid complexing reagents of General Formula III may be reacted with a suitable biologically active species to yield the conjugate of the general formula of General Formula IV:

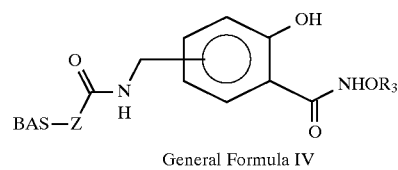

General Formula IV

Alternatively, the putative phenylboronic acid complexing reagents of General Formula I may be reacted with a suitable biologically active species to yield the conjugate of the general formula of General Formula II:

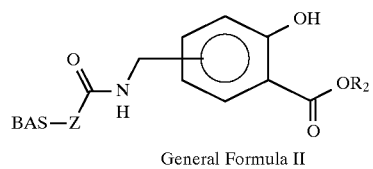

General Formula II

The conjugate of General Formula II is next condensed with a hydroxylamine derivative to yield the corresponding phenylboronic acid complexing conjugate of the general formula of General Formula IV:

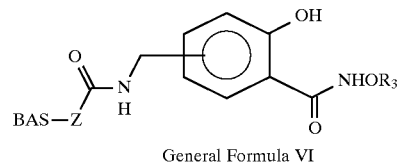

General Formula VI

Suitable hydroxylamine derivatives are preferably selected from, but not limited to, $NH_2OH$, $NH_2OCH_3$, $NH_2OCH_2CN$, $NH_2OCH_2COOH$, $NH_2OCH_2CONH_2$, $NH_2OCH_2CH_2OH$, $NH_2OCH_2OCH_3$. When group $R_2$ in General Formula II is an alkyl group, $NH_2OH$ is preferably utilized to effect the interconversion of General Formula II to General Formula IV.

PREPARATION OF BIOCONJUGATES OF GENERAL FORMULA IV

Bioconjugates of General Formula VI may be prepared in buffered aqueous solutions or organic solvents. Preferred buffers include acetate, citrate, phosphate, carbonate and diglycine. Borate buffers should be avoided due to their ability to complex with the phenylboronic acid complexing moiety. Tris, β-hydroxyamine and β-hydroxyacid buffers should be avoided due to their ability to complex with the phenylboronic acid. The bioconjugate is formed within a few minutes over a range of temperatures of from about 4° C. to 70° C. The stability of the bioconjugate in aqueous solution at a given pH and temperature is influenced, to some extent, by substituent group $R_3$. Bioconjugates of General Formula VI are stable in aqueous solutions of approximate pH greater than 3.5 and less than 10.5. The bioconjugation reaction (phenylboronic acid complexation) is insensitive to significant variations in ionic strength over the range 0.01 to 1M, the presence of organic solvents including acetonitrile, methanol, ethanol, isopropanol, butanol, N,N-dimethylformamide and dimethylsulfoxide, the presence of detergents, and the presence of chaotropic agents (protein denaturants) including urea, guanidine hydrochloride, guanidine thiocyanate and formamide, which are incompatible with prior art indirect labeling systems wherein the structure of a biological macromolecule must be maintained to preserve requisite binding properties. Once formed, the bioconjugates are stable upon removal of water, and can be lyophilized for storage.

The stability of the bioconjugate at a given pH is determined to some extent by substituent group $R_3$. Phenylboronic acid complexes of General Formula VI, wherein group $R_3$ is H, are stable in buffered aqueous solutions over the approximate pH range 35 to 10.5. Phenylboronic acid complexes of General Formula VI, wherein group $R_3$ is $CH_3$, are stable in buffered aqueous solutions over the approximate pH range 4.5 to 10.5. Phenylboronic acid complexes of General Formula VI, wherein group $R_3$ includes an electronegative moiety, are stable in buffered aqueous solutions over the approximate pH range less than 3.5 to 10.5.

The stability of the phenylboronic acid complex toward acid catalyzed hydrolysis is related to the $pK_a$ of the hydroxamic acid participating in the complex. The lower the $pK_a$ of the hydroxamic acid moiety the more stable the complex. Consequently, phenylboronic acid complexes of General Formula VI wherein group $R_3$ includes an electronegative moiety exhibit greater stability toward acid catalyzed hydrolysis than do those in which $R_3$ is either H or $CH_3$.

The following examples present a detailed description of the synthesis of reagents of General Formula I and General Formula III.

EXAMPLE I

Preparation of Ethyl 4-Aminomethylsylicylate Hydrochloride

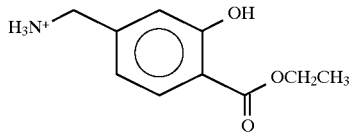

Ethyl 4-Methylsalicylate.

4-Methylsalicylic acid (20.0 g, 131 mmoles) was dissolved in ethanol (300 mL) and concentrated sulfuric acid (2.0 mL) was added. The mixture was refluxed for 40 hours. The volume of the reaction mixture was reduced to 100 mL, transferred to a separatory funnel, and diluted with chloroform (250 mL) and water (200 mL). Solid sodium bicarbonate was added in small portions until the pH of the aqueous layer was about 8 (pH test paper). The mixture in the funnel was shaken well and the layers separated. The organic layer was washed first with water (150 mL) and then saturated aqueous sodium chloride (150 mL). Finally, the organic solution was dried over anhydrous magnesium sulfate, filtered, and the solvent evaporated to afford 14.0 g (59% yield) of liquid ethyl 4-methylsalicylate.

$^1$H NMR (300 MHz, CHCl$_3$-d) δ1.40 (triplet, J=7 Hz, 3H, CH$_2$CH$_3$), 2.33 (singlet, 3H, ArCH$_3$), 4.38 (quartet, J=7 Hz, 2H, CH$_2$CH$_3$), 6.67 (doublet, J=8 Hz, 1H, ArH), 6.78 (singlet, 1H, ArH), 7.72 (doublet, J=8 Hz, 1H, ArH), 10.81 (singlet, 1H, OH). $^{13}$C NMR (75 MHz, CHCl$_3$-d) δ14.0, 21.7, 61.1, 110.1, 117.7, 120.4, 129.7, 146.9, 161.7, 170.3.

Ethyl 4-Bromomethylsalicylic Acid

Ethyl 4-methylsalicylate (13.1 g, 72.5 mmoles) was dissolved in carbon tetrachloride (150 mL) and N-bromosuccinimide (13.1 g, 73.2 mmoles) and benzoyl peroxide (0.2 g, 0.8 mmoles) were added. The mixture was refluxed for 3.5 hours and then allowed to cool to room temperature. The solids were removed by filtration and the filtrate was evaporated to dryness. The crude solid product was crystallized from hexane (100 mL) to afford 5.0 g (27% yield) of ethyl 4-bromomethylsalicylic acid (m.p. 64°–66° C.).

$^1$NMR (300 MHz, CHCl$_3$-d) δ1.41 (triplet, J=7 Hz, 3H, CH$_2$CH$_3$), 4.40 (quartet, J=7 Hz, 2H, CH$_2$CH$_3$), 4.40 (singlet, 2H, CH$_2$Br), 6.90 (doublet, J=8 Hz, 1H, ArH), 6.99 (singlet, 1H, ArH), 7.82 (doublet, J=8 Hz, 1H, ArH), 10.88 (singlet, 1H, OH). $^{13}$C NMR (75 MHz, CHCl$_3$-d) δ14.0, 31.9, 61.5, 112.4, 117.9, 119.8, 130.5, 145.5, 161.8, 169.9.

Ethyl 4-Aminomethylsalicylate Hydrochloride

Ethyl 4-bromomethylsalicylate (4.8 g, 18.6 mmoles) was dissolved in dry N,N-di-methylformamide (50 mL) and sodium azide (1.2 g, 18.9 mmoles) was added. The suspension was stirred at room temperature for 2 hours. The reaction mixture was then diluted with dichloromethane (150 mL) and extracted with 1N aqueous hydrochloric acid (100 mL), water (100 mL), and saturated aqueous sodium chloride (50 mL). Finally, the solution was then dried over anhydrous magnesium sulfate, filtered, and evaporated to dryness to give ethyl 4-azidomethylsalicylate as an oil.

Palladium on carbon (0.5 g 10% [w/w]) was added to a 1L hydrogenation flask under a nitrogen atmosphere. The crude ethyl 4-azidomethylsalicylate was dissolved in ethanol (200 mL) and transferred to the hydrogenation flask. Concentrated aqueous hydrochloric acid (2 mL) was then added, and the flask was affixed to the Parr hydrogenator. The reaction mixture was shaken under 35 psi of hydrogen for 4 hours at room temperature. The mixture was then filtered through Celite to remove the catalyst, and the filtrate was evaporated to dryness to afford an off-white solid. Finally, this solid was crystallized from EtOH to afford 3.1 g (71% yield) of ethyl 4-aminomethylsalicylate hydrochloride (m.p. 240°–241° C.).

$^1$H NMR (300 MHz, DMSO-d$_6$) δ1.30 (triplet, J=7 Hz, 3H, CH$_2$CH$_3$), 3.99 (singlet, 2H, CH$_2$NH$_3$), 4.33 (quartet, J=7 Hz, 2H, CH$_2$CH$_3$), 7.06 (doublet, J=8 Hz, 1H, ArH), 7.15 (singlet, 1H, ArH), 7.77 (doublet, J=8 Hz, 1H, ArH), 8.71 (broad singlet, 3H, NH$_3$), 10.62 broad singlet, 1H, OH). $^{13}$C NMR (75 MHz, DMSO-d$_6$) δ14.0, 38.7, 41.6, 61.5, 112.9, 117.7, 119.8, 130.3, 142.2, 160.2, 168.9.

EXAMPLE II

Preparation of a Reagent of General Formula I
Ethyl N-Iodoacetyl-4-aminomethylsalicylate

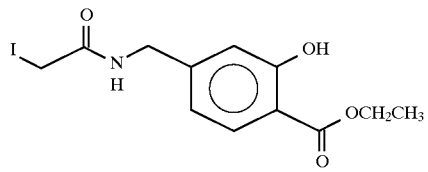

Ethyl N-Chloroacetyl-4-aminomethylsalicylate

Ethyl 4-aminomethylsalicylate hydrochloride (0.50 g, 2.17 mmoles) was suspended in dry N,N-dimethylformamide (25 mL) and N,N-diisopropylethylamine (0.38 mL, 2.18 mmoles) was added. Once the amine salt dissolved, chloroacetic anhydride (0.39 g, 2.25 mmoles) was added and the reaction mixture was stirred at room temperature for 4.5 hours. The reaction mixture was then diluted with ethyl acetate (100 mL), and this solution was extracted with 1N aqueous hydrochloric acid (100 mL), water (50 mL), and saturated aqueous sodium chloride (50 mL). The ethyl acetate solution was dried over anhydrous magnesium sulfate, filtered and evaporated to dryness to afford a white solid. Finally, this solid was crystallized from ethyl acetate:hexanes (8:2, 10 mL) to afford 0.13 g (22% yield) of ethyl N-chloroacetyl-4-aminomethylsalicylate (m.p. 120°–121° C.).

$^1$H NMR (300 MHz, DMSO-$d_6$) δ1.31, (triplet, J=7 Hz, 3H, $CH_2CH_3$), 4.14 (singlet, 2H, $ClCH_2$), 4.29 (doublet, J=6 Hz, 2H, $NHCH_2$), 4.34 (quartet, J=7 Hz, 2H, $CH_2CH_3$), 6.82 (doublet, J=8 Hz, 1H, ArH), 6.84 (singlet, 1H, ArH), 7.73 (doublet, J=8 Hz, 1H, ArH), 8.78 (triplet, J=6 Hz, 1H, NH), 10.58 (singlet, 1H, OH). $^{13}$C NMR (75 MHz, DMSO-$d_6$) δ13.9, 42.1, 42.6, 61.3, 111.6, 115.6, 118.4, 130.1, 147.6, 160.6, 166.5, 169.1.

Ethyl N-Iodoacetyl-4-aminomethylsalicylate

Ethyl N-chloroacetyl4-aminomethylsalicylate (0.11 g, 0.40 mmoles) was dissolved in acetone (5 mL) and sodium iodide (0.06 g, 0.40 mmoles) was added. The solution was refluxed for 2.5 hours, then cooled to room temperature and filtered. The filtrate was evaporated to dryness to afford a white solid of ethyl N-iodoacetyl4-aminomethylsalicylate (0.19 g, 100% yield) (m.p. 105°–108° C.).

$^1$H NMR (300 MHz, DMSO-$d_6$) δ1.31, (triplet, J=7 Hz, 3H, $CH_2CH_3$), 3.68 (singlet, 2H, $ICH_2$), 4.26 (doublet, J=6 Hz, 2H, $NHCH_2$), 4.33 (quartet, J=7 Hz, 2H, $CH_2CH_3$), 6.82 (doublet, J=8 Hz, 1H, ArH), 6.84 (singlet, 1H, ArH), 7.72 (doublet, J=8 Hz, 1H, ArH), 8.79 (triplet, J=6 Hz, 1H, NH), 10.58 (singlet, 1H, OH). $^{13}$C NMR (75 MHz, DMSO-$d_6$) δ0.41, 13.9, 42.0, 61.3, 111:4, 115.5, 118.3, 130.1, 147.9, 160.6, 168.3, 169.1.

EXAMPLE III

Preparation of a Reagent of General Formula I
Ethyl (6-Aminohexanoyl)aminomethylsalicylate
Trifluoroacetate

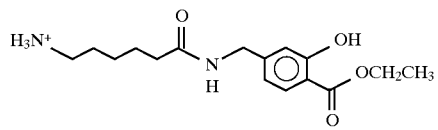

Ethyl (N-tert-Butoxycarbonyl-6-aminohexanoyl) aminomethylsalicylate

Ethyl 4-aminomethylsalicylate hydrochloride (0.52 g 1.28 mmoles) was suspended in anhydrous N,N-dimethylformamide (25 mL), and N,N-diisopropylethylamine (0.79 mL, 4.53 mmoles) was added, followed by N-tert-butoxycarbonyl-6-aminohexanoic acid succinimidyl ester (0.74 g, 2.26 mmoles). The mixture was stirred under dry nitrogen for 18 hours, during which time all solids dissolved. The reaction mixture was diluted with ethyl acetate (100 mL) and extracted with 1N aqueous hydrochloric acid (100 mL). The layers were separated, and the ethyl acetate solution was washed with water (100 mL) and saturated aqueous sodium chloride (500 mL). The ethyl acetate solution was dried over anhydrous magnesium sulfate, filtered, and evaporated to afford an amorphous off-white solid. Finally, the solid was crystallized from ethyl acetate, filtered, and dried in vacuo to afford 0.67 g (73% yield) of ethyl (N-tert-butoxycarbonyl-6-aminohexanoyl) aminomethylsalicylate (m.p. 120°–121° C., open capillary, uncorrected).

$^1$H NMR (300 MHz, DMSO-$d_6$) δ1.19 (multiplet, 2H, $NHCH_2CH_2CH_2CH_2CH_2CO$), 1.34 (multiplet, 5H, $CH_2CH_2CO$ and $CH_2CH_3$), 1.34 (singlet, 9H, $C(CH_3)_3$), 1.49 (multiplet, 2H, $NHCH_2CH_2$), 2.12 (triplet, J=7 Hz, 2H, $CH_2CH_2CO$), 2.87 (quartet, J=6 Hz, 2H, $NHCH_2CH_2$), 4.23 (doublet, J=6 Hz, 2H, $CH_2Ar$), 4.32 (quartet, J=7 Hz, $CH_2CH_3$), 6.74 (triplet, J=6 Hz, 1H, $CONHCH_2CH_2$), 6.80 (doublet, J=8 Hz, 1H, ArH), 6.81 singlet, 1H, ArH), 7.71 (doublet, J=8 Hz, 1H, ArH), 8.34 (triplet, J=6 Hz, 1H, $CONHCH_2Ar$), 10.58 (singlet, 1H, OH). $^{13}$C NMR (75 MHz, DMSO-$d_6$) δ14.0, 25.1, 26.3, 28.3, 29.7, 36.3, 40.2, 42.9, 61.4, 79.0, 111.6, 116.0, 118.3, 130.4, 146.9, 156.2, 161.9, 170.1, 173.0.

Ethyl (6-Aminohexanoyl)aminomethylsalicylate Trifluoroacetate

Ethyl (N-tert-butoxycarbonyl-6-aminohexanoyl) aminomethylsalicylate (0.58 g, 1.41 mmoles) was dissolved in dichloromethane (5 mL) and the solution was cooled in an ice/water bath. Trifluoroacetic acid (5 mL) was added, and the reaction was allowed to warm to room temperature. After 2 hours, the reaction mixture was evaporated to dryness to give the product as an oil, which was dried in vacuo over potassium hydroxide pellets to afford 0.59 g (99% yield) of ethyl (6-aminohexanoyl)aminomethylsalicylate trifluoroacetate.

$^1$H NMR (300 MHz, DMSO-$d_6$) δ1.28 (multiplet, 5H, $H_3CH_2CH_2CH_2CH_2CH_2CO$ and $CH_2CH_3$), 1.53 (multiplet, 4H, $NH_3CH_2CH_2CH_2CH_2CH_2CO$), 2.15 (triplet, J=8 Hz, 2H, $CH_2CH_2CO$), 2.71 (multiplet, 2H, $NH_3CH_2CH_2$), 4.21 (doublet J=6 Hz, 2H, $CH_2Ar$), 4.30 (quartet, J=8 Hz, 2H, $CH_2CH_3$), 6.79 (doublet, J=8 Hz, 1H, ArH), 6.81 (singlet, 1H, ArH), 7.68 (doublet, J=8 Hz, 1H, ArH), 8.18 (broad singlet, 3H, $NH_3$), 8.60 (triplet, J=6 Hz, 1H, $CONHCH_2Ar$), 10.58 (broad singlet, 1H, OH). $^{13}$C NMR (75 MHz, DMSO-$d_6$) δ14.0, 24.8, 25.6, 26.7, 35.1, 38.6, 41.7, 61.3, 111.5, 115.5, 118.3, 130.1, 148.6, 160.6, 169.2, 172.6.

EXAMPLE IV

Preparation of a Reagent of General Formula I
Methyl 4-Succinylaminomethylsalicylate
Succinimidyl Ester

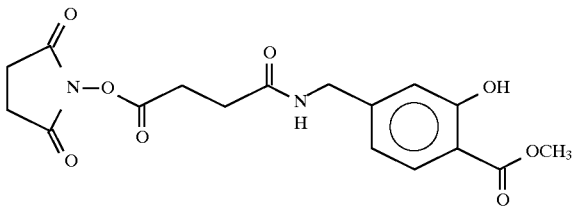

Methyl 4-Methylsalicylate

4-Methylsalicylic acid (100 g, 658 mmoles) was dissolved in anhydrous methanol (500 mL) and concentrated sulfuric acid (25 mL) was added carefully. The solution was refluxed for 18 hours, then cooled to room temperature. The reaction mixture was concentrated to about 150 mL, and ethyl acetate (250 mL) was added. The ethyl acetate solution was washed twice with saturated aqueous sodium bicarbonate (250 mL portions) and then with saturated aqueous sodium chloride (100 mL). The ethyl acetate solution was dried over anhydrous sodium sulfate, filtered, and evaporated to a clear, reddish-brown liquid. This crude product was vacuum distilled (oil pump) to afford a clear, viscous liquid that solidified on standing to afford 98.1 g (90% yield) of methyl 4-methylsalicylate.

$^1$H NMR (300 MHz, CHCl$_3$-d) δ2.32 (singlet, 3H, ArCH$_3$), 3.91 (singlet, 3H, OCH$_3$), 6.67 (doublet, J=8 Hz, 1H, ArH), 6.78 (singlet, 1H, ArH), 7.69 (doublet, J=8 Hz, 1H, ArH), 10.71 (singlet, 1H, OH). $^{13}$C NMR (75 MHz, CHCl$_3$-d) δ21.8, 52.1, 110.0, 117.9, 120.6, 129.9, 147.3, 161.9, 170.9.

Methyl 4-Bromomethylsalicylate

Methyl 4-methylsalicylate (98.1 g, 590 mmoles) was dissolved in carbon tetrachloride (600 mL), and N-bromosuccinimide (105.0 g, 590 mmoles) and benzoyl peroxide (0.7 g 3 mmoles) were added. The mixture was refluxed under nitrogen. After 2 hours, an additional portion (0.7 g) of N-bromosuccinimide was added. Reflux was continued for 16 hours. The reaction mixture was cooled to room temperature and the solid removed by filtration. The yellow filtrate was evaporated to dryness to afford a thick yellow syrup that solidified on standing. Hexanes (500 mL) was added to the solid, and the mixture was boiled until almost all solids dissolved. The hot hexanes solution was filtered and concentrated until a solid just began to precipitate. The mixture was heated to dissolve the solid, and the solution was allowed to cool slowly to room temperature. Pale yellow crystals formed slowly. The mixture was then chilled in ice for 2 hours to complete crystallization. Finally, the solid was filtered, washed with cold hexanes (100 mL), and dried in vacuo to afford 83.5 g (58% yield) of methyl 4-bromomethylsalicylate (m.p. 73°–75° C., open capillary, uncorrected).

$^1$H NMR (300 MHz, CHCl$_3$-d) δ3.95 (singlet, 3H, OCH$_3$), 4.40 (singlet, 2H, CH$_2$), 6.90 (doublet, J=8 Hz, 1H, ArH), 7.00 (singlet, 1H, ArH), 7.80 (doublet, J=8 Hz, 1H, ArH), 10.78 (singlet, 1H, OH). $^{13}$C NMR (75 MHz, CHCl$_3$-d) δ32.1, 52.5, 112.4, 118.2, 120.1, 130.7, 145.8, 162.0, 170.5.

Methyl 4-Azidomethylsalicylate

Methyl 4-bromomethyl salicylate (83.5 g, 341 mmoles) was dissolved in dry N,N-dimethylformamide (150 mL) and sodium azide 925.0 g, 380 mmoles) was added. The yellow suspension was stirred at room temperature, and the solids rapidly dissolved. The solution turned brown, and a precipitate of sodium bromide formed. The reaction mixture was stirred 16 hours, then filtered. The filtrate was evaporated to a brown oil, which was dissolved in a mixture of hexanes and ethyl acetate (1:1 [v/v]. 100 mL). Silica gel (25 g, flash chromatography grade) was added to the brown solution, and the mixture was swirled well. The silica was removed by filtration on a glass frit, and washed three times with hexanes:ethyl acetate (1:1 [v/v], 50 mL portions). The silica gel was dried on the frit, and the combined filtrates were evaporated to dryness to afford a dark yellow liquid. The crude product (which was utilized for the following reaction) was found to contain some residual N,N-dimethylformamide.

$^1$H NMR (300 MHz, CHCl$_3$-d) δ3.94 (singlet, 3H, OCH$_3$), 4.32 (singlet, 2H, CH$_2$), 6.82 (doublet, J=8 Hz, 1H, ArH), 6.93 (singlet, 1H, ArH), 7.83 (doublet, J=8 Hz, 1H, ArH), 10.80 (singlet, 1H, OH). $^{13}$C NMR (75 MHz, CHCl$_3$-d) δ52.5, 54.3, 112.3, 117.0, 118.7, 130.8, 143.9, 162.1, 170.5.

Methyl 4-Aminomethylsalicylate Hydrochloride

Crude methyl 4-azidomethylsalicylate was dissolved in methanol (750 mL) in a 2 L Parr hydrogenation flask. Palladium on carbon catalyst (10% [w/w], 3.8 g) in water (25 mL) was added, followed by concentrated hydrochloric acid (35 mL). The flask was affixed to a Parr hydrogenator, and the mixture was shaken at room temperature under 40 psi of hydrogen for 16 hours. The reaction mixture was then filtered through a 0.45 mm nylon filter. The retained solid was then washed with methanol (150 mL), water (100 mL), and methanol again (150 mL). The combined filtrates were evaporated to dryness to afford a tan solid. This solid was dissolved in hot denatured ethanol (150 mL) and the solution was allowed to cool to room temperature. White crystals formed quickly. Finally, the mixture was then chilled for 16–18 hours at 4° C. to complete crystallization. The solid was filtered, washed with a little cold ethanol (50 mL) and then diethyl ether (150 mL), and dried in vacuo over potassium hydroxide pellets to afford 51.5 g (65% yield based on methyl 4-bromomethylsalicylate) of methyl 4-aminomethylsalicylate hydrochloride (m.p. 225°–227° C., open capillary, uncorrected).

$^1$H (300 MHz, DMSO-d$_6$) δ3.87 (singlet, 3H, OCH$_3$), 4.00 (singlet, 2H, CH$_2$), 7.06 (doublet, J=8 Hz, 1H, ArH), 7.13 (singlet, 1H, ArH), 7.77 (doublet, J=8 Hz, 1H, ArH), 8.59 (broad singlet, 3H, NH$_3$Cl), 10.55 (singlet, 1H, OH). $^{13}$C NMR (75 MHz, DMSO-d$_6$) δ41.6, 52.6, 113.0, 117.7, 119.8, 130.4, 142.1, 160.0, 169.1

Methyl 4-Succinylaminomethylsalicylate

Methyl 4-aminomethylsalicylate hydrochloride (3.00 g 13.8 mmoles) was suspended in dry pyridine (25 mL), and N,N-diisopropylethylamine (2.7 mL, 15.5 mmoles) was added. The suspension was stirred in an ice/water bath for 15 minutes, and then succinic anhydride (1.36 g, 13.6 mmoles) was added. The mixture was allowed to warm to room temperature, during which time the starting solids dissolved. After stirring for 2 hours, the mixture was evaporated to dryness, and the resulting solid was partitioned between ethyl acetate (300 mL) and 1M aqueous hydrochloric acid (100 mL). The layers were separated, and the ethyl acetate solution was washed with 1M hydrochloric acid (100 mL) and saturated aqueous sodium chloride (100 mL). The solution was dried over anhydrous sodium sulfate, filtered, and evaporated to dryness to yield a white solid. Finally, the solid was crystallized from ethyl acetate/hexanes, filtered, and dried in vacuo to afford 3.02 g (87% yield) of methyl 4-succinylaminomethylsalicylate (m.p. 161°–163° C.).

¹H NMR (300 MHz, DMSO-$d_6$) δ2.43 (triplet, J=6 Hz, 2H, $CH_2$CONH), 2.49 (triplet, J=6 Hz, 2H, $HO_2CCH_2$), 3.87 (singlet, 3H, $OCH_3$), 4.27 (doublet, J=6 Hz, 2H, $ArCH_2$NH), 6.83 (doublet, J=8 Hz, 1H, ArH), 6.86 (singlet, 1H, ArH), 7.71 (doublet, J=8 Hz, 1H, ArH), 8.43 (triplet, J=6 Hz, 1H, NH), 10.54 (singlet, 1H, OH), 12.12 (singlet, 1H, $CO_2$H). ¹³C NMR (75 MHz, DMSO-$d_6$) δ29.1, 30.1, 41.9, 52.5, 111.3, 115.6, 118.4, 130.1, 148.7, 160.7, 169.7, 171.7, 174.2.

Methyl 4-Succinylaminomethylsalicylate Succinimidyl Ester

Methyl 4-succinylaminomethylsalicylate (2.60 g, 10.2 mmoles) was dissolved in dry tetrahydrofuran (100 mL), and N-hydroxysuccinimide (1.29 g, 11.2 mmoles) and 1,3-di-cyclohexylcarbodiimide (2.10 g, 10.2 mmoles) were added. The mixture was stirred at room temperature under dry nitrogen, and the solids rapidly dissolved. After about 20 minutes, a white precipitate formed. The reaction mixture was stirred 16–18 hours, then chilled several hours at −20° C. The mixture was filtered cold, and the solid washed with a little tetrahydrofuran (25 mL). The combined filtrates were evaporated to dryness, and the residue was crystallized from ethyl acetate/hexanes, filtered, and dried in vacuo to afford 2.39 g (62% yield) of methyl 4-succinyl-aminomethylsalicylate succinimidyl ester (m.p. 133°–135° C.).

¹H NMR (300 MHz, DMSO-$d_6$) δ2.56 (triplet, J=7 Hz, 2H, $CH_2$CONH), 2.80 (singlet, 4H, $COCH_2CH_2CO$), 2.91 (triplet, J=7 Hz, 2H, $NO_2CCH_2$), 3.87 (singlet, 3H, $OCH_3$), 4.27 (doublet, J=6 Hz, 2H, $ArCH_2$NH), 6.83 (doublet, J=9 Hz, 1H, ArH), 6.84 (singlet, 1H, ArH), 7.71 (doublet, J=9 Hz, 1H, ArH), 8.51 (triplet, J=6 Hz, 1H, NH), 10.50 (singlet, 1H, OH). ¹³C NMR (75 MHz, DMSO-$d_6$) δ25.4, 25.9, 29.2, 41.8, 52.4, 111.4, 115.6, 118.4, 130.2, 148.2, 160.4, 168.9, 169.4, 170.2, 170.4.

EXAMPLE V

Preparation of a Reagent of General Formula I
Methyl (6-Aminohexanoyl)aminomethylsalicylate Hydrochloride

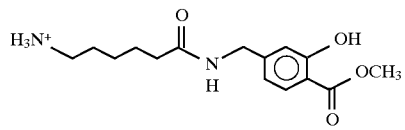

Methyl (N-tert-Butoxycarbonyl-6-aminohexanoyl) aminomethylsalicylate

Methyl 4-aminomethylsalicylate hydrochloride (2.25 g, 10.3 mmoles) was suspended in anhydrous N,N-dimethylformamide (30 mL), and N,N-diisopropylethylamine (3.6 mL, 20.7 mmoles) was added, followed by N-tert-butoxycarbonyl-6-aminohexanoic acid succinimidyl ester (3.38 g 10.3 mmoles). The mixture was stirred under dry nitrogen for 18 hours, during which time all solids dissolved. The solvent was then evaporated to leave a light brown syrup, which was partitioned between ethyl acetate (100 mL) and 1M aqueous hydrochloric acid (100 mL). The layers were separated, and the ethyl acetate solution was washed with saturated aqueous sodium bicarbonate (100 mL) and saturated aqueous sodium chloride (100 mL). The ethyl acetate solution was dried over anhydrous sodium sulfate, filtered, and evaporated to an amorphous off-white solid. The solid was crystallized form ethyl acetate/hexanes, filtered, and dried in vacuo to afford 3.25 g (80% yield) of methyl (N-tert-butoxycarbonyl-6-aminohexanoyl)aminomethylsalicylate (m.p. 120°–121° C., open capillary, uncorrected).

¹H NMR (300 MHz, DMSO-$d_6$) δ1.22 (multiplet, 2H, $NHCH_2CH_2CH_2CH_2CH_2$CO), 1.36 (multiplet, 2H, $CH_2CH_2$CO), 1.36 (singlet, 9H, $C(CH_3)_3$), 1.51 (multiplet, 2H, $NHCH_2CH_2$), 2.13 (triplet, J=7 Hz, 2H, $CH_2CH_2$CO), 2.87 (quartet, J=6 Hz, 2H, $NHCH_2CH_2$), 3.87 (singlet, 3H, $OCH_3$), 4.24 (doublet, J=6 Hz, 2H, $CH_2$Ar), 6.75 (triplet, J=6 Hz, 1H, $CONHCH_2CH_2$), 6.80 (doublet, J=8 Hz, 1H, ArH), 6.82 (singlet, 1H, ArH), 7.72 (doublet, J=8 Hz, 1H, ArH), 8.35 (triplet, J=6 Hz, 1H, $CONHCH_2$Ar), 10.53 (singlet, 1H, OH). ¹³C NMR (75 MHz, $CHCl_3$-d) δ25.0, 26.0, 28.2, 29.3, 35.3, 41.7, 52.4, 77.4, 111.2, 115.5, 118.3, 130.1, 148.7, 155.8, 160.5, 169.5, 172.6.

Methyl (6-Aminohexanoyl)aminomethylsalicylate Hydrochloride

Methyl (N-tert-butoxycarbonyl-6-aminohexanoyl) aminomethylsalicylate (3.00 g, 7.60 mmoles) was dissolved in ethyl acetate (100 mL), and dry hydrogen chloride was bubbled slowly through the solution. The reaction mixture warmed as the gas dissolved. After 5 minutes, the gas was shut off, and the solution was stirred at room temperature. A white precipitate formed in the solution. After 30 minutes, the reaction mixture was chilled in ice for 2 hours, then the solid was filtered, washed with diethyl ether (50 mL) and dried in vacuo over potassium hydroxide pellets to afford 2.50 g (99% yield) of methyl (6-aminohexanoyl) aminomethylsalicylate hydrochloride (decomposes with effervescence at 158°–160° C., open capillary, uncorrected).

¹H NMR (300 MHz, DMSO-$d_6$) δ1.28 (multiplet, 2H, $H_3CH_2CH_2CH_2CH_2CH_2$CO), 1.54 (multiplet, 4H, $NH_3CH_2CH_2CH_2CH_2CH_2$CO), 2.16 (triplet, J=8 Hz, 2H, $CH_2CH_2$CO), 2.71 (multiplet, 2H, $NH_3CH_2CH_2$), 3.85 (singlet, 3H, $OCH_3$), 4.22 (doublet, J=6 Hz, 2H, $CH_2$Ar), 6.80 (doublet, J=8 Hz, 1H, ArH), 6.83 (singlet, 1H, ArH), 7.70 (doublet, J=8 Hz, 1H, ArH), 8.10 (broad singlet, 3H, $NH_3$), 8.54 (triplet, J=6 Hz, 1H, $CONHCH_2$Ar), 10.35 (broad singlet, 1H, OH). ¹³C NMR (75 MHz, $CHCl_3$-d) δ24.8, 25.6, 26.7, 35.1, 41.7, 111.5, 115.6, 118.4, 130.2, 148.6, 160.4, 169.4.

EXAMPLE VI

Preparation of a Reagent of General Formula I
Cyanomethyl 4-Glutarylaminomethylsalicylate Succinimidyl Ester

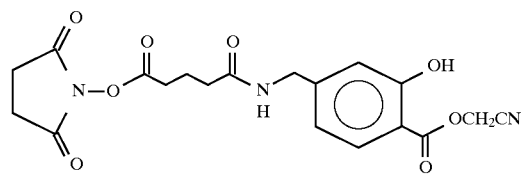

Methyl N-tert-Butoxycarbonylaminomethylsalicylate

Methyl 4-aminomethylsalicylate hydrochloride (10.9 g, 50 mmoles) was suspended in anhydrous methanol (200 mL) and di-tert-butyldicarbonate (10.9 g, 50 mmoles) and triethylamine (7.0 mL, 50 mmoles) were added. The solid rapidly dissolved with the slow evolution of gas. The reaction mixture was stirred at room temperature for 18 hours under dry nitrogen, then evaporated to dryness to afford a white amorphous mass. This mass was partitioned between ethyl acetate (200 mL) and water (100 mL). The layers were separated, and the ethyl acetate solution was dried over anhydrous sodium sulfate. The solution was filtered and evaporated to a white solid. This solid was crystallized from ethyl acetate/hexanes, filtered, and dried in vacuo to afford 13.7 g (97% yield) of methyl N-tertbutoxycarbonylaminomethyl-salicylate (m.p. 95°–96° C., open capillary, uncorrected).

$^1$H NMR (300 MHz, CHCl$_3$-d) δ1.42 (singlet, 9H, C(CH$_3$)$_3$), 3.90 (singlet, 3H, OCH$_3$), 4.26 (doublet, J=6 Hz, 2H, CH$_2$Ar), 4.99 (triplet, J=6H, 1H, NH), 6.75 (doublet, J=8 Hz, 1H, ArH), 6.84 (singlet, 1H, ArH), 7.73 (doublet, J=8 Hz, 1H, ArH), 10.72 (singlet, 1H, OH). $^{13}$C NMR (75 MHz, CHCl$_3$-d) δ28.5, 44.4, 52.4, 80.0, 111.5, 115.9, 118.2, 130.5, 150.0, 156.3, 162.1, 170.8.

N-tert-Butoxycarbonylaminomethylsalicylic acid

Methyl N-tert-butoxycarbonylaminomethylsalicylate (8.7 g, 30.9 mmoles) was dissolved in dry tetrahydrofuran (100 mL), and potassium trimethylsilanolate (4.4 g, 30.9 mmoles, 90% pure) was added. The yellow solution was refluxed for 24 hours, during which time a tan precipitate formed and the solvent turned light brown. The mixture was evaporated to dryness, and the solid was dissolved in cold water (100 mL). The brown solution was chilled in an ice bath, and saturated aqueous potassium hydrogen sulfate solution was used to titrate the stirred solution to pH 2–3. An off-white solid precipitated during the titration. The solid was filtered, washed with cold water, and dried in vacuo over potassium hydroxide to afford 6.7 g, (81% yield) of crude N-tert-butoxycarbonylaminomethylsalicylic acid (m.p. 141°–144° C., decomposes with effervescence on melting, open capillary, uncorrected).

$^1$H NMR (300 MHz, CHCl$_3$-d) δ1.47 (singlet, 9H, C(CH$_3$)$_3$), 4.33 (doublet, J=6 Hz, 2H, CH$_2$Ar), 5.07 (triplet, J=6H, 1H, NH), 6.80 (doublet, J=8 Hz, 1H, ArH), 6.88 (singlet, 1H, ArH), 7.81 (doublet, J=8 Hz, 1H, ArH), 10.72 (broad singlet, 2H, OH and CO$_2$H). $^{13}$C NMR (75 MHz, CHCl$_3$-d) δ28.5, 44.4, 80.5, 111.1, 115.9, 118.3, 131.5, 148.5, 156.6, 162.6, 174.1.

Cyanomethyl N-tert-Butoxycarbonylaminomethylsalicylate

N-tert-Butoxycarbonylamino-methylsalicylic acid (8.2 g, 30.6 mmoles) was suspended in chloroacetonitrile (25 mL), and triethylamine (4.3 mL, 30.6 mmoles) was added. The mixture was stirred under dry nitrogen at 50° C., and the solids dissolved. The solution was stirred 18 hours, and then cooled to room temperature. The solvent was evaporated, and the residue was partitioned between ethyl acetate (250 mL) and water (250 mL). The layers were separated, and the ethyl acetate layer was washed with saturated aqueous sodium bicarbonate (100 mL) and saturated aqueous sodium chloride (100 mL). The solution was dried over anhydrous sodium sulfate, filtered, and evaporated to dryness. The residual pale tan solid was dissolved in ethyl acetate (100 mL), and silica gel (10 g, flash chromatography grade) was added. The mixture was swirled well and allowed to sit for five minutes at room temperature. The silica was removed by filtration on a glass frit, and washed with ethyl acetate (100 mL). The filtrate was evaporated to dryness. The solid residue was crystallized from ethyl acetate/hexanes to afford 7.9 g (88% yield) of cyanomethyl N-tert-butoxycarbonylaminomethylsalicylate (m.p. 144°–146° C., open capillary, uncorrected).

$^1$H NMR (300 MHz, CHCl$_3$-d) δ1.45 (singlet, 9H, C(CH$_3$)$_3$), 4.30 (doublet, J=6 Hz, 2H, CH$_2$Ar), 5.00 (singlet, 2H, OCH$_2$CN), 5.05 (triplet, J=6H, 1H, NH), 6.83 (doublet, J=8 Hz, 1H, ArH), 6.91 (singlet, 1H, ArH), 7.77 (doublet, J=8 Hz, 1H, ArH), 10.12 (singlet, 1H, OH). $^{13}$C NMR (75 MHz, CHCl$_3$-d) δ28.4, 44.3, 49.0, 80.1, 109.6, 114.2, 116.1, 118.7, 130.5, 149.7, 156.2, 162.5, 168.5.

Cyanomethyl Aminomethylsalicylate Hydrochloride

Cyanomethyl N-tert-butoxycarbonylaminomethylsalicylate (7.7 g, 26.2 mmoles) was dissolved in tetrahydrofuran (150 mL), and dry hydrogen chloride was bubbled slowly through the solution. The reaction mixture warmed as the gas dissolved. After 5 minutes, the gas was shut off, and the solution was stirred at room temperature. A thick, creamy white precipitate formed in the solution. After 30 minutes, the reaction mixture was chilled in ice for 2 hours, then the solid was filtered, washed with diethyl ether (100 mL) and dried in vacuo over potassium hydroxide pellets to afford 5.8 g (91% yield) of cyanomethyl aminomethylsalicylate hydrochloride (m.p. darkens at 210° C., decomposes at 228° C., open capillary, uncorrected).

$^1$H NMR (300 MHz, DMSO-d6) δ4.00 (singlet, 2H, CH$_2$Ar), 5.20 (singlet, 2H, OCH$_2$CN), 7.05 (doublet, J=8 Hz, 1H, ArH), 7.15 (singlet, 1H, ArH), 7.75 (doublet, J=8 Hz, 1H, ArH), 8.62 (broad singlet, 3H, NH$_3$), 10.38 (singlet, 1H, OH). $^{13}$C NMR (75 MHz, DMSO-d6) δ41.6, 49.7, 113.0, 116.1, 118.0, 119.7, 131.1, 142.3, 159.5, 166.1.

Cyanomethyl 4-Glutarylaminomethylsalicylate

Cyanomethyl 4-aminomethylsalicylate hydrochloride (1.22 g, 5.0 mmoles) was suspended in dry dichloromethane (100 mL), and the suspension was stirred in an ice/water bath. A solution of glutaric anhydride (0.57 g, 5.0 mmoles) and triethylamine (0.7 mL, 5.0 mmoles) in dry dichloromethane (25 mL) was then added dropwise over 15 minutes. The mixture was allowed to warm to room temperature, and the reaction was stirred for 18 hours. The mixture was evaporated to dryness, and the resulting solid was triturated under cold 0.1M aqueous hydrochloric acid (50 mL). The solid was collected by filtration, washed with cold water, and dried in vacuo over potassium hydroxide pellets to afford 1.43 g (89% yield) of cyanomethyl 4-glutarylaminomethylsalicylate (m.p. 125°–126° C.).

$^1$H NMR (300 MHz, DMSO-d$_6$) δ1.75 (quintet, J=7 Hz, 2H, CH$_2$CH$_2$CH$_2$), 2.19 (triplet, J=7 Hz, 2H, CH$_2$CONH), 2.22 (triplet, J=7 Hz, 2H, HO$_2$CCH$_2$), 4.24 (doublet, J=6 Hz, 2H, ArCH$_2$NH), 5.17 (singlet, 2H, OCH$_2$CN), 6.81 (doublet, J=8 Hz, 1H, ArH), 6.85 (singlet, 1H, ArH), 7.70 (doublet, J=8 Hz, 1H, ArH), 8.39 (triplet, J=6 Hz, 1H, NH), 10.5 (very broad singlet, 1H, OH), 11.7 (very broad singlet, 1H, CO$_2$H). $^{13}$C NMR (75 MHz, DMSO-d$_6$) δ20.7, 33.1, 34.5, 41.8, 49.7, 111.2, 115.9, 116.2, 118.5, 130.9, 149.1, 160.2, 166.6, 172.3, 174.5.

Cyanomethyl 4-Glutarylaminomethy salicylate Succinimidyl Ester

Cyanomethyl 4-glutarylaminomethylsalicylate (1.00 g, 3.1 mmoles) was dissolved in dry tetrahydrofuran (50 mL), and N-hydroxysuccinimide (0.36 g, 3.1 mmoles) and 1,3-dicyclohexylcarbodiimide (0.64 g, 3.1 mmoles) were added. The mixture was stirred at room temperature under dry nitrogen, and the solids rapidly dissolved. After about 60 minutes, a white precipitate formed. The reaction mixture was stirred 24 hours, then chilled several hours at −20° C. The mixture was filtered cold, and the solid washed with a little tetrahydrofuran (10 mL). The combined filtrates were evaporated to dryness, and the residue was crystallized from ethyl acetate/hexanes, filtered, and dried in vacuo to afford 1.04 g (80% yield) of cyanomethyl 4-glutarylaminomethylsalicylate succinimidyl ester (m.p. 116°–119° C.).

$^1$H NMR (300 MHz, DMSO-d$_6$) δ1.88 (quintet, J=7 Hz, 2H, CH$_2$CH$_2$CH$_2$), 2.30 (triplet, J=7 Hz, 2H, CH$_2$CONH), 2.71 (triplet, J=7 Hz, 2H, NO$_2$CCH$_2$), 2.80 (singlet, 4H, COCH$_2$CH$_2$CO), 4.26 (doublet, J=6 Hz, 2H, ArCH$_2$NH), 5.18 (singlet, 2H, OCH$_2$CN), 6.82 (doublet, J=8 Hz, 1H, ArH), 6.86 (singlet, 1H, ArH), 7.71 (doublet, J=8 Hz, 1H, ArH), 8.44 (triplet, J=6 Hz, 1H, NH), 10.18 (broad singlet, 1H, OH). $^{13}$C NMR (75 MHz, DMSO-d$_6$) δ20.4, 25.5, 29.7, 33.6, 41.8, 49.6, 111.2, 115.9, 116.2, 118.4, 130.9, 148.9, 160.1, 166.5, 169.0, 170.5, 171.7.

EXAMPLE VII

Preparation of a Reagent of General Formula I Cyanomethyl 4-(6-maleimidohexanoyl) aminomethylsalicylate

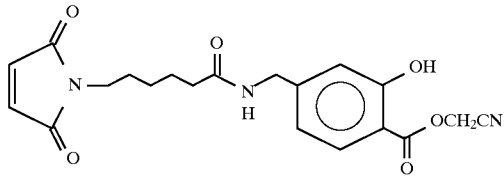

Cyanomethyl 4-(6-maleimidohexanoyl) aminomethylsalicylate

Cyanomethyl 4-aminomethylsalicylate hydrochloride (79 mg, 0.32 mmoles) and 6-maleimidocaproic acid N-hydroxysuccinimide ester (100 mg, 0.32 mmoles) were suspended in dry N,N-dimethylformamide (5.0 mL), and the suspension was stirred at room temperature. N,N-diisopropylethylamine (87 µL, 0.50 mmoles) was added. The solids rapidly dissolved to afford a clear, pale yellow solution. After 30 minutes, the mixture was evaporated to dryness, and the residue was partitioned between ethyl acetate (25 mL) and cold 0.1M aqueous hydrochloric acid (25 mL). The layers were separated, and the ethyl acetate solution washed with saturated aqueous sodium bicarbonate (25 mL) and saturated aqueous sodium chloride (25 mL). The ethyl acetate solution was dried over anhydrous sodium sulfate, filtered and evaporated to a white solid. The solid was crystallized from ethyl acetate/hexanes to afford 108 mg (84% yield) of cyanomethyl 4-(6-maleimidohexanoyl) aminomethyl salicylate (m.p. 141°–144° C.).

$^1$H NMR (300 MHz, DMSO-$d_6$) δ1.20 (multiplet, 2H, CH$_2$CH$_2$CH$_2$CH$_2$CH$_2$), 1.53 (multiplet, 4H, CH$_2$CH$_2$CH$_2$CH$_2$CH$_2$), 2.13 (triplet, J=7 Hz, 2H, NCH$_2$CH$_2$), 3.38 (triplet, J=7 Hz, 2H, CH$_2$CH$_2$CO), 4.26 (doublet, J=6 Hz, 2H, ArCH$_2$NH), 5.02 (singlet, 2H, OCH$_2$CN), 6.68 (singlet, 2H, CH=CH), 6.76 (doublet, J=8 Hz, 1H, ArH), 6.80 (singlet, 1H, ArH), 7.69 (doublet, J=8 Hz, 1H, ArH), 7.99 (triplet, J=6 Hz, 1H, NH), 10.04 (singlet, 1H, OH). $^{13}$C NMR (75 MHz, DMSO-$d_6$) δ24.5, 25.7, 27.6, 35.2, 36.9, 41.9, 48.8, 109.1, 114.3, 115.6, 118.2, 129.8, 133.8, 149.2, 161.2, 167.6, 170.4, 172.7.

EXAMPLE VIII

Preparation of a Reagent of General Formula I Cyanomethyl 4-(3-(2-Pyridyldithio)propionyl) aminomethylsalicylate

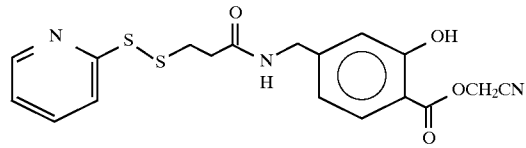

Cyanomethyl 4-(3-(2-pyridyldithio)propionyl) aminomethylsalicylate

Cyanomethyl 4-aminomethylsalicylate hydrochloride (79 mg, 0.32 mmoles) and 3-(2-pyridyldithio)propionic acid N-hydroxysuccinimide ester (100 mg, 0.32 mmoles) were suspended in dry N,N-dimethylformamide (5.0 mL), and the suspension was stirred at room temperature. N,N-Diisopropylethylamine (87 µL, 0.50 mmoles) was added. The solids rapidly dissolved to give a clear, pale tan solution. After 30 minutes, the mixture was evaporated to dryness, and the residue was partitioned between ethyl acetate (25 mL) and cold 0.1M aqueous hydrochloric acid (25 mL). The layers were separated and the ethyl acetate solution washed with saturated aqueous sodium bicarbonate (25 mL) and saturated aqueous sodium chloride (25 mL). The ethyl acetate solution was dried over anhydrous sodium sulfate, filtered and evaporated to a clear oil. Trituration under cold hexanes afforded 64 mg (48% yield) of a gum of cyanomethyl 4-(3-(2-pyridyldithio)propionyl) aminomethylsalicylate.

$^1$H NMR (300 MHz, DMSO-$d_6$) δ2.60 (triplet, J=7 Hz, 2H, SCH$_2$CH$_2$), 3.05 (triplet, J=7 Hz, 2H, CH$_2$CH$_2$CO), 4.27 (doublet, J=6 Hz, 2H, ArCH$_2$NH), 5.19 (singlet, 2H, OCH$_2$CN), 6.84 (doublet, J=8 Hz, 1H, ArH), 6.88 (singlet, 1H, ArH), 7.23 (triplet, J=6 Hz, 1H, ArH), 7.71 (doublet, J=8 Hz, 1H, ArH), 7.74–7.82 (multiplet, 2H, ArH), 8.44 (doublet, J=6 Hz, 1H, ArH), 8.56 (triplet, J=6 Hz, 1H, NH), 10.13 (broad singlet, 1H, OH). $^{13}$C NMR (75 MHz, DMSO-$d_6$) δ34.0, 34.5, 41.8, 49.6, 54.9, 111.2, 115.9, 116.0, 118.4, 119.3, 121.3, 130.8, 137.9, 148.6, 149.7, 159.4, 160.0, 166.4, 170.3.

EXAMPLE IX

Preparation of a Reagent of General Formula III 4-Glutarylaminomethylsalicylhydroxamic Acid Hydrazide

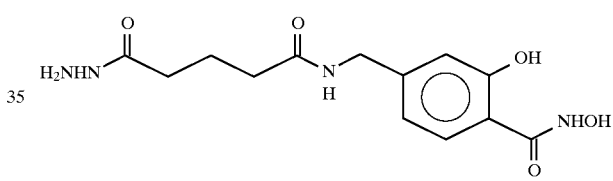

Methyl 4-Glutarylaminomethylsalicylate N-tert-Butyloxycarbonylhydrazide

Methyl 4-glutarylaminomethylsalicylate succinimidyl ester (2.57 g, 6.8 mmoles) [prepared as for the succinyl derivative above, substituting glutaric anhydride for succinic anhydride] was dissolved in dry tetrahydrofuran (100 mL), and tert-butylcarbazate (0.90 g, 6.8 mmoles) was added. The reaction was stirred at room temperature for 60 hours. The solution was then evaporated to dryness, and the residue dissolved in ethyl acetate (100 mL). The ethyl acetate solution was washed with saturated aqueous potassium bicarbonate (100 mL) and saturated aqueous sodium chloride (100 mL). It was then dried over anhydrous sodium sulfate, filtered, and evaporated to dryness. The residue was crystallized by dissolving it in ethyl acetate (50 mL) with gentle warming, adding hexanes (50 mL) to the warm solution, and chilling at −20° C. Once crystallization began, another portion of hexanes (50 mL) was added, and the mixture was chilled for 18 hours at −20° C. Finally, the solid was filtered, washed with hexanes:ethyl acetate (2:1 [v/v], 90 mL), and dried in vacuo to afford 2.51 g (90% yield) of methyl 4-glutarylaminomethylsalicylate N-tert-butyloxycarbonylhydrazide (m.p. 68°–72° C., open capillary, uncorrected).

$^1$H NMR (300 MHz, DMSO-$d_6$) δ1.37 (singlet, 9H, (CH$_3$)$_3$C), 1.74 (quintet, J=7 Hz, 2H, CH$_2$CH$_2$CH$_2$), 2.07 (triplet, J=7 Hz, 2H, CH$_2$CONHCH$_2$), 2.17 (triplet, J=7 Hz, 2H, HNHNOCCH$_2$), 3.86 (singlet, 3H, OCH$_3$), 4.23

(doublet, J=6 Hz, 2H, ArCH₂NH), 6.80 (doublet, J=8 Hz, 1H, ArH), 6.82 (singlet, 1H, ArH), 7.71 (doublet, J=8 Hz, 1H, ArH), 8.37 (triplet, J=6 Hz, 1H, NH), 8.65 (singlet, 1H, NHNHCOCH₂), 9.48 (singslet, 1H, OCONHNH), 10.50 (singlet, 1H, OH). ¹³C NMR (75 MHz, DMSO-d₆) δ21.2, 28.0, 32.6, 34.6, 41.7, 52.4, 79.1, 111.4, 115.5, 118.3, 130.2, 148.5, 155.5, 160.4, 169.4, 171.7, 172.1.

4-Glutarylaminomethylsalicylhydroxamic Acid N-tert-Butyloxycarbonylhydrazide

Methyl 4-glutarylaminomethylsalicylate N-tert-butyloxycarbonylhydrazide (2.00 g, 4.9 mmoles) was added to a cooled (ice/water bath) solution of hydroxylamine sulfate (0.82 g, 5.0 mmoles), sodium hydroxide (1.00 g, 25.0 mmoles) and sodium sulfite (0.20 g, mmoles) in water (25 mL). The suspension was stirred for 18 hours in the dark, allowing it to warm to room temperature. The solution was then filtered to remove some insoluble material, and the pale yellow solution was chilled in an ice/water bath. The cold reaction mixture was slowly titrated to pH 3–4 with cold sulfuric acid (25% [v/v] aqueous), during which time a gummy material precipitated. The mixture was then chilled several hours in ice, and the liquid was decanted. The remaining amorphous solid was dissolved in methanol (25 mL), filtered, and evaporated to a white foam. The foam was dried in vacuo to 1.86 g (94% yield) of crude 4-glutarylaminomethylsalicylhydroxamic acid N- tert-butyloxycarbonylhydrazide.

¹H NMR (300 MHz, DMSO-d₆) δ1.37 (singlet, 9H, (CH₃)₃C), 1.74 (quintet, J=7 Hz, 2H, CH₂CH₂CH₂), 2.10 (triplet, J=7 Hz, 2H, CH₂CONHCH₂), 2.16 (triplet, J=7 Hz, 2H, HNHNOCCH₂), 4.20 (doublet, J=6 Hz, 2H, ArCH₂NH), 6.71 (doublet, J=8 Hz, 1H, ArH), 6.74 (singslet, 1H, ArH), 7.60 (doublet, J=8 Hz, 1H, ArH), 8.32 (triplet, J=6 Hz, 1H, NH), 8.65 (singlet, 1H, NHNHCOCH₂), 9.29 (broad singlet, 1H, NHOH), 9.48 (singlet, 1H, OCONHNH), 11.37 (broad singlet, 1H, ArOH), 12.32 (broad singlet, 1H, NHOH). ¹³C NMR (75 MHz, DMSO-d₆) δ21.2, 28.0, 32.6, 34.6, 41.7, 79.1, 112.4, 115.6, 117.6, 127.1, 145.9, 155.6, 159.8, 166.5, 171.7, 172.1.

4-Glutarylaminomethylsalicylhydroxamic Acid Hydrazide Hydrochloride

4-Glutarylaminomethylsalicylhydroxamic acid N-tert-butyloxycarbonyl hydrazide (1.86 g, 4.6 mmoles) was dissolved in dry tetrahydrofuran (100 mL), and dry hydrogen chloride was bubbled slowly through the solution. The reaction mixture warmed as the gas dissolved. After 5 minutes, the gas was shut off, and the solution was stirred at room temperature. A white precipitate formed in the solution. After 30 minutes, the reaction mixture was chilled in ice for 2 hours, then the solid was filtered, washed with diethyl ether (50 mL) and dried in vacuo over potassium hydroxide pellets to afford 1.51 g (95% yield) of 4-glutarylaminomethylsalicylhydroxamic acid hydrazide hydrochloride (m.p. shrinks at 65° C., decomposes with effervescence at 100° C., open capillary, uncorrected).

¹H NMR (300 MHz, DMSO-d₆) δ1.72 (quintet, J=7 Hz, 2H, CH₂CH₂CH₂), 2.17 (triplet, J=7 Hz, 2H, CH₂CONHCH₂), 2.23 (triplet, J=7 Hz, 2H, H₃NHNOCCH₂), 4.17 doublet, J=6 Hz, 2H, ArCH₂NH), 6.69 (doublet, J=8 Hz, 1H, ArH), 6.74 (singlet, 1H, ArH), 7.66 (doublet, J=8 Hz, 1H, ArH), 8.49 (triplet, J=6 Hz, 1H, NH), 10.49 (broad singlet, 4H, NH₃NHCOCH₂), 11.08 (broad singlet, 1H, ArOH), 11.43 (broad singlet, 2H, NHOH). ¹³C NMR (75 MHz, DMSO-d₆) δ21.0, 25.2, 32.3, 34.4, 41.8, 67.2, 112.6, 115.7, 117.7, 127.4, 145.9, 159.8, 166.5, 171.7, 172.1.

EXAMPLE X

Preparation Of A Reagent Of General Formula III 4-Glutarylaminomethylsalicyl(O-methyl)hydroxamic Acid Succinimidyl Ester

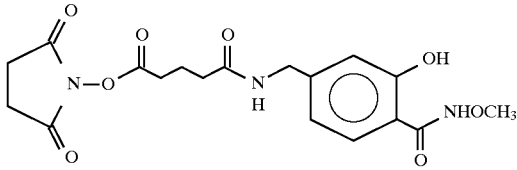

Methyl N-(Benzyloxycarbonyl)-4-aminomethylsalicylate

Methyl 4-aminomethylsalicylate hydrochloride (5.04 g 23.2 mmoles) was suspended in chloroform (80 mL) and N,N-diisopropylethylamine (4.10 mL, 23.5 mmoles) and N-(benzyloxycarbonyloxy)succinimide (6.48 g, 26.0 mmoles) were added. The reaction mixture was stirred at room temperature for 4 hours, during which time all solids dissolved. The reaction mixture was then extracted with 1N aqueous hydrochloric acid (100 mL), water (75 mL), and saturated aqueous sodium chloride (50 mL). The chloroform solution was dried over anhydrous magnesium sulfate, filtered and evaporated to dryness to give a white solid. The product was crystallized from ethyl acetate:hexanes to afford 6.17 g (84% yield) of methyl N-(benzyloxycarbonyl)-4-aminomethylsalicylate (m.p. 91°–92° C., open capillary, uncorrected).

¹H NMR (300 MHz, DMSO-d₆) δ3.86 (singlet, 3H, OCH₃), 4.21 (doublet, J=6 Hz, 2H, NHCH₂), 5.05 (singlet, 2H, CH₂O), 6.82 (doublet, J=8 Hz, 1H, ArH), 6.86 (singlet, 1H, ArH), 7.27–7.36 (multiplet, 5H, ArH), 7.72 (doublet, J=8 Hz, 1H, ArH), 7.90 (triplet, J=6 Hz, 1H, NH), 10.53 (singlet, 1H, OH). ¹³C NMR (75 MHz, DMSO-d₆) δ43.5, 52.4, 65.6, 111.5, 115.4, 118.2, 127.9, 128.0, 128.5, 130.2, 137.3, 148.6, 156.7, 160.5, 169.5.

Methyl N-(Benzyloxycarbonyl)-4-aminomethyl-2-O-benzylsalicylate

Methyl N-(benzyloxycarbonyl)-4-aminomethylsalicylate (6.06 g, 19.2 mmoles) was dissolved in acetone (150 mL), and benzyl bromide (2.60 mL, 21.9 mmoles) and anhydrous potassium carbonate (13.28 g, 96.1 mmoles) were added. The mixture was stirred and heated at reflux for 22 hours. The mixture was concentrated to remove most of the acetone, and ethyl acetate (100 mL) was added. Aqueous hydrochloric acid (1N, 200 mL) was added slowly, swirling frequently to dissolve the solid carbonate. The layers were separated, and the aqueous layer was extracted with ethyl acetate (50 mL). The ethyl acetate solutions were combined and washed with water (100 mL) and saturated aqueous sodium chloride (50 mL), dried over anhydrous magnesium sulfate, filtered, and concentrated to about 50 mL. This solution was heated to boiling, and hexanes (150 mL) were added. The solution was cooled in ice, and crystals slowly formed. The crystals were collected by filtration, washed with hexanes, and dried in vacuo to afford 6.97 g (89% yield) of methyl N-(benzyloxycarbonyl)-4-aminomethyl-2-O-benzylsalicylate (m.p. 106°–107° C., open capillary, uncorrected).

¹H NMR (300 MHz, DMSO-d₆) δ3.78 (singlet, 3H, OCH₃), 4.27 (doublet, J=6 Hz, 2H, NHCH₂), 5.07 (singlet, 2H, CH₂OCO), 5.15 (singlet, 2H, CH₂O), 6.94 (doublet, J=8 Hz, 1H, ArH), 7.16 (singlet, 1H, ArH), 7.26–7.42 (multiplet, 8H, ArH), 7.49–7.51 (multiplet, 2H, ArH), 7.68 (doublet, J=8 Hz, 1H, ArH), 7.90 (triplet, J=6 Hz, 1H, NH). ¹³C NMR (75 MHz, DMSO-d₆) δ43.8, 51.8, 65.6, 69.7, 112.5, 112.6, 118.9, 119.0, 127.2, 127.9, 128.0, 128.5 (2 carbons), 131.3, 137.0, 137.3, 146.2, 156.7, 157.8, 166.1.

N-(Benzyloxycarbonyl)-4-aminomethyl-2-O-benzylsalicylic acid

Methyl N-(benzyloxycarbonyl)-4-aminomethyl-2-O-benzylsalicylate (6.81 g, 16.8 mmoles) was dissolved in tetrahydrofuran (50 mL). A solution of lithium hydroxide monohydrate (0.78 g, 18.5 mmoles) in water (25 mL) was added, and the reaction mixture was stirred and heated at 75° C. for 24 hours. The solution was cooled, and 1N aqueous hydrochloric acid (50 mL) was added. The reaction mixture was extracted twice with ethyl acetate (150 mL then 50 mL). The combined ethyl acetate extracts were washed with water (75 mL) and saturated aqueous sodium chloride (50 mL), dried over anhydrous magnesium sulfate, filtered, and concentrated to 150 mL. The ethyl acetate solution was heated to boiling, and hexanes (150 mL) was added. The solution was cooled in ice, and crystals formed. The crystals were collected by filtration, washed with hexanes, and dried in vacuo to afford 5.92 g (90% yield) of N-(benzyloxycarbonyl)-4-aminomethyl-2-O-benzylsalicylic acid (m.p. 139°–140° C., open capillary, uncorrected).

$^1$H NMR (300 MHz, DMSO-$d_6$) δ4.23 (doublet, J=6 Hz, 2H, NHCH$_2$), 5.06 (singlet, 2H, CH$_2$OCO), 5.13 (singlet, 2H, CH$_2$O), 6.90 (doublet, J=8 Hz, 1H, ArH), 7.11 singlet, 1H, ArH), 7.28–7.40 (multiplet, 8H, ArH), 7.48–7.51 (multiplet, 2H, ArH), 7.64 (doublet, J=8 Hz, 1H, ArH), 7.88 (triplet, J=6 Hz, 1H, NH), 12.57 (singet, 1H, COOH). $^{13}$C NMR (75 MHz, DMSO-$d_6$) δ43.8, 65.6, 69.8, 112.5 (2 carbons), 118.9, 120.4, 127.4, 127.9, 128.0, 128.5 (2 carbons), 131.2. 137.1, 137.4, 145.6, 156.7, 157.5, 167.4.

N-(Benzyloxycarbonyl)-4-aminomethyl-2-O-benzylsalicyl(O-methyl)hydroxamic acid

N-(Benzyloxycarbonyl)-4-aminomethyl-2-O-benzylsalicylic acid (3.07 g 7.84 mmoles) was dissolved in anhydrous N,N-dimethylformamide (75 mL) under dry nitrogen. After cooling the solution to in an ice/water bath, triethylamine (2.20 mL, 15.8 mmoles) was added followed by isobutyl chloroformate (1.10 mL, 8.48 mmoles). The reaction was stirred in ice for 1.5 hours. Methoxylamine hydrochloride (0.67 g, 8.02 mmoles) was added and the reaction mixture was allowed to warm to room temperature. After 3 hours, the reaction was diluted with ethyl acetate (150 mL) and extracted with 1N aqueous hydrochloric acid (100 mL), water (100 mL), and saturated aqueous sodium chloride (50 mL). The ethyl acetate solution was dried over anhydrous magnesium sulfate, filtered and concentrated to about 50 mL. This solution was boiled and hexanes (100 mL) were added. Upon cooling in an ice bath, crystals formed quickly. They were collected by filtration and washed with hexane to afford 2.87 g (87% yield) of N-(benzyloxycarbonyl)-4-aminomethyl-2-O-benzylsalicyl (O-methyl)hydroxamic acid (m.p. 116°–117° C., open capillary, uncorrected).

$^1$H NMR (300 MHz, DMSO-$d_6$) δ3.63 (singlet, 3H, NHOCH$_3$), 4.20 (doublet, J=6 Hz, 2H, NHCH$_2$), 5.04 (singlet, 2H, CH$_2$OCO), 5.13 (singlet, 2H, CH$_2$O), 6.90 (doublet, J=8 Hz, 1H, ArH), 7.08 (singlet, 1H, ArH), 7.29–7.49 (multiplet, 11H, ArH), 7.88 (triplet, J=6 Hz, 1H, NH), 11.13 (singlet, 1H, NHOCH$_3$). $^{13}$C NMR (75 MHz, DMSO-$d_6$) δ43.7, 63.2, 65.5, 69.8, 111.8, 119.2, 121.7, 127.6, 127.9, 128.0, 128.1, 128.5 (2 carbons), 129.8, 136.8, 137.3, 144.3, 155.9, 156.6, 163.3.

4-Aminomethylsalicyl(O-methyl)hydroxamic Acid Hydrochloride

N-(Benzyloxycarbonyl)-4-aminomethyl-2-O-benzylsalicyl(O-methyl)hydroxamic acid (1.42 g, 3.38 mmoles) and palladium on carbon (0.10 g, 10% [w/w]) were placed in a IL hydrogenation flask under dry nitrogen. Ethanol (150 mL) was added, followed by concentrated aqueous hydrochloric acid (0.30 mL). The flask was affixed to the Parr hydrogenator and shaken under 35 psi of hydrogen for 7 hours at room temperature. The reaction mixture was then filtered through Celite to remove the catalyst, and the filtrate was concentrated until a precipitate began to form. The mixture was cooled in ice, the solid collected by filtration, washed with hexanes, and dried in vacuo to afford 0.65 g (83% yield) of 4-aminomethyl-salicyl(O-methyl) hydroxamic acid hydrochloride (m.p. >250° C., open capillary, uncorrected).

$^1$H NMR (300 MHz, DMSO-$d_6$) δ3.71 (singlet, 3H, NHOCH$_3$), 3.95 (singlet, 2H, NH$_3$CH$_2$), 7.00 (doublet, J=8 Hz, 1H, ArH), 7.05 (singlet, 1H, ArH), 7.72 (doublet, J=8 Hz, H, ArH), 8.53 (broad singlet, 3H, NH$_3$),12.01 (broad singlet, 2H, NHOCH$_3$ and OH). $^{13}$C NMR (75 MHz, DMSO-$d_6$) δ41.7, 63.6, 114.2, 117.6, 119.3, 128.2, 140.0, 159.4, 166.1.

4-Glutarylaminomethylsalicyl(O-methyl)hydroxamic Acid Succinimidyl Ester

4-Aminomethylsalicyl(O-methyl)hydroxamic acid hydrochloride (0.57 g, 1,82 mmoles) was dissolved in anhydrous N,N-dimethylformamide (10 mL), and N,N-diisopropylethyl amine (0.35 mL, 2.01 mmoles) and glutaric anhydride (0.23 g, 2.02 mmoles) were added. The mixture was stirred at room temperature for 26 hours, and then N-hydroxysuccinimide (0.23 g, 2.00 mmoles) and 1,3-dicyclohexylcarbodiimide (0.42 g, 2.01 mmoles) were added. The reaction mixture was stirred for an additional 24 hours at room temperature. The mixture was then filtered and diluted with ethyl acetate (100 mL). The ethyl acetate solution was washed with 1N aqueous hydrochloric acid (100 mL), water (100 mL), and saturated aqueous sodium chloride (50 mL). The solution was then dried over anhydrous magnesium sulfate, filtered, and evaporated to dryness. The crude gummy product was triturated under a mixture of ethyl acetate and diethyl ether to produce a solid which was filtered and dried in vacuo to afford 0.15 g (20% yield) of 4-glutarylaminomethylsalicyl(O-methyl) hydroxamic acid succinimidyl ester (m.p. 121°–124° C., open capillary, uncorrected).

$^1$H NMR (300 MHz, DMSO-$d_6$) δ1.85 (quintet, J=7 Hz, 2H, CH$_2$CH$_2$CH$_2$), 2.27 (triplet, J=7 Hz, 2H, CH$_2$CONHCH$_2$), 2.69 (triplet, J=7 Hz, 2H, NOCCH$_2$), 2.80 (singlet, 4H, COCH$_2$CH$_2$CO), 3.70 (singlet, 3H, NHOCH$_3$), 4.21 (doublet, J=6 Hz, 2H, NHCH$_2$), 2.27 (doublet, J=8 Hz, 1H, ArH), 6.77 (singlet, 1H, ArH), 7.57 (doublet, J=8 Hz, H, ArH), 8.39 (triplet, J=6 Hz, 1H, NHCH$_2$), 11.75 (singlet, 1H, OH), 11.78 (singlet, 1H, NHOCH$_3$). $^{13}$C NMR (75 MHz, DMSO-$d_6$) δ20.4, 25.4, 29.7, 33.4, 33.6, 41.7, 112.8, 115.6, 117.8, 127.8, 146.2, 159.3, 166.3, 169.0, 170.5, 171.5.

EXAMPLE XI

Preparation Of A Reagent Of General Formula III
4-(3-(2-Pyridyldithio)propionyl)aminomethylsalicyl
(O-methyl)hydroxamic Acid

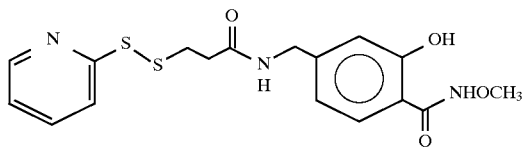

4-(3-(2-Pyridyldithio)propionyl)aminomethylsalicyl(O-methyl)hydroxamic Acid 3-(2-Pyridyldithio)propionic acid N-hydroxysuccinimide ester (100 mg, 0.32 (mmole) was dissolved in dry N,N-dimethylformamide (5.0 L) and N,N-diisopropylethylamine (65 μL, 0.36 mmole) was added followed by 4-aminomethylsalicyl(O-methyl)hydroxamic acid hydrochloride (82 mg, 0.35 mmole). The reaction was stirred for 6 hours at room temperature. The solvent was evaporated in vacuo, and the residue was chromatographed on silica gel eluting with dichloromethane/methanol/acetic acid (95:5:1 [v/v/v]). Fractions containing the desired product were pooled and evaporated to an oil to afford 44 mg (35% yield) of 4-(3-(2-pyridyldithio)propionyl)aminomethylsalicyl(O-methyl)hydroxamic acid.

$^1$H NMR (300 MHz, DMSO-$d_6$) δ2.58 (triplet, J=7 Hz, 2H, CH$_2$CH$_2$ S), 3.04 (triplet, J=7 Hz, 2H, COCH$_2$CH$_2$), 3.70 (singlet, 3H, OCH$_3$), 4.23 (doublet, J=6 Hz, 2H, ArCH$_2$NH), 6.76 (doublet, J=8 Hz, 1H, ArH), 6.79 (singlet, 1H, ArH), 7.23 (triplet, J=6 Hz, 1H, ArH), 7.57 (doublet, J=8 Hz, 1H, ArH), 7.73–7.82 (multiplet, 2H, ArH), 8.44 (doublet, J=6 Hz, 1H, ArH), 8.4 (triplet, J=6 Hz, 1H, NH), 11.80 (broad singlet, 2H, OH and NHO). $^{13}$C NMR (75 MHz, DMSO-$d_6$) δ34.1, 34.5, 41.8, 63.5, 112.7, 115.7, 117.8, 119.3, 121.3, 127.7, 138.0, 145.9, 149.8, 159.4 166.3, 170.2, 172.8.

PHENYLBORONIC ACID COMPLEXING REAGENTS AND CONJUGATES DERIVED FROM 4-AMINOMETHYL-2,6-DIHYDROXYBENZOIC ACID

A two-step process which utilizes reagents of General Formula CIII for the preparation of bioconjugates is summarized in FIG. 1'. Initially, a reagent of General Formula CIII is selected that is comprised of an appropriate reactive electrophilic or nucleophic group $R_1$ suitable for reaction with the desired biologically active species.

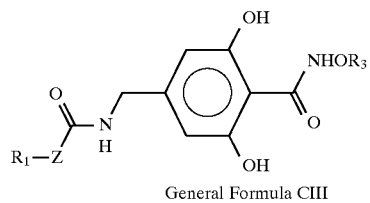

General Formula CIII

Group $R_1$ is a reactive electrophilic or nucleophilic moiety suitable for reaction of the phenylboronic acid complexing reagent with a bioactive species. Group $R_1$ is preferably selected from, but not limited to, acrylamide, bromo, dithiopyridyl, bromoacetamide, hydrazide, N-hydroxysuccinimidyl ester, N-hydroxysulfosuccinimidyl ester, imidate ester, imidazolide, iodo, iodoacetamide, maleimide, amino and thiol moieties.

Group Z is a spacer selected from a saturated or unsaturated, preferably unbranched, chain of from about 0 to 6 carbon equivalents in length, an unbranched saturated or unsaturated chain of from about 6 to 18 carbon equivalents in length with at least one of intermediate amide or disulfide moieties, and a polyethylene glycol chain of from about 3 to 12 carbon equivalents in length. Group Z is preferably selected from an unbranched alkyl chain of general formula (CH$_2$)$_n$, wherein n=1 to 6.

Group $R_3$ is selected from one of an H, an alkyl, and a methylene or ethylene moiety with an electronegative substituent.

Group $R_3$ is preferably selected from one of H, CH$_3$, CH$_2$CN, CH$_2$COOH, CH$_2$CONH$_2$, CH$_2$CH$_2$OH and CH$_2$OCH$_3$. When group $R_3$ is H, group $R_1$ is preferably selected from one of acrylamide, amino, dithiopyridyl, hydrazide, imidate ester, maleimide, and thiol moieties.

The reagent of General Formula CIII is condensed with the bioactive species to yield a conjugate of General Formula CIV:

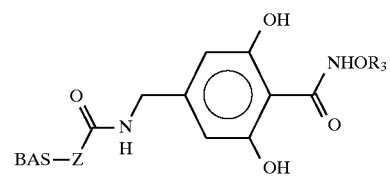

General Formula CIV wherein groups Z and BAS are as defined above, and $R_3$ is selected from one of an H, an alkyl, and a methylene or ethylene moiety with an electronegative substituent.

The conjugate of General Formula CIV is then complexed with a phenylboronic acid conjugate having the general formula of General Formula CV:

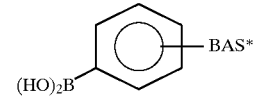

General Formula CV wherein the symbol labeled BAS* represents a second biologically active species, that may include a linker portion and differ from the biologically active species labeled BAS of the complexing reagent. The BAS* may also include a portion of a reactive moiety used to attach the bioactive species to the phenylboronic acid reagent. The complexation yields the stereoisomeric complex (tetrahedral boron) of General Formula CVI:

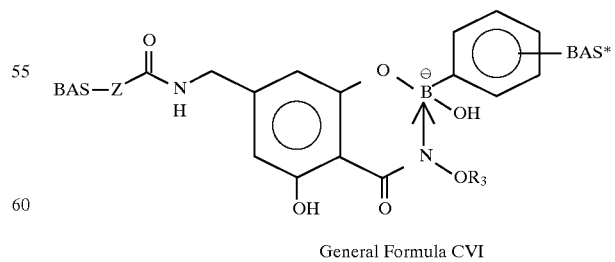

General Formula CVI

An alternative three-step process which utilizes reagents of General Formula CI for the preparation of bioconjugates is also summarized in FIG. 1'. Initially, a reagent of General Formula CI is selected that is comprised of an appropriate reactive electrophilic or nucleophic group $R_1$ suitable for reaction with the desired biologically active species.

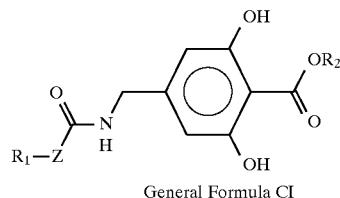

General Formula CI

Group $R_1$ is a reactive electrophilic or nucleophilic moiety suitable for reaction of the putative phenylboronic acid complexing reagent with a bioactive species. Group $R_1$ is preferably selected from, but not limited to, acrylamide, bromo, dithiopyridyl, bromoacetamide, hydrazide, N-hydroxysuccinimidyl ester, N-hydroxysulfosuccinimidyl ester, imidate ester, imidazolide, iodo, iodoacetamide, maleimide, amino and thiol moieties.

Group Z is a spacer selected from a saturated or unsaturated, preferably unbranched, chain of from about 0 to 6 carbon equivalents in length, an unbranched saturated or unsaturated chain of from about 6 to 18 carbon equivalents in length with at least one of intermediate amide or disulfide moieties, and a polyethylene glycol chain of from about 3 to 12 carbon equivalents in length. Group Z is preferably selected from an unbranched alkyl chain of general formula $(CH)_n$, wherein n=1 to 6.

Group $R_2$ is selected from an alkyl (e.g., methyl, ethyl, etc.) and a methylene or ethylene bearing an electronegative substituent. An electronegative substituent is a substituent with a negative dipole moment, e.g., CN, COOH, etc. Group $R_2$ is preferably selected from one of $CH_3$, $CH_2CH_3$, $CH_2CN$, $CH_2COOH$, $CH_2CONH_2$ and $CH_2OCH_3$.

The next step in a three-step process in the preparation of bioconjugates is to condense the appropriate reagent with the bioactive species to yield a conjugate of General Formula CII:

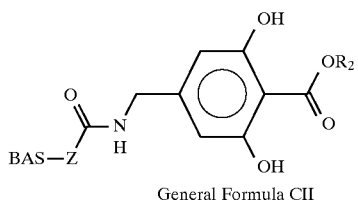

General Formula CII

In General Formula CII, Z, BAS and $R_2$ are as defined above.

Next, the conjugate is reacted with a hydroxylamine derivative of the general formula $NH_2OR_3$, wherein $R_3$ is selected from either an H, an alkyl (e.g., methyl, ethyl, etc.), or a methylene or ethylene with an electronegative moiety. Suitable hydroxylamine derivatives include, but not limited to, $NH_2OH$, $NH_2OCH_3$, $NH_2OCH_2CN$, $NH_2OCH_2COOH$, $NH_2OCH_2CONH_2$ and $NH_2OCH_2CH_2OH$. The resulting conjugate has the general formula of General Formula CIV:

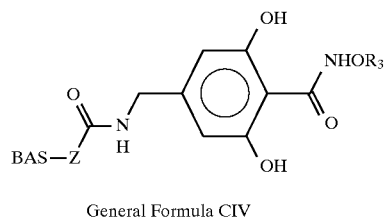

General Formula CIV

In General Formula CIV, Groups Z and BAS are as defined above, and $R_3$ is selected from one of an H, an alkyl, and a methylene or ethylene moiety with an electronegative substituent.

The conjugate of General Formula CIV is then complexed with a phenylboronic acid having the general formula of General Formula CV:

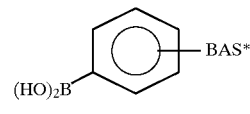

General Formula CV wherein the symbol labeled BAS* represents a second biologically active species, that may include a linker portion and differ from the biologically active species labeled BAS of the complexing reagent. The BAS* may also include a portion of a reactive moiety used to attach the bioactive species to the phenylboronic acid reagent. The complexation yields the stereoisomeric complex (about tetrahedral boron) of General Formula CVI:

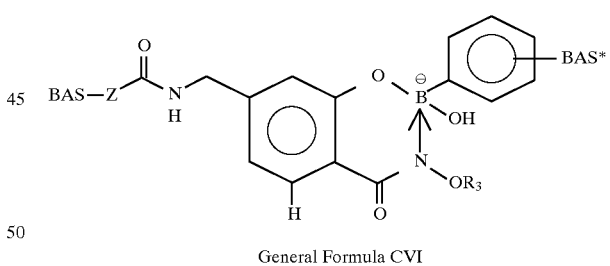

General Formula CVI

It will be appreciated by one of the ordinary skill in the art, upon reference to this disclosure, that the various syntheses described above in the previous section (concerning reagents and conjugates derived from 4 or 5 aminomethyl-salicylic acid and shown in FIGS. 1 through 7) may be utilized where appropriate for the corresponding synthesis of the reagents shown in FIGS. 1'–7' and/or described in this section. For example, the techniques for adding Z groups and R1 group from the previous section may be considered for use in preparing the reagents shown in FIGS. 1'–7' and/or described in this section.

SYNTHESIS OF PHENYLBORONIC ACID COMPLEXING REAGENTS OF GENERAL FORMULA CIII

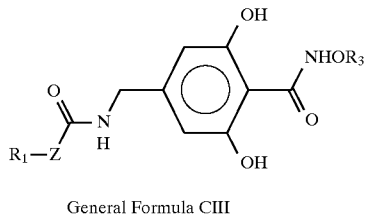

General Formula CIII

Reagents of General Formula CIII are derived from 2,6-dihydroxy-4-methylbenzoic acid. In each instance, the reagent is ultimately prepared from a synthetic intermediate which is an alkyl 4-aminomethyl-2,6-dihydroxybenzoate.

FIG. 2' summarizes the preparation of alkyl 4-aminomethyl-2,6-dihydroxybenzoates, synthetic intermediates leading to reagents of General Formula CI, wherein $R_2$ is an alkyl group, e.g., methyl, ethyl, etc. Initially, in step 1, an alkyl 2,6-dihydroxy-4-methylbenzoate is acetylated to reduce the reactivity of the ring system toward bromination, affording the corresponding alkyl 2,6-diacetoxy-4-methylbenzoate. In step 2, the ester is brominated with N-bromosuccinimide and benzoyl peroxide catalyst to afford the corresponding benzyl bromide. In step 3, the benzyl bromide is alkylated with sodium azide to afford the corresponding benzyl azide. In step 4, the benzyl azide is subjected to palladium catalyzed hydrogenation in the presence of HCl to afford the corresponding benzyl amine hydrochloride. Finally, in step 5, the acetoxy protecting groups are removed by acid catalyzed methanolysis.

FIG. 4' summarizes the preparation of 4-aminomethyl-2,6-dihydroxybenzohydroxamic acids, synthetic intermediates leading to reagents of General Formula CIII, wherein group $R_3$ is one of an alkyl or methylene or ethylene bearing an electronegative substituent. Initially, in step 1, an alkyl 4-aminomethyl-2,6-dihydroxybenzoate, prepared as summarized in FIG. 2', is condensed with N-(benzyloxycarbonyl)oxy succinimide to afford the alkyl N-benzyloxycarbonyl protected 4-aminomethyl-2,6-dihydroxybenzoate. In step 2, the phenolic hydroxyl moieties are condensed with benzyl bromide to afford the further protected benzyl diether intermediate. In step 3, the alkyl ester is selectively cleaved by reaction with LiOH to afford the corresponding benzoic acid. In step 4, the benzoic acid is activated by reaction with isobutylchloroformate to form a mixed anhydride which is subsequently reacted with a hydroxylamine derivative preferably selected from, but not limited to, either $NH_2OH$, $NH_2OCH_3$, $NH_2OCH_2CN$, $NH_2OCH_2COOH$, $NH_2OCH_2CONH_2$, $NH_2OCH_2CH_2OH$ and $NH_2OCH_2OCH_3$ to afford the corresponding protected hydroxamic acid. Finally, in step 5, both the amine and phenolic hydroxyl moieties are simultaneously deprotected by palladium catalyzed hydrogenation in the presence of HCl to afford the corresponding 4-aminomethyl-2,6-dihydroxybenzohydroxamic acid hydrochloride.

Another reagent of the present invention, which is the acrylic acid amide of 4-aminomethyl 2,6 dihydroxybenzo hydroxamic acid, can be prepared in a single step, using the end product of FIG. 4', by condensing acrylic acid anhydride or acryloyl chloride with 4 aminomethyl 2, 6 dihydroxybenzo hydroxamic acid, provided that $R_3$ is not H.

FIG. 5' summarizes the synthesis of reagents of General Formula CIII, wherein group $R_3$ is preferably selected from one of H, $CH_3$, and a methylene or ethylene moiety with an electronegative substituent, and wherein group $R_1$ is selected from either imidazolide, hydrazide and N-hydroxysuccinimidyl ester moieties. These reagents are each prepared by a two-step process in which an aliphatic acid anhydride is utilized in the first step. Initially, a 4-aminomethyl-2,6-dihydroxybenzohydroxamic acid, prepared as summarized in FIG. 4', is condensed of an aliphatic acid anhydride preferably selected from, but not limited to, either succinic anhydride, glutaric anhydride, maleic anhydride and glycolic acid anhydride, in an aprotic organic solvent, which results in the introduction of a spacer (group Z) having a free terminal carboxylic acid moiety. In the case where the aliphatic acid anhydride is maleic anhydride in this condensation reaction, the resulting Z group is unsaturated as it contains an alkene group. Subsequently, the carboxylic acid moiety is further functionalized by reaction with either N,N-carbonyldiimidazole, isobutylchloroformate and tert-butyl carbazate, or N,N-dicyclohexyl-carbodiimide and N-hydroxysuccinimide to afford the corresponding imidazolide, protected hydrazide and N-hydroxysuccinimidyl ester, respectively. In the instance of the protected hydrazide, the N-(tert-butoxycarbonyl) protecting group is removed by contacting the reagent with anhydrous hydrochloric acid.

FIG. 6' summarizes the synthesis of reagents of General Formula CIII, wherein group $R_3$ is preferably selected from one of H, $CH_3$, and a methylene or ethylene moiety with an electronegative substituent, and wherein group $R_1$ is selected from either bromo, chloro, maleimide, dithiopyridyl and imidate ester moieties. Reagents of General Formula CIII, wherein group $R_1$ is selected from either bromo and chloro moieties, are prepared by condensing a 4-aminomethyl-2,6-dihydroxybenzohydroxamic acid, prepared as summarized in FIG. 4', with either bromoacetic acid anhydride or chloroacetic acid anhydride, respectively. The homologous iodo reagent is prepared by halogen exchange of the chloro reagent with sodium iodide. Reagents of General Formula CIII, wherein $R_1$ is selected from either bromo, chloro, iodo, bromoacetamide, chloroacetamide and iodoacetamide moieties, may not be conveniently prepared when $R_3$ is H, due to the potential for intermolecular alkylation of the unprotected hydroxamate. Reagents of General Formula CIII, wherein group $R_1$ is selected from either maleimide and dithiopyridyl moieties, are prepared by condensing a 4-aminomethyl-2,6-dihydroxybenzohydroxamic acid, prepared as summarized in FIG. 4', with an N-hydroxysuccinimidyl ester of an aliphatic carboxylic ester which bears either a terminal maleimide or dithiopyridyl moiety. Reagents of General Formula CIII, wherein $R_1$ is an imidate ester moiety, are prepared by a two-step process in which a 4-aminomethyl-2,6-dihydroxybenzohydroxamic acid, prepared as summarized in FIG. 4', is first condensed with an N-hydroxysuccinimidyl ester of an aliphatic carboxylic ester which bears a terminal nitrile moiety. Subsequently, the nitrile moiety is converted to the methyl imidate ester by reaction with anhydrous hydrogen chloride in methanol at 0° C.

Reagents of General Formula CIII, wherein group $R_1$ is selected from either N-hydroxysuccinimidyl ester and dithiopyridyl moieties may be utilized as synthetic intermediates to prepare reagents of General Formula CIII, wherein group Z is an unbranched saturated or unsaturated chain with at least one of intermediate amide or disulfide moieties.

Reagents of General Formula CIII, wherein group $R_1$ is an N-hydroxysuccinimidyl ester moieties, may be condensed with compounds having primary aliphatic amine moieties of the general formula $R_1—Z_2—NH_2$, wherein $Z_2$ is an unbranched saturated or unsaturated chain preferably of from about 1 to 5 carbon equivalents in length, to afford reagents of General Formula CIII, wherein group Z is an unbranched saturated or unsaturated chain with at least one of intermediate amide moieties.

Alternatively, N-hydroxysuccinimidyl ester reagents of General Formula CIII, preferably derived from a dicarboxylic acid selected from either succinic acid, maleic acid, fumaric acid, acetylenedicarboxylic acid and glutaric acid, may be condensed with compounds having primary aliphatic amine moieties of the general formula $HO2C—Z_2—NH_2$, wherein $Z_2$ is an unbranched saturated or unsaturated chain preferably of from about 1 to 5 carbon equivalents in length, preferably selected from, either glycine, β-alanine, amniopropiolic acid, 4-amino-butyric acid and 6-aminocaproic acid, to afford compounds having free terminal carboxylic acid moieties which may be further functionalized in accordance with FIG. 5' to afford reagents of General Formula CIII, wherein Z is an unbranched saturated or unsaturated chain with at least one of intermediate amide moieties. This process is summarized for in FIG. 7' for the synthesis of a reagent of General Formula CIII, wherein $R_1$ is an N-hydroxysuccinimidyl ester, and wherein Z is an unbranched saturated or unsaturated chain with at least one of an intermediate amide moiety.

Reagents of General Formula CIII, wherein group $R_1$ is a dithiopyridyl moiety, may be condensed with compounds having terminal thiol moieties of the general formula $R_1—Z_2—SH$, wherein $Z_2$ is an unbranched saturated or unsaturated chain preferably of from about 1 to 5 carbon equivalents in length, to afford reagents of General Formula CIII, wherein group Z is an unbranched saturated or unsaturated chain with at least one of intermediate disulfide moieties.

Alternatively, dithiopyridyl reagents of General Formula CIII, preferably derived from a mercaptocarboxylic acid selected from either mercaptoacetic acid, β-mercaptopropionic acid, mercaptopropiolic acid, 4-mercaptobutyric acid and 6-mercaptocaproic acid, may be condensed with compounds having a terminal thiol moiety of the general formula $HO_2C—Z_2—SH$, wherein $Z_2$ is an unbranched saturated or unsaturated chain preferably of from about 1 to 5 carbon equivalents in length, preferably selected from either mercaptoacetic acid, β-mercaptopropionic acid, mercaptopropiolic acid, 4-mercaptobutyric acid and 6-mercaptocaproic acid, to afford compounds having free terminal carboxylic acid moieties which may be further functionalized in accordance with FIG. 5' to afford reagents of General Formula CIII, wherein group Z is an unbranched saturated or unsaturated chain with at least one of intermediate disulfide moieties. This process is summarized in FIG. 7' for the synthesis of a reagent of General Formula CIII, wherein $R_1$ is an N-hydroxysuccinimidyl ester, and wherein Z is an unbranched saturated or unsaturated chain with at least one of a intermediate disulfide moiety.

Reagents of General Formula CIII, wherein group Z is a polyethylene glycol chain of from about 3 to 12 carbon equivalents in length, are prepared by condensing a 4-aminomethyl-2,6-dihydroxybenzohydroxamic acid, prepared as summarized in FIG. 4', with a polyethylene glycol reagent having both an N-hydroxysuccinimidyl ester moiety and either a reactive electrophilic or nucleophilic moiety (or a protected precursor thereof), many of which are commercially available, to afford reagents of General Formula CIII, wherein group Z is a polyethylene glycol chain of from about 3 to 12 carbon equivalents in length.

SYNTHESIS OF PUTATIVE PHENYLBORONIC ACID COMPLEXING REAGENTS OF GENERAL FORMULA CI

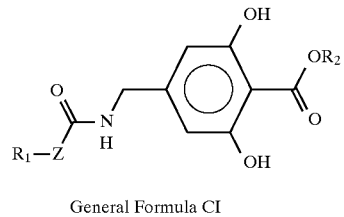

General Formula CI

Reagents of General Formula CI are derived from alkyl 2,6-dihydroxy-4-methylbenzoates. FIG. 2' summarizes the preparation of alkyl 4-aminomethyl-2,6-dihydroxybenzoates, synthetic intermediates leading to reagents of General Formula CI, wherein $R_2$ is an alkyl group, e.g., methyl, ethyl, etc. FIG. 2' shows an example where $R_2$ is a methyl group. Initially, in step 1, an alkyl 2,6-dihydroxy-4-methylbenzoate is acetylated to reduce the reactivity of the ring system toward bromination, affording the corresponding alkyl 2,6-diacetoxy-4-methylbenzoate. In step 2, the ester is brominated with N-bromosuccinimide and benzoyl peroxide catalyst to afford the corresponding benzyl bromide. In step 3, the benzyl bromide is alkylated with sodium azide to afford the corresponding benzyl azide. In step 4, the benzyl azide is subjected to palladium catalyzed hydrogenation in the presence of HCl to afford the corresponding benzyl amine hydrochloride. Finally, in step 5, the acetoxy protecting groups are removed by acid catalyzed methanolysis.

FIG. 3' summarizes the preparation of synthetic intermediates leading to reagents of General Formula CI, wherein group $R_2$ is a methylene bearing an electronegative substituent, for example, carboxymethyl, acetamidomethyl and cyanomethyl 4-aminomethyl-2,6-dihydroxybenzoate. It is to be appreciated that other contemplated substituents for group $R_2$ may be prepared by a similar synthesis. Initially, in step 1, the alkyl 4-aminomethyl-2,6-dihydroxy-benzoate, prepared as summarized in FIG. 2', is reacted with di-tert-butyl dicarbonate and triethylamine in methanol to afford the corresponding protected alkyl N-(tert-butoxycarbonyl) aminomethylbenzoate. In step 2, the alkyl ester is cleaved by reaction with potassium trimethylsilanolate and worked up in aqueous acid to afford the corresponding benzoic acid. In step 3, the benzoic acid is alkylated by reaction with either an α-haloacid, α-haloacetamide or α-haloacetonitrile and triethylamine to afford the corresponding carboxymethyl, acetamido-methyl or cyanomethyl ester, respectively. Finally, in step 4, the N-(tert-butoxycarbonyl) protecting group is removed by reaction with anhydrous HCl in tetrahydrofuran to afford an alkyl 4-aminomethyl-2,6-dihydroxybenzoate hydrochloride.

FIG. 5' summarizes the synthesis of reagents of General Formula CI, wherein group $R_2$ is one of either an alkyl or a methylene or ethylene bearing an electronegative substituent, and wherein group $R_1$ is selected from either imidazolide, hydrazide and N-hydroxysuccinimidyl ester moieties. These reagents are each prepared by a two-step process in which an aliphatic acid anhydride is utilized in the first step. Initially, an alkyl 4-aminomethyl-2,6-dihydroxybenzoate, prepared as summarized in either FIG.

2' or FIG. 3', is condensed of an aliphatic acid anhydride preferably selected from, but not limited to, either succinic anhydride, glutaric anhydride, maleic anhydride and glycolic acid anhydride, in an aprotic organic solvent, which results in the introduction of a spacer (group Z) having a free terminal carboxylic acid moiety. Subsequently, the carboxylic acid moiety is further functionalized by reaction with either N,N-carbonyldiimidazole, isobutylchloroformate and tert-butyl carbazate, or N,N-dicyclohexylcarbodiimide and N-hydroxysuccinimide to afford the corresponding imidazolide, protected hydrazide and N-hydroxysuccinimidyl ester, respectively. In the instance of the protected hydrazide, the N-(tert-butoxycarbonyl) protecting group is removed by contacting the reagent with anhydrous hydrochloric acid.

FIG. 6' summarizes the synthesis of reagents of General Formula CI, wherein group $R_2$ is one of either an alkyl or a methylene or ethylene bearing an electronegative substituent, and wherein group $R_1$ is selected from either bromo, chloro, maleimide, dithiopyridyl and imidate ester moieties. Reagents of General Formula CI, wherein group $R_1$ is selected from either bromo and chloro moieties, are prepared by condensing an alkyl 4-aminomethyl-2,6-dihydroxy-benzoate, prepared as summarized in either FIG. 2' or FIG. 3', with either bromoacetic acid anhydride or chloroacetic acid anhydride, respectively. The homologous iodo reagent is prepared by halogen exchange of the chloro reagent with sodium iodide. Reagents of General Formula CI, wherein $R_1$ is selected from either bromo, chloro, iodo, bromoacetamide, chloroacetamide and iodoacetamide moieties, may not be conveniently prepared when $R_3$ is H, due to the potential for intermolecular alkylation of the unprotected hydroxamate. Reagents of General Formula CI, wherein group $R_1$ is selected from either maleimide and dithiopyridyl moieties, are prepared by condensing an alkyl 4-aminomethyl-2,6-dihydroxybenzoate, prepared as summarized in either FIG. 2' or FIG. 3', with an N-hydroxysuccinimidyl ester of an aliphatic carboxylic ester which bears either a terminal maleimide or dithiopyridyl moiety. Reagents of General Formula CI, wherein $R_1$ is an imidate ester moiety, are prepared by a two-step process in which an alkyl 4-aminomethyl-2,6-dihydroxybenzoate, prepared as summarized in either FIG. 2' or FIG. 3', is first condensed with an N-hydroxysuccinimidyl ester of an aliphatic carboxylic ester which bears a terminal nitrile moiety. Subsequently, the nitrile moiety is converted to the methyl imidate ester by reaction with anhydrous hydrochloric acid in methanol at 0° C.

Reagents of General Formula CI, wherein group $R_1$ is selected from either dithiopyridyl, imidazolide and N-hydroxysuccinimidyl ester moieties may be utilized as synthetic intermediates to prepare reagents of General Formula CI, wherein group Z is an unbranched saturated or unsaturated chain with at least one of intermediate amide or disulfide moieties.

Reagents of General Formula CI, wherein group $R_1$ is selected from either N-hydroxysuccinimidyl ester and dithiopyridyl moieties may be utilized as synthetic intermediates to prepare reagents of General Formula CI, wherein group Z is an unbranched saturated or unsaturated chain with at least one of intermediate amide or disulfide moieties.

Reagents of General Formula CI, wherein group $R_1$ is an N-hydroxysuccinimidyl ester moieties, may be condensed with compounds having primary aliphatic amine moieties of the general formula $R_1$—$Z_2$—$NH_2$, wherein $Z_2$ is an unbranched saturated or unsaturated chain preferably of from about 1 to 5 carbon equivalents in length, to afford reagents of General Formula CI, wherein group Z is an unbranched saturated or unsaturated chain with at least one of intermediate amide moieties.

Alternatively, N-hydroxysuccinimidyl ester reagents of General Formula CI, preferably derived from a dicarboxylic acid selected from either succinic acid, maleic acid, fumaric acid, acetylenedicarboxylic acid and glutaric acid, may be condensed with compounds having primary aliphatic amine moieties of the general formula $HO_2C$—$Z_2$—$NH_2$, wherein $Z_2$ is an unbranched saturated or unsaturated chain preferably of from about 1 to 5 carbon equivalents in length, preferably selected from, either glycine, β-alanine, amniopropiolic acid, 4-amino-butyric acid and 6-aminocaproic acid, to afford compounds having free terminal carboxylic acid moieties which may be further functionalized in accordance with FIG. 5' to afford reagents of General Formula CI, wherein Z is an unbranched saturated or unsaturated chain with at least one of intermediate amide moieties. This process is summarized for in FIG. 7' for the synthesis of a reagent of General Formula CI, wherein $R_1$ is an N-hydroxysuccinimidyl ester, and wherein Z is an unbranched saturated or unsaturated chain with at least one of an intermediate amide moiety.

Reagents of General Formula CI, wherein group $R_1$ is a dithiopyridyl moiety, may be condensed with compounds having terminal thiol moieties of the general formula $R_1$—$Z_2$—SH, wherein $Z_2$ is an unbranched saturated or unsaturated chain preferably of from about 1 to 5 carbon equivalents in length, to afford reagents of General Formula CI, wherein group Z is an unbranched saturated or unsaturated chain with at least one of intermediate disulfide moieties.

Alternatively, dithiopyridyl reagents of General Formula CI, preferably derived from a mercaptocarboxylic acid selected from either mercaptoacetic acid, β-mercaptopropionic acid, mercaptopropiolic acid, 4-mercaptobutyric acid and 6-mercaptocaproic acid, may be condensed with compounds having a terminal thiol moiety of the general formula $HO_2C$—$Z_2$—SH, wherein $Z_2$ is an unbranched saturated or unsaturated chain preferably of from about 1 to 5 carbon equivalents in length, preferably selected from either mercaptoacetic acid, β-mercaptopropionic acid, mercaptopropiolic acid, 4-mercaptobutyric acid and 6-mercaptocaproic acid, to afford compounds having free terminal carboxylic acid moieties which may be further functionalized in accordance with FIG. 5' to afford reagents of General Formula CI, wherein group Z is an unbranched saturated or unsaturated chain with at least one of intermediate disulfide moieties. This process is summarized in FIG. 7' for the synthesis of a reagent of General Formula CI, wherein $R_1$ is an N-hydroxysuccinimidyl ester, and wherein Z is an unbranched saturated or unsaturated chain with at least one of a intermediate disulfide moiety.

Reagents of General Formula CI, wherein group Z is a polyethylene glycol chain of from about 3 to 12 carbon equivalents in length, are prepared by condensing an alkyl 4-aminomethyl-2,6-dihydroxybenzoate, prepared as summarized in either FIG. 2' or FIG. 3', with a polyethylene glycol reagent having both an N-hydroxysuccinimidyl ester moiety and either a reactive electrophilic or nucleophilic moiety (or a protected precursor thereof), many of which are commercially available, to afford reagents of General Formula CI, wherein group Z is a polyethylene glycol chain of from about 3 to 12 carbon equivalents in length.

PREPARATION OF PHENYLBORONIC ACID COMPLEXING CONJUGATES OF GENERAL FORMULA CIV

At this point, phenylboronic acid complexing reagents of General Formula CIII may be reacted with a suitable biologically active species to yield the conjugate of the general formula of General Formula CIV:

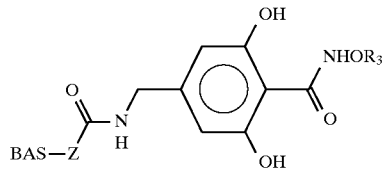

General Formula CIV

Alternatively, the putative phenylboronic acid complexing reagents of General Formula CI may be reacted with a suitable biologically active species to yield the conjugate of the general formula of General Formula CII:

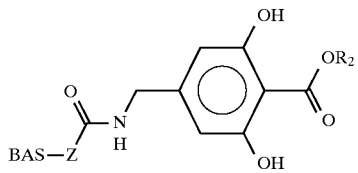

General Formula CII

The conjugate of General Formula CII is next condensed with a hydroxylamine derivative to yield the corresponding phenylboronic acid complexing conjugate of the general formula of General Formula CIV:

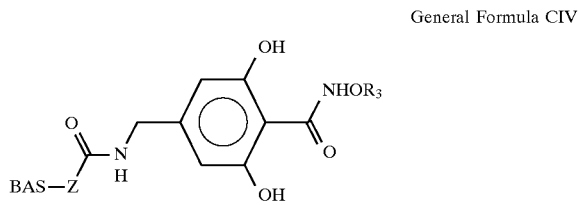

General Formula CIV

Suitable hydroxylamine derivatives are preferably selected from, but not limited to, $NH_2OH$, $NH_2OCH_3$, $NH_2OCH_2CN$, $NH_2OCH_2COOH$, $NH_2OCH_2CONH_2$, $NH_2OCH_2CH_2OH$, $NH_2OCH_2OCH_3$. When group $R_2$ in General Formula CII is an alkyl group, $NH_2OH$ is preferably utilized to effect the interconversion of General Formula CII to General Formula CIV.

PREPARATION OF BIOCONJUGATES OF GENERAL FORMULA CVI

Bioconjugates of General Formula CVI may be prepared in buffered aqueous solutions or organic solvents. Preferred buffers include acetate, citrate, phosphate, carbonate and diglycine. Borate buffers should be avoided due to their ability to complex with the phenylboronic acid complexing moiety. Tris, β-hydroxyamine and β-hydroxyacid buffers should be avoided due to their ability to complex with the phenylboronic acid. The bioconjugate is formed within a few minutes over a range of temperatures of from about 4° C. to 70° C. The stability of the bioconjugate in aqueous solution at a given pH and temperature is influenced, to some extent, by substituent group $R_3$. Bioconjugates of General Formula CVI are stable in aqueous solutions of approximate pH greater than 2.5 and less than 12.5. The bioconjugation reaction (phenylboronic acid complexation) is insensitive to significant variations in ionic strength over the range 0.01 to 1M, the presence of organic solvents including acetonitrile, methanol, ethanol, isopropanol, butanol, N,N-dimethylformamide and dimethylsulfoxide, the presence of detergents, and the presence of chaotropic agents (protein denaturants) including urea, guanidine hydrochloride, guanidine thiocyanate and formamide, which are incompatible with prior art indirect labeling systems wherein the structure of a biological macromolecule must be maintained to preserve requisite binding properties. Once formed, the bioconjugates are stable upon removal of water, and can be lyophilized for storage.

The stability of the bioconjugate at a given pH is determined to some extent by substituent group $R_3$. Phenylboronic acid complexes of General Formula CVI, wherein group $R_3$ is H, are stable in buffered aqueous solutions over the approximate pH range 2.5 to 12.5. Phenylboronic acid complexes of General Formula CVI, wherein group $R_3$ is $CH_3$, are stable in buffered aqueous solutions over the approximate pH range 3.5 to 12.5. Phenylboronic acid complexes of General Formula CVI, wherein group $R_3$ includes an electronegative moiety, are stable in buffered aqueous solutions over the approximate pH range less than 2.5 to 12.5.

The stability of the phenylboronic acid complex toward acid catalyzed hydrolysis is related to the $pK_a$ of the hydroxamic acid participating in the complex. The lower the $pK_a$ of the hydroxamic acid moiety the more stable the complex. Consequently, phenylboronic acid complexes of General Formula CVI wherein group $R_3$ is an electronegative moiety exhibit greater stability toward acid catalyzed hydrolysis than do those in which $R_3$ is either H or $CH_3$.

It should be appreciated that the pH stability associated with bioconjugates of General Formula CVI, derived from 4-aminomethyl-2,6-dihydroxybenzohydroxamic acid, is significantly better than that of bioconjugates of General Formula VI, derived from either 4- or 5-aminomethylsalicylhydroxamic acid, with respect to both acid and base catalyzed hydrolysis.

The following examples present a detailed description of the synthesis of reagents of General Formula CI and General Formula CIII.

EXAMPLE CI

Preparation of Methyl 4-Aminomethyl-2,6-dihydroxybenzoate Hydrochloride

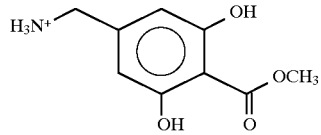

Methyl 4-Methyl-2,6-diacetoxybenzoate.

Methyl 4-methyl-2,6-dihydroxybenzoate (14.0 grams, 76.8 mmoles) was dissolved in anhydrous dichloromethane (250 mL) and acetic anhydride (21 mL, 223 mmoles) and anhydrous pyridine (18 mL, 223 mmoles) were added carefully. The solution was refluxed under dry nitrogen for 30 hours, then cooled to room temperature. The solution was washed twice with 1M aqueous hydrochloric acid (200 mL portions) and then with saturated aqueous sodium chloride (200 mL). The dichloromethane solution was dried over anhydrous magnesium sulfate, filtered, and evaporated to an off-white solid. This crude product was flash chromatographed on silica gel (250 grams) using hexanes:ethyl acetate (70:30 [v/v]) as the eluting solvent. Fractions containing the major product ($R_f$=0.3) were pooled and evaporated to dryness to afford 19.0 grams (98% yield) of a white solid of methyl 4-methyl-2,6-diacetoxybenzoate (m.p. 70°–71° C., open capillary, uncorrected).

$^1$H NMR (300 MHz, CHCl$_3$-d) δ2.27 (singlet, 6H, COCH$_3$), 2.37 (singlet, 3H, ArCH$_3$), 3.83 (singlet, 3H, OCH$_3$), 6.84 (singlet, 2H, ArH). $^{13}$C NMR (75 MHz, CHCl$_3$-d) δ20.9, 21.5, 52.4, 116.5, 122.1, 143.8, 150.2, 163.9, 169.4.

Methyl 4-bromomethyl-2,6-diacetoxybenzoate

Methyl 4-methyl-2,6-diacetoxybenzoate (14.9 grams, 56.0 mmoles) was dissolved in carbon tetrachloride (200 mL), and N-bromosuccinimide (11.1 grams, 62.2 mmoles) and benzoyl peroxide (0.2 grams, 0.8 mmoles) were added. The mixture was refluxed under nitrogen. After 3.5 hours, an additional portion (0.2 grams) of N-bromosuccinimide was added. Reflux was continued for an additional hour. The reaction mixture was cooled to room temperature and then in ice for 1 hour, and the solid removed by filtration. The filtrate was evaporated to dryness. Hexanes (250 mL) was added to the residue, and the mixture was boiled until dissolution was obtained. The hexanes solution was concentrated to about 75 mL when a solid just began to precipitate. The mixture was heated to dissolve the solid, and the solution was allowed to cool slowly to room temperature. White crystals formed slowly, and the mixture was chilled in ice for 2 hours to complete crystallization. The solid was filtered, washed with cold hexanes (100 mL), and dried in vacuo to afford 11.9 grams (62% yield) of methyl 4-bromomethyl-2,6-diacetoxy-benzoate (m.p. 93°–95° C., open capillary, uncorrected). The product was contaminated with a small amount of methyl 2,6-diacetoxy-4-dibromomethylbenzoate, which did not interfere with subsequent reactions.

$^1$H NMR (300 MHz, CHCl$_3$-d) δ2.29 (singlet, 6H, COCH$_3$), 3.85 (singlet, 3H, OCH$_3$), 4.41 (singlet, 2H, CH$_2$), 7.08 (singlet, 2H, ArH). $^{13}$C NMR (75 MHz, CHCl$_3$-d) δ20.9, 30.9, 52.7, 119.6, 121.8, 142.4, 150.2, 163.5, 169.1.

Methyl 4-aminomethyl-2,6-dihydroxybenzoate hydrochloride

Methyl 4-bromomethyl-2,6-diacetoxybenzoate (45.8 grams, 133 mmoles) was dissolved in N,N-dimethylformamide (150 mL), and sodium azide (8.8 g, 135 mmoles) was added. The reaction mixture was stirred for 6 hours at room temperature. Dichloromethane (350 mL) was added to the reaction mixture, and this solution was washed with water (250 mL), 1M aqueous hydrochloric acid (250 mL), and saturated aqueous sodium chloride (150 mL). The organic solution was dried over anhydrous magnesium sulfate, filtered, and evaporated to a clear, pale yellow oil. The oil was dissolved in methanol (750 mL) and transferred to a 2 L Parr hydrogenation flask. Palladium on carbon catalyst (10% [w/w], 1.5 g) in water (10 mL) was added, followed by concentrated hydrochloric acid (15 mL). The flask was affixed to a Parr hydrogenator, and the mixture was shaken at room temperature under 30 psi of hydrogen for 24 hours. The reaction mixture was filtered through a 0.45 mm nylon filter. The retained solid was then washed with methanol (150 mL), and concentrated hydrochloric acid (7 mL) was added to the filtrate. The filtrate was heated to reflux for 2 hours, cooled to room temperature, and evaporated to dryness to give an off-white solid. This solid was dissolved in hot denatured ethanol (250 mL) and the solution was allowed to cool to room temperature. White crystals formed quickly. The mixture was then chilled for 16–18 hours at 4° C. to complete crystallization. The solid was filtered, washed with a little cold ethanol (50 mL) and then diethyl ether (150 mL), and dried in vacuo over potassium hydroxide pellets to afford 16.0 grams (52% yield based on monobromo starting material) of methyl 4-aminomethyl-2,6-dihydroxybenzoate hydrochloride (m.p. >260° C., open capillary, uncorrected).

$^1$H NMR (300 MHz, DMSO-d$_6$) δ3.77 (singlet, 3H, OCH$_3$), 3.83 (singlet, 2H, CH$_2$), 6.44 (singlet, 2H, ArH), 8.35 (broad singlet, 3H, NH$_3$), 10.20 (singlet, 2H, OH). $^{13}$C NMR (75 MHz, DMSO-d$_6$) δ41.9, 52.1, 107.2, 107.3, 138.5, 157.6, 168.3.

EXAMPLE CII

Preparation of a Reagent of General Formula CI
Methyl (6-Aminohexanoyl)aminomethyl-2,6-dihydroxybenzoate Hydrochloride

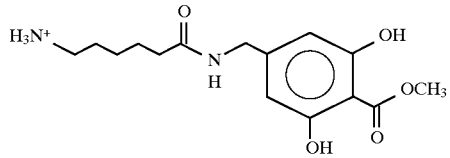

Methyl (N-tert-butoxycarbonyl-6-aminohexanoyl) aminomethyl-2,6-dihydroxybenzoate Methyl 4-aminomethyl-2,6-dihydroxybenzoate hydrochloride (1.50 grams, 6.4 mmoles) was suspended in anhydrous N,N-dimethylformamide (25 mL), and N,N-diisopropylethylamine (2.2 mL, 12.8 mmoles) was added, followed by N-tert-butoxycarbonyl-6-aminohexanoic acid succinimidyl ester (2.10 grams, 6.4 mmoles). The mixture was stirred under dry nitrogen for 4 hours, during which time all solids dissolved. The solvent was then evaporated to leave a light brown syrup, which was partitioned between ethyl acetate (70 mL) and 1M aqueous hydrochloric acid (50 mL). The layers were separated, and the ethyl acetate solution was washed with saturated aqueous sodium bicarbonate (50 mL) and saturated aqueous sodium chloride (50 mL). The ethyl acetate solution was dried over anhydrous sodium sulfate, filtered, and evaporated to an amorphous off-white solid. The solid was crystallized from ethyl acetate/hexanes, filtered, and dried in vacuo to afford 2.10 grams (80% yield) of methyl (N-tert-butoxycarbonyl-6-aminohexanoyl)aminomethyl-2,6-dihydroxybenzoate (m.p. 73°–76° C., open capillary, uncorrected).

$^1$H NMR (300 MHz, DMSO-d$_6$) δ1.26 (multiplet, 2H, NHCH$_2$CH$_2$CH$_2$CH$_2$CH$_2$CO), 1.36 (multiplet, 2H, CH$_2$CH$_2$CO), 1.36 (singlet, 9H, C(CH$_3$)$_3$), 1.50 (multiplet, 2H, NHCH$_2$CH$_2$), 2.10 (triplet, J=7 Hz, 2H, CH$_2$CH$_2$CO), 2.87 (quartet, J=6 Hz, 2H, NHCH$_2$CH$_2$), 3.78 (singlet, 3H, OCH$_3$), 4.08 (doublet, J=6 Hz, 2H, CH$_2$Ar), 6.23 (singlet, 2H, ArH), 6.75 (triplet, J=6 Hz, 1H, CONHCH$_2$CH$_2$), 8.26 (triplet, J=6 Hz, 1H, CONHCH$_2$Ar), 10.04 (singlet, 2H, OH). $^{13}$C NMR (75 MHz, CHCl$_3$-d) δ25.0, 26.0, 28.3, 29.3, 35.3, 41.7, 52.0, 77.4, 104.3, 105.6, 145.8, 155.8, 158.2, 169.0, 172.4.

Methyl (6-aminohexanoyl)aminomethyl-2,6-dihydroxybenzoate hydrochloride

Methyl (N-tert-butoxycarbonyl-6-aminohexanoyl) aminomethyl-2,6-dihydroxybenzoate (2.00 grmas, 4.87 mmoles) was dissolved in ethyl acetate (50 mL), and dry hydrogen chloride was bubbled slowly through the solution. The reaction mixture warmed as the gas dissolved. After 5 minutes, the gas was shut off, and the solution was stirred at room temperature. A white precipitate formed in the solution. After 30 minutes, the reaction mixture was chilled in ice for 2 hours, then the solid was filtered, washed with ethyl acetate (50 mL) and then diethyl ether (50 mL), and dried in vacuo over potassium hydroxide pellets to afford 1.68 grams (99% yield) of methyl (6-aminohexanoyl)aminomethyl-2,6-dihydroxybenzoate hydrochloride (m.p. shrinks at 145° C., decomposes with effervescence at 152°–154° C., open capillary, uncorrected).

$^1$H NMR (300 MHz, DMSO-d$_6$) δ1.29 (multiplet, 2H, H$_3$CH$_2$CH$_2$CH$_2$CH$_2$CH$_2$CO), 1.55 (multiplet, 4H, NH$_3$CH$_2$CH$_2$CH$_2$CH$_2$CH$_2$CO), 2.13 (triplet, J=8 Hz, 2H, CH$_2$CH$_2$CO), 2.70 (multiplet, 2H, NH$_3$CH$_2$CH$_2$), 3.75 (singlet, 3H, OCH$_3$), 4.07 (doublet, J=6 Hz, 2H, CH$_2$Ar), 6.26 (singlet, 2H, ArH), 8.05 (broad singlet, 3H, NH$_3$), 8.39 (triplet, J=6 Hz, 1H, CONHCH$_2$Ar), 9.84 (broad singlet, 2H, OH). $^{13}$C NMR(75 MHz, CHCl$_3$-d) δ24.8, 25.6, 26.7, 35.1, 41.8, 52.0, 104.7, 105.5, 145.5, 158.1, 169.0, 172.3.

EXAMPLE CIII

Preparation of a Reagent of General Formula CI
Methyl N-Bromoacetyl-4-aminomethyl-2,6-dihydroxybenzoate

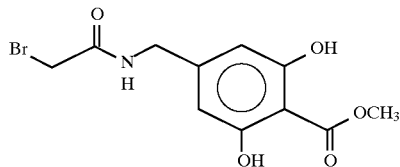

Methyl N-Bromoacetyl-4-aminomethyl-2,6-dihydroxybenzoate

Bromoacetic acid (0.30 grams, 2.16 mmol) was dissolved in dry N,N-dimethylformamide (15mL) and N-hydroxysuccinimide (0.25 grams, 2.21 mmol) and 1,3-dicyclohexylcarbodiimide (0.44 grams, 2.14 mmol) were added. The solution was stirred at room temperature for 1.25 hours. Methyl 4-aminomethyl-2,6-dihydroxybenzoate hydrochloride (0.50 grams, 2.14 mmol) was added, followed by N,N-diisopropylethylamine (0.38 mL, 2.15 mmol). The reaction mixture was stirred at room temperature for 2.5 hours, and was then diluted with ethyl acetate (100 mL). The mixture was filtered, and the filtrate washed twice with 1N aqueous hydrochloric acid (100 mL then 50 mL) and with saturated aqueous sodium chloride (50 mL). The organic solution was dried over anhydrous magnesium sulfate, filtered, and evaporated to dryness. The crude product was purified by chromatography on silica gel, eluting with hexanes:ethyl acetate (1:1 [v/v]). Fractions containing pure product were pooled and evaporated to dryness to afford 0.43 grams of a white solid (63% yield) of methyl N-bromoacetyl-4-aminomethyl-2,6-dihydroxybenzoate (m.p. 157°–158° C.).

$^1$H NMR (300 MHz, DMSO-d$_6$) δ3.77 (singlet, 3H, OCH$_3$), 4.11 (singlet, 2H, BrCH$_2$), 4.13 (doublet, J=6 Hz, 2H, CH$_2$NH), 6.25 (singlet, 2H, ArH), 8.70 (triplet, J=6 Hz, 1H, CH$_2$NH), 10.05 (singlet, 2H, OH). $^{13}$C NMR (75 MHz, DMSO-d$_6$) δ42.3, 42.6, 52.1, 104.7, 105.7, 144.7, 158.2, 166.3, 168.9.

EXAMPLE CIV

Preparation of a Reagent of General Formula CI
Methyl 4-Glutarylaminomethyl-2,6-dihydroxybenzoate Succinimidyl Ester

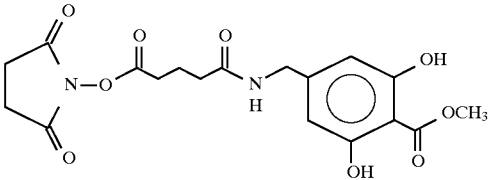

Methyl 4-glutarylaminomethyl-2,6-dihydroxybenzoate

Glutaric anhydride (2.3 grams, 20 mmoles) was dissolved in dry tetrahydrofuran (100 mL), and the suspension was stirred under nitrogen. N,N-diisopropylethylamine (7.0 mL, 40 mmoles) was added, followed by methyl 4-aminomethyl-2,6-dihydroxybenzoate hydrochloride (4.7 grams, 20 mmoles). After stirring for 18 hours, the mixture was evaporated to dryness, and the resulting solid was dissolved in dichloromethane (100 mL) and allowed to sit at room temperature for 2 hours. The dichloromethane solution was evaporated to dryness to give a thick syrup, which was treated with cold 1M aqueous hydrochloric acid (100 mL) for 30 minutes in ice. An off-white solid precipitated, which was filtered, washed with cold water, and dried in vacuo to afford 5.5 grams (88% yield) of methyl 4-glutarylaminomethyl-2,6-dihydroxybenzoate (m.p. 163°–164° C.).

$^1$H (300 MHz, DMSO-d$_6$) δ1.74 (quintet, J=8 Hz, 2H, CH$_2$CH$_2$CH$_2$), 2.16 (triplet, J=8 Hz, 2H, CH$_2$CONH), 2.20 (triplet, J=8 Hz, 2H, HO$_2$CCH$_2$), 3.78 (singlet, 3H, OCH$_3$), 4.10 (doublet, J=6 Hz, 2H, ArCH$_2$NH), 6.23 (singlet, 2H, ArH), 8.31 (triplet, J=6 Hz, 1H, NH), 10.05 (broad singlet, 3H, OH and CO$_2$H). $^{13}$C NMR (75 MHz, DMSO-d$_6$) δ20.7, 33.1, 34.4, 41.8, 52.1, 104.4, 105.6, 145.7, 158.2, 169.0, 172.0, 174.5.

Methyl 4-glutarylaminomethyl-2,6-dihydroxybenzoate succinimidyl ester

Methyl 4-glutarylaminomethyl-2,6-dihydroxybenzoate (2.0 grams, 6.4 mmoles) was dissolved in dry tetrahydrofuran (80 mL), and N-hydroxysuccinimide (0.8 grams, 7.0 mmoles) and 1,3-dicyclohexylcarbodiimide (1.3 grams, 6.4 mmoles) were added. The mixture was stirred at room temperature under dry nitrogen, and the solids rapidly dissolved. After about 20 minutes, a white precipitate formed. The reaction mixture was stirred 16–18 hours, then chilled several hours at −20° C. The mixture was filtered cold, and the solid washed with a little tetrahydrofuran (25 mL). The combined filtrates were evaporated to dryness, and the residue was crushed under ice-cold water (25 mL). The solid was filtered, washed quickly with cold water (25 mL) and then diethyl ether (100 mL), and dried in vacuo. The solid was recrystallized from ethyl acetate/hexanes to afford 2.5 grams (95% yield) of methyl 4-glutarylaminomethyl-2,6-dihydroxybenzoate succinimidyl ester (m.p. 161°–163° C.).

$^1$H NMR (300 MHz, DMSO-d$_6$) δ1.83 (quintet, J=8 Hz, 2H, CH$_2$CH$_2$CH$_2$), 2.26 (triplet, J=8 Hz, 2H, CH$_2$CONH), 2.73 (triplet, J=8 Hz, 2H, NO$_2$CCH$_2$), 2.80 (singlet, 4H, COCH$_2$CH$_2$CO), 3.77 (singlet, 3H, OCH$_3$), 4.10 (doublet, J=6 Hz , 2H, ArCH$_2$NH), 6.24 (singlet, 2H, ArH), 8.35 (triplet, J=6 Hz, 1H, NH), 10.04 (broad singlet, 2H, OH). $^{13}$C NMR (75 MHz, DMSO-d$_6$) δ20.4, 25.4, 29.7, 33.6, 41.8, 52.0, 104.5, 105.6, 145.5, 158.1, 168.9, 170.5, 171.4.

EXAMPLE CV

Preparation of a Reagent of General Formula CI
Methyl 4-Glutarylaminomethyl-2,6-dihydroxybenzoic Acid Hydrazide

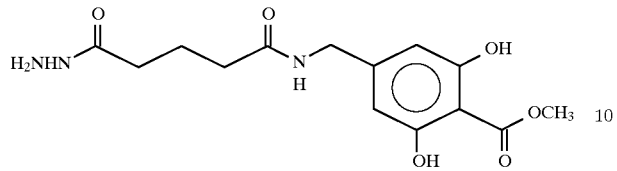

Methyl 4-glutarylaminomethyl-2,6-dihydroxybenzoate N-tert-butyloxycarbonylhydrazide Methyl 4-glutarylaminomethyl-2,6-dihydroxybenzoate succinimidyl ester (1.6 grams, 3.9 mmoles) was suspended in dry dichloromethane (50 mL), and tert-butylcarbazate (0.50 grams, 3.9 mmoles) was added. The reaction was stirred at room temperature for 24 hours. The pale solution was then washed twice with saturated aqueous sodium bicarbonate (50 mL portions), 0.1M aqueous hydrochloric acid (50 mL), and saturated aqueous sodium chloride (50 mL). It was then dried over anhydrous sodium sulfate, filtered, and evaporated to dryness. The residue was flash chromatographed on a 2.5×150 cm column of silica gel, eluting with ethyl acetate. Fractions containing pure product were pooled and evaporated to a clear syrup. This syrup was crystallized from ethyl acetate:hexanes at −20° C. The solid was filtered, washed with cold hexanes, and dried in vacuo to afford 1.0 grams (62% yield) of methyl 4-glutarylaminomethyl-2,6-dihydroxybenzoate N-tert-butyloxycarbonylhydrazide (m.p. 95°–100° C., softens at 88° C., open capillary, uncorrected).

$^1$H (300 MHz, DMSO-$d_6$) δ1.37 (singlet, 9H, $(CH_3)_3C$), 1.74 (quintet, J=7 Hz, 2H, $CH_2CH_2CH_2$), 2.07 (triplet, J=7 Hz, 2H, $CH_2CONHCH_2$), 2.15 (triplet, J=7 Hz, 2H, HNHNOCCH$_2$), 3.77 (singlet, 3H, OCH$_3$), 4.09 (doublet, J=6 Hz, 2H, ArCH$_2$NH), 6.23 (singlet, 2H, ArH), 8.28 (triplet, J=6 Hz, 1H, NH), 8.65 (singlet, 1H, NHNHCOCH$_2$), 9.47 (singlet, OCONHNH), 9.96 (singlet, 2H, OH). $^{13}$C NMR (75 MHz, DMSO-$d_6$) δ21.2, 28.0, 32.7, 34.7, 41.8, 52.1, 79.1, 104.4, 105.6, 145.7, 155.5, 158.2, 169.0, 171.7, 172.0.

Methyl 4-Glutarylaminomethyl-2,6-dihydroxybenzoic Acid Hydrazide

Methyl 4-glutarylaminomethyl-2,6-dihydroxybenzoate N-tert-butyloxycarbonyl hydrazide (0.50 grams, 1.2 mmoles) is dissolved in dry tetrahydrofuran (25 mL), and dry hydrogen chloride was bubbled slowly through the solution. The reaction mixture warmed as the gas dissolved. After 5 minutes, the gas was shut off, and the solution was stirred at room temperature. A white precipitate formed in the solution. After 30 minutes, the reaction mixture was chilled in ice for 2 hours, then the solid was filtered, washed with diethyl ether (50 mL), and dried in vacuo over potassium hydroxide pellets to afford 0.42 grams (98% yield) of methyl 4-glutarylaminomethyl-2,6-dihydroxybenzoic acid hydrazide (m.p. 158°–159° C., decomposed with effervescence, open capillary, uncorrected).

$^1$H (300 MHz, DMSO-$d_6$) δ1.76 (quintet, J=7 Hz, 2H, $CH_2CH_2CH_2$), 2.16 (triplet, J=7 Hz, 2H, $CH_2CONHCH_2$), 2.21 (triplet, J=7 Hz, 2H, H$_3$NHNOCCH$_2$), 3.75 (singlet, 3H, OCH$_3$), 4.07 (doublet, J=6 Hz, 2H, ArCH$_2$NH), 5.00–7.00 (very broad singlet, 2H, OH), 6.25 (singlet, 2H, ArH), 8.39 (triplet, J=6 Hz, 1H, NH), 10.49 (broad singlet, 3H, NHNH$_3$), 11.09 (singlet, 1H, NHNH$_3$). $^{13}$C NMR (75 MHz, CHCl$_3$-d) δ20.9, 32.2, 34.4, 41.8, 52.0, 104.8, 105.6, 145.5, 158.1, 169.0, 171.6, 171.9.

EXAMPLE CVI

Preparation of a Reagent of General Formula CIII
Synthesis of 4-Glutarylaminomethyl-2,6-dihydroxybenzohydroxamic Acid Hydrazide

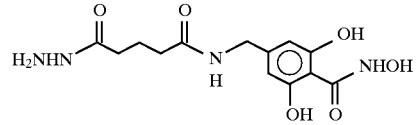

4-Glutarylaminomethyl-2,6-dihydroxybenzohydroxamic Acid N-tert-Butyloxycarbonylhydrazide Methyl 4-glutarylaminomethyl-2,6-dihydroxybenzoate N-tert-butyloxycarbonylhydrazide (0.30 grams, 0.7 mmoles) was added to a cooled (ice/water bath) solution of hydroxylamine sulfate (0.12 grams, 0.7 mmoles), sodium hydroxide (0.15 grams, 3.6 mmoles) and sodium sulfite (0.05 grams, 0.4 mmoles) in water (6 mL). The suspension was stirred for 24 hours in the dark, allowing it to warm to room temperature. The solution was dilute with 1M hydrochloric acid (4 mL), and extracted twice with ethyl acetate (15 mL portions). The combined ethyl acetate extracts were washed with water (10 mL) and saturated aqueous sodium chloride (10 mL), dried over anhydrous magnesium sulfate, filtered, and evaporated to dryness. The residue was dissolved in a minimum volume of ethyl acetate, and diethyl ether was added to precipitate an orange gummy material. The gum was triturated under dry diethyl ether to produce a solid, which was filtered, washed with ether, and dried in vacuo to afford 0.21 grams (69% yield) of 4-glutarylaminomethyl-2,6-dihydroxybenzohydroxamic acid N-tert-butyloxycarbonylhydrazide (m.p. decomposed with effervescence at 60°–65° C., open capillary, uncorrected).

$^1$H (300 MHz, DMSO-$d_6$) δ1.37 (singlet, 9H, $(CH_3)_3C$), 1.73 (quintet, J=7 Hz, 2H, $CH_2CH_2CH_2$), 2.07 (triplet, J=7 Hz, 2H, $CH_2CONHCH_2$), 2.15 (triplet, J=7 Hz, 2H, HNHNOCCH$_2$), 4.08 (doublet, J=6 Hz, 2H, ArCH$_2$NH), 6.22 (singlet, 2H, ArH), 8.28 (triplet, J=6 Hz, 1H, NH), 8.65 (singlet, 1H, NHNHCOCH$_2$), 9.47 (singlet, OCONHNH), 10.77 (broad singlet, 1H, NHOH), 12.30 (broad singlet, 3H, ArOH and NHOH). $^{13}$C NMR (75 MHz, DMSO-$d_6$) δ21.3, 28.1, 32.7, 34.7, 41.7, 79.1, 100.1, 105.6, 145.8, 155.6, 159.8, 167.5, 171.7, 172.0.

4-Glutarylaminomethyl-2,6-dihydroxybenzohydroxamic acid hydrazide trifluoroacetate 4-Glutarylaminomethyl-2,6-dihydroxybenzohydroxamic acid tert-butyl carbazate (0.09 grams, 0.2 mmoles) was suspended in dry dichloromethane (5 mL), and trifluoroacetic acid (0.5 mL) was added. The solid dissolved on addition of the acid, and the reaction was stirred at room temperature for three hours. After one hour, an orange precipitate had formed. The precipitate was collected by filtration and dried in vacuo over potassium hydroxide pellets to afford 0.10 grams (100% yield) of 4-glutarylaminomethyl-2,6-dihydroxybenzohydroxamic acid hydrazide trifluoroacetate (m.p. 104°–108° C., open capillary, uncorrected).

$^1$H (300 MHz, DMSO-$d_6$) δ1.80 (quintet, J=7 Hz, 2H, $CH_2CH_2CH_2$), 2.17 (triple, J=7 Hz, 2H, $CH_2CONHCH_2$), 2.23 (triplet, J=7 Hz, 2H, HNHNOCCH$_2$), 4.09 (doublet, J=6 Hz, 2H, ArCH$_2$NH), 6.22 (singlet, 2H, ArH), 8.32 (triplet, J=6 Hz, 1H, NH), 8.95–10.60 (very broad singlet, 5H, NHNH$_3$ and NHOH), 11.80–12.95 (very broad singlet, 3H, ArOH and NHOH). $^{13}$CNMR (75 MHz, DMSO-d$_6$) δ20.9, 32.2, 34.4, 41.8, 100.1, 105.7, 145.8, 158.5, 159.0, 159.9, 167.5, 171.8, 171.9.

EXAMPLE CVII

Preparation of Conjugates of General Formula CIV
Synthesis of 5'-PBA-labeled Oligodeoxyribonucleotide Conjugates Oligodeoxyribonucleotide 7172 (sequence 5'-GATTACGCCAGTTGTACGGAC-3') was synthesized on a 1 μmole scale using standard automated phosphoramidite chemistry (Beckman Instruments Oligo 1000 and associated reagents). A protected amine-containing phosphor-amidite (Aminolink 2, Applied Biosystems or UniLink Amino Modifier, Clontech) was employed on the same instrument to introduce one to four, reactive primary amines onto the 5'-end of the oligodeoxyribonucleotide using standard chemistry. The completed oligodeoxyribonucleotide was then cleaved from the support and the nucleobases deprotected using an UltraFast Deprotection kit (Beckman Instruments) and the protocol supplied by the manufacturer.

The amino-oligonucleotides were purified by ethanol precipitation, dissolved in 0.8 mL of 0.1M NaHCO$_3$, and condensed with phenylboronic acid reagent (PBA—Z—NHS) having a reactive N-hydroxysuccinimidyl ester moiety (5 mgs per mmole of primary amino groups on the amino-oligonucleotide in 0.2 mL of anhydrous N,N-dimethylformamide) for 2–18 hours at room temperature.

The crude PBA-modified oligonucleotide was isolated from the reaction mixture by gel filtration on a KwikSep Dextran column (Pierce Chemical) in 0.1M aqueous triethylammonium acetate, pH 6.5. The PBA-modified oligonucleotide was then concentrated in a vacuum centrifuge to 1 mL, and purified by reverse phase HPLC on a 4.6 mm×250 mm C18 column, with a triethylammonium acetate-acetonitrile gradient. The desired product peak was collected and evaporated to a small pellet in a vacuum centrifuge, dissolved in 0.5 mL of water, and stored frozen.

Preparation of Salicylhydroxamic Acid Magnetic Beads

Ten milliliters of unmodified M280 or M450 magnetic beads (Dynal) were gradually dehydrated into acetonitrile, and converted to aldehyde modified beads using oxalyl chloride activated N,N-dimethylsulfoxide and triethylamine in dichloromethane at −78° C. The resulting aldehyde bearing beads were gradually rehydrated and suspended in 5 mL of 0.1M sodium acetate pH 5.5. The aldehyde groups were coupled with 4-glutarylaminomethylsalicylhydroxamic acid hydrazide (SHA—Z—NHNH$_2$) by adding 15–25 mgs dissolved in 200 uL N,N-dimethylsulfoxide, and rotating coupling reaction over night at room temperature. The beads were then washed extensively with water and stored in 5 mL of 10% ethanol.

Preparation of Salicylhydroxamic Acid (SHA) Sepharose 4B

SHA-Sepharose 4B was prepared by mixing 130 mg of (6-aminohexanoyl)-4-amino-methylsalicylhydroxamic acid (SHA—Z—NH$_2$), dissolved in 30 mL 0.2M NaHCO$_3$, with 6.5 g HCl washed CNBr activated Sepharose 4B (Pharmacia) overnight at room temperature. After the coupling reaction, 2 mL of 0.5M Tris, pH 8.5 were added and the gel slurry mixed at room temperature for 1 hour, and washed with water, 0.5M NaCl, and water again. The resulting SHA-Sepharose 4B was suspended in 30 mL of 20% ethanol, and stored at 4° C.

Preparation of 2,6-Dihydroxybenzohydroxamic Acid (DHBHA) Sepharose 4B

DHBHA-Sepharose 4B was prepared by mixing 114 mg methyl (6-amino-hexanoyl)-4-aminomethyl-2,6-dihydroxybenzoate [DHBA(OMe)—X—NH$_2$], dissolved in 30 mL 0.2M NaHCO$_3$, with 5 g HCl washed CNBr activated Sepharose 4B (Pharmacia), overnight at room temperature. After the coupling reaction, the gel was washed with water and suspended in 50 mL 0.1M NH$_2$OH, pH 9, and rotated at room temperature for two hours. Finally, the gel was washed with water and suspended in 30 mL of 20% ethanol, and stored at 4° C.

Preparation of a Phenylboronic Acid-α-Biotin Antibody Conjugate

One milliliter of α-Biotin monoclonal IgG$_1$ antibody (6.5 mg/mL in 0.1M NaHCO$_3$) was conjugated with 440 nmoles of PBA—Z—NHS (7.4 ul of 60 mM PBA—Z—NHS dissolved in N,N-dimethylsulfoxide) for 1 hour at room temperature. Unconjugated PBA—Z—NHS and its hydrolysis products were removed by dialysis. The ultra-violet absorbance spectrum of the resulting conjugate (PBA-α-Biotin) exhibited an increase in A$_{260}$ relative to A$_{280}$ consistent with phenylboronic acid modification.

Preparation of a Phenylboronic Acid-Alkaline Phosphatase Conjugate

One milliliter of alkaline phosphatase (Sigma, 6 mg/mL) was dialyzed against one liter of 0.1M NaHCO$_3$, and conjugated with 700 nmoles of PBA—Z—NHS (10 uL of 70 mM stock in N,N-dimethylformamide) for two hours on ice. Unconjugated PBA—Z—NHS and its hydrolysis products were removed by dialysis in 0.1M NaHCO$_3$. The ultra-violet absorbance spectrum of the resulting conjugate (PBA—AP) exhibited an increase in A$_{260}$ relative to A$_{280}$ consistent with phenylboronic acid modification. The conjugate was stored at 4° C.

Preparation of a 2,6-Dihydroxybenzohydroxamic Acid-Alkaline Phosphatase Conjugate One milliliter of alkaline phosphatase (Sigma, 6 mg/mL) was dialyzed against one liter of 0.1M NaHCO$_3$, and conjugated with 714 nmoles of methyl 4-glutarylaminomethyl-2,6-di-hydroxybenzoate succinimidyl ester [DHBA(OMe)—Z—NHS] (10.5 uL of 68 mM in N,N-dimethylformamide) for two hours on ice. The methyl ester of the conjugate was converted to a hydroxamic acid by adding one milliliter of 2M NH$_2$OH, pH 10, and incubating the reaction at 4° C. for six days. The NH$_2$OH reaction mixture was then dialyzed against 0.1M NaHCO$_3$ and stored at 4° C.

Preparation of a Salicylhydroxamic Acid-Goat α-Mouse Antibody Conjugate

Two milliliters of goat α-mouse antibody (Rockland, 8.8 mg/mL in 0.1M NaHCO$_3$) were conjugated with 2.35 umoles of methyl 4-glutarylaminomethylsalicylate succinimidyl ester [SA(OMe)—Z—NHS] for 1 hour at room temperature. The methyl ester of the conjugate was converted to a hydroxamic acid by adding two milliliters of 2M NH$_2$OH, pH 10, adjusting the pH to 10 with 1N NaOH, and incubating the reaction at room temperature for three days. NH$_2$OH and unconjugated SA(OMe)—X—NHS and its hydrolysis products were removed by gel filtration on a G-25 Sephadex column (Pharmacia) in 0.1M NaHCO$_3$, and the conjugate (SHA-goat α-mouse) was stored at 4° C.

Preparation of a 2,6-Dihydroxybenzohydroxamic Acid-Goat α-Mouse Antibody

Two milliliters of goat α-mouse antibody (Rockland, 8.8 mg/mL in 0.1M NaHCO$_3$) were conjugated with 2.35 umoles of with DHBA(OMe)—Z—NHS for 1 hour at room temperature. The methyl ester of the conjugate was converted to a hydroxamic acid by adding two milliliters of 2M $NH_2OH$, pH 10, adjusting the pH to 10 with 1N NaOH, and incubating the reaction at room temperature for three days. $NH_2OH$ and unconjugated DHBA(OMe)—X—NHS and its hydrolysis products were removed by gel filtration on a G-25 Sephadex column (Pharmacia) in 0.1M $NaHCO_3$, and the conjugate (DHBHA-goat α-mouse) stored at 4° C.

Polymerase Chain Reaction (PCR) Protocol

A region of Lambda DNA (801 bp) was amplified by the polymerase chain reaction. The PCR reaction contained 200 uM dATP, dCTP, dGTP, and dTTP in addition to Biotin- and PBA- modified oligonucleotide primers at 1 uM in 1×PCR Buffer II (Perkin Elmer), Lambda DNA (1 ng/uL), and 1 U of *Thermus aquaticus* DNA polymerase. The reaction mixture was denatured at 92° C. for one minute and amplified by 35 cycles of PCR at 95° C. for 10 seconds, 62° C. for 20 seconds, and 72° C. for 30 seconds, with a final extension at 72° C. for 5 minutes. The reaction produced 50–100 ng of amplified product (801 bp), which exhibited retarded mobility relative to unmodified PCR product during electrophoresis on 1% agarose gels in 50 mM Tris, 100 mM borate, 2 mM EDTA, pH 8.3.

EXAMPLE CVIII

Preparation of Bioconjugates of General Formula CVI Sandwich Hybridization Detection of Nucleic Acid Probes A 42-mer oligonucleotide was hybridized with two 21-mer oligonucleotides bearing 5'-PBA and Biotin labels in 1.5M NaCl, 150 mM sodium citrate, pH 7, at 45° C. for ten minutes. Twenty-five microliters of the hybridization mixture was mixed with twenty five microliters of M280 streptavidin-magnetic particles (Dynal) in a polypropylene microtiter plate well. After 30 minutes, the magnetic particles were captured in the bottom of the well with a magnetic plate, and washed five times with 150 mM NaCl, 20 mM Tris-HCl, 0.02% Tween20, pH 8.

One hundred microliters of DHBHA—AP (1 ug/mL in 1 mg/mL BSA, 140 mM NaCl, 10 mM Tris-HCl, pH 8) were added to the magnetic particles and mixed well. After 30 minutes, the magnetic particles were captured in the bottom of the well with a magnetic plate, and washed six times with 150 mM NaCl, 20 mM Tris-HCl, 0.02% Tween20, pH 8. Alkaline phosphatase substrate (1 mg/mL p-nitrophenylphosphate in 1M diethanolamine buffer, 1 mM $MgCl_2$, 0.1 mM $ZnCl_2$, pH 10.4) was added, and incubated at 37° C. for 90 minutes. The Absorbance at 405 nm ($A_{405}$) was measured with an ELISA plate reader (Molecular Devices).

A strong $A_{405}$ was produced when all components of the hybridization sandwich were present, and the signal was proportional to the amount of 42-mer present. Experimental controls lacking either the 42-mer, the Biotin-oligonucleotides and PBA-oligonucleotides did not produce a significant $A_{405}$.

EXAMPLE CIX

Preparation of Bioconjugates of General Formula CVI
Detection of PBA-Labeled PCR Product on DHBHA-Coated Microtiter Plates The wells of a polystyrene microtiter plate (Becton Dickinson) were coated with DHBHA by filling the wells with 200 uL of DHBHA-goat α-mouse conjugate (30 ug/mL in 0.1M $NaHCO_3$ pH 9.0) and incubating overnight at 4° C. The coating solution was removed and the plate backcoated with 5 mg/mL BSA (300 ul per well in 0.2M $NaHCO_3$, pH 9.0) for 1 hour at room temperature. The BSA solution was removed by washing the plate five times with ELISA Wash Buffer (150 mM NaCl, 20 mM Tris-HCl, 0.02% Tween 20, pH 8.0).

One hundred microliters of unpurified PBA and biotin labeled PCR product were added to 900 ul of 1.5N NaCl, 150 mM sodium citrate, pH 7.0 (10×SSC) and serially-diluted in 10×SSC. One hundred microliters of the diluted PCR products were added to the wells and incubated for one hour at room temperature. The plate was then washed five times with ELISA Wash Buffer, and 100 ul of Streptavidin-Alkaline Phosphatase (Boehringer Mannheim, 0.2 U/mL in 1 mg/ml BSA, 140 mM NaCl, 10 mM Tris-HCl, pH 8.0) were added to each well and incubated for thirty minutes at room temperature.

The plate was washed 5 times with ELISA Wash Buffer, and 200 ul of p-nitrophenylphosphate (1 mg/mL in diethanolamine, 1 mM $MgCl_2$, 0.1 mM $ZnCl_2$, pH 10.4) were added to the plate and incubated at 37° C. for 30–60 minutes. Less than 1 uL of PCR product was detected. PCR product lacking either PBA or biotin labels was not detected.

EXAMPLE CX

Preparation of Bioconjugates of General Formula CVI Detection of PBA-Labeled PCR Product
Detection of PBA-Labeled PCR Product on SHA-Magnetic Beads PBA-labeled PCR product (0.02 μL–5 μL) was diluted into 25–100 μL of 1.5M NaCl, 150 mM sodium citrate, pH 7 (10×SSC), and added to a polypropylene microtiter plate well containing SHA-magnetic particles (10–50 ul). The particles and PCR product were mixed occasionally for 30–60 minutes at room temperature. The magnetic particles were captured in the bottom of the wells with a magnetic plate and washed five times in 150 mM NaCl, 20 mM Tris-HCl, 0.02% Tween 20, pH 8 (ELISA Wash Buffer). One hundred microliters of streptavidin alkaline-phosphatase (Boehringher Mannheim, 0.2 U/mL in 1 mg/mL BSA, NaCl, Tris-HCl, $pH_8$) were added and mixed with the magnetic particles for 30 minutes at room temperature. The magnetic particles were captured in the bottom of the wells with a magnetic plate and washed 5 times with ELISA Wash. Alkaline phosphatase substrate was added (1 mg/ml p-nitrophenyl phosphate in 1M diethanolamine buffer, 1 mM $MgCl_2$, 0.1 mM $ZnCl_2$, pH 10.4), and the color developed at 37° C. for 10–60 minutes. The lower limit of detection was 50 pg of PCR product.

EXAMPLE CXI

Preparation of Bioconjugates of General Formula CVI Detection of a PBA-Labeled Oligonucleotide Hybrid Detection of a PBA-Labeled Oligonucleotide Hybridized to a Biotin-Labeled Oligonucleotide A 42-mer oligonucleotide was hybridized with two 21-mer oligonucleotides bearing 5'-PBA and Biotin labels in 1.5M NaCl, 150 mM sodium citrate, pH 7, at 45 C. for ten minutes. Twenty-five microliters of the hybridization mixture was mixed with 1–50 uL of SHA-magnetic particles (Dynal, M450) in a polypropylene microtiter plate well. After 30 minutes, the magnetic particles were captured in the bottom of the well with a magnetic plate, and washed five times with 150 mM NaCl, 20 mM Tris-HCl, 0.02% Tween 20, pH 8.

One hundred microliters of SHA—AP (1 ug/mL in 1 mg/L BSA, 140 mM NaCl, 10 mM Tris-HCl, pH 8) were added to the magnetic particles and mixed well. After 30 minutes, the magnetic particles were captured in the bottom of the well with a magnetic plate, and washed six times with 150 mM NaCl, 20 mM Tris-HCl, 0.02% Tween 20, pH 8. The particles were mixed with alkaline phosphatase substrate (1 mg/mL p-nitrophenyl phosphate in 1M diethanolamine buffer, 1 mM $MgCl_2$, 0.1 mM $ZnCl_2$, pH 10.4) and incubated at 37° C. for 90 minutes. The $A_{405}$ was measured with a ELISA plate reader (Molecular Devices). As little as 45 pg of oligonucleotide 42-mer was detected. Experimental controls lacking either the 42-mer, or the PBA or Biotin labeled oligonucleotides did not produce a significant $A_{405}$.

EXAMPLE CXII
Preparation of Bioconjugates of General Formula CVI
Immobilization of a PBA-α-Biotin Conjugate on SHA-Sepharose 4B One mg of PBA-(α-Biotin, diluted to 1 mL with Tris buffered saline, was applied to small column of SHA-Sepharose 4B (1.0×2.0 cm), and washed extensively with Tris buffered saline. The size of the $A_{280}$ peak of the material not binding to the column indicated that almost all of the PBA-conjugate was immobilized on the column.

Biotin binding activity of the column was assayed by applying to the column 5 mL of 1 ug/mL biotinylated alkaline phosphatase in Tris buffered saline containing 5 mg/mL bovine serum albumin (BSA). A sample of the peak of the material flowing through the column was collected for comparison of the enzymatic activity with a sample of the alkaline phosphatase dilution applied to column. After applying the sample, the column was washed with 20 mL of buffer. After washing, a very small sample of column material (25 uL liquid containing about 1 uL gel) was collected to measure the enzymatic activity bound to the gel as a result of capture by the immobilized α-biotin antibody.

The alkaline phosphatase activity was measured by incubating 25 uL of the enzyme samples in 250 uL of 1 mg/mL p-nitrophenylphosphate in 1M diethanolamine buffer, 1 mM $MgCl_2$, and 0.1 mM $ZnCl_2$, pH 10.4, for 20 minutes and then adding 650 uL of 0.1M $NaHCO_3$, 10 mM EDTA. Relative to a buffer blank, the $A_{405}$ of the sample applied to the column was 1.57, while the $A_{405}$ of the peak of the material not retained by the column was only 0.042, indicating that virtually all the enzyme conjugate was captured by the column. The small amount of gel assayed produced an $A_{405}$ of 1.30, demonstrating that the enzyme was in fact captured by the column.

EXAMPLE CXIII

Preparation of Bioconjugates of General Formula CVI
Immobilization of a PBA-Alkaline Phosphatase Conjugate on SHA-Magnetic Beads PBA-conjugated alkaline phosphatase was diluted to 5 ug/mL in Tris buffered saline containing 5 mg/mL bovine serum albumin. Two hundred microliters of diluted PBA-conjugated enzyme were mixed with 5, 10, or 20 uL of SHA-magnetic beads (Dynal, M280). The enzyme was also mixed with 40 uL of unmodified beads as a control. The beads were mixed gently for 10 minutes on ice, after which the beads were captured with a rare earth magnet and washed 4 times with Tris buffered saline. The beads were then suspended in 250 uL of 1 mg/mL p-nitrophenylphosphate in 1M diethanolamine buffer, 1 mM $MgCl_2$, and 0.1 mM $ZnCl_2$, pH 10.4, and mixed occasionally at 37° C. for 10 minutes. The reactions were terminated with 750 uL of Tris buffered saline, 5 mM EDTA. The $A_{405}$ relative to a buffer blank was measured to determine the alkaline phosphatase activity bound to the magnetic beads. The control beads produced an $A_{405}$ of only 0.15, while the SHA-magnetic beads produced an $A_{405}$ of 0.62, 0.97, and 1.33 for 5, 10, and 20 uL of beads, respectively, indicating the immobilization of significant amounts of PBA—AP conjugate on the surface of the beads.

We claim:

1. A conjugate of a biologically active species with a reagent having the general formula of General Formula CIV:

General Formula CIV

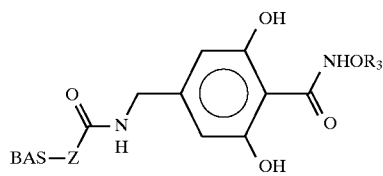

wherein group Z comprises a spacer selected from a saturated or unsaturated chain of up to about 6 carbon equivalents in length, an unbranched saturated or unsaturated chain of from about 6 to 18 carbon equivalents in length with at least one of intermediate amide and disulfide moieties, and a polyethylene glycol chain of from about 3 to 12 carbon equivalents in length;

wherein group $R_3$ is selected from one of an H, an alkyl, and a methylene or ethylene moiety with an electronegative substituent; and wherein BAS is a biologically active species.

2. The conjugate of claim 1, wherein group $R_3$ is selected from one of H, $CH_3$, $CH_2CH_3$, $CH_2CN$, $CH_2COOH$, $CH_2CONH_2$, $CH_2CH_2OH$, and $CH_2OCH_3$.

3. The conjugate of claim 1, wherein group Z is an unbranched alkyl chain of general formula $(CH_2)_n$, wherein n=1 to 6.

4. The conjugate of claim 1, having the general formula:

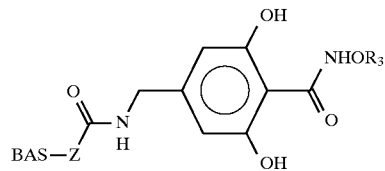

wherein group $R_3$ is H.

5. A bioconjugate having the general formula of General Formula CVI:

General Formula CVI

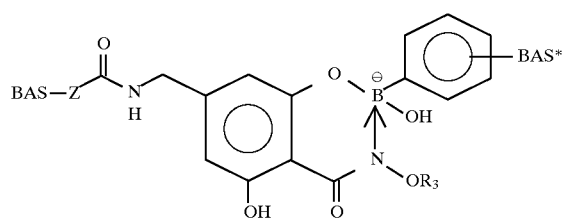

wherein group Z comprises a spacer selected from a saturated or unsaturated chain of up to about 6 carbon equivalents in length, an unbranched saturated or unsaturated chain of from about 6 to 18 carbon equivalents in length with one of intermediate amide and disulfide moieties, and a polyethylene glycol chain of from about 3 to 12 carbon equivalents in length;

wherein group $R_3$ is selected from one of H, an alkyl, and a methylene or ethylene with an electronegative moiety;

wherein BAS is a biologically active species; and wherein BAS* is a biologically active species.

6. The bioconjugate of claim 5, wherein group $R_3$ is selected from one of H, $CH_3$, $CH_2CH_3$, $CH_2CN$, $CH_2COOH$, $CH_2CONH_2$, $CH_2CH_2OH$, and $CH_2OCH_3$.

7. The bioconjugate of claim 5, wherein group Z is an unbranched alkyl chain of general formula $(CH_2)_n$, wherein n=1 to 6.

8. The bioconjugate of claim 5, wherein BAS and BAS* are different bioactive species.

* * * * *

UNITED STATES PATENT AND TRADEMARK OFFICE
CERTIFICATE OF CORRECTION

PATENT NO. : 5,872,224
DATED : February 16, 1999
INVENTOR(S) : Stolowitz et al.

It is certified that error appears in the above-identified patent and that said Letters Patent is hereby corrected as shown below:

Title page,
Item [56], References Cited, OTHER PUBLICATIONS,
"Sienkiewicz, P.A.," reference please delete "lorg." and insert -- Inorg. --.
"Imagawa et al.," reference please delete "aanti" and insert -- Anti- --.
"Imagawa et al.," reference please delete "Aplied" and insert -- Applied --.
"Bauer, L.," reference please delete "Internat. Edit.1" and insert -- Internat. Edit.; --.
"Ripan et al.," reference please delete "pp 965-171" and insert -- 965-71 --.
"Regneir, G.," reference please delete "pp 2821 . 2827" and insert -- pp 2821-27 --.
"Quelet," reference please delete "Bulletinde" and insert -- Bulletin de --.

Drawings,
Please insert the attached drawing sheets 8-14, of Figures 1' - 7'.

Column 7,
Line 39, please delete "General Formula cm" and insert -- General Formula CIII --.

Signed and Sealed this

Tenth Day of August, 2004

JON W. DUDAS
*Acting Director of the United States Patent and Trademark Office*

Step 1

Step 2

Step 3

Step 4

Step 5

Step 1

Step 2

Step 3

Step 4

Step 1

Bz = CH₂C₆H₅

Step 2

Step 3

Step 4

Step 5